United States Patent
Galley et al.

(10) Patent No.: US 7,875,645 B2
(45) Date of Patent: Jan. 25, 2011

(54) METHOD FOR THE TREATMENT OF CNS DISORDERS WITH SUBSTITUTED 2-IMIDAZOLES OR IMIDAZOLE DERIVATIVES

(75) Inventors: Guido Galley, Rheinfelden (DE); Katrin Groebke Zbinden, Liestal (CH); Marius Hoener, Basel (CH); Sabine Kolczewski, Rheinfelden (DE); Roger Norcross, Olsberg (CH); Henri Stalder, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 147 days.

(21) Appl. No.: 11/655,468

(22) Filed: Jan. 19, 2007

(65) Prior Publication Data

US 2007/0197621 A1 Aug. 23, 2007

(30) Foreign Application Priority Data

Jan. 27, 2006 (EP) .................................. 06100955

(51) Int. Cl.
*A61K 31/415* (2006.01)
*C07D 233/56* (2006.01)

(52) U.S. Cl. ................. 514/400; 548/355.1; 548/315.1; 548/335.1; 548/346.1; 548/347.1; 548/311.4; 514/396; 514/397; 514/401; 514/402

(58) Field of Classification Search ................. 514/400, 514/396, 397, 401, 402, 649; 548/311.4, 548/315.1, 335.1, 346.1, 347.1, 355.1
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,377,247 A | 4/1968 | Eble | |
| 3,586,695 A | 6/1971 | Wysong et al. | |
| 3,660,423 A | 5/1972 | Wysong et al. | |
| 3,818,035 A | 6/1974 | Binon et al. | |
| 4,146,647 A | 3/1979 | Lafon | |
| 4,665,095 A | 5/1987 | Winn et al. | |
| 2003/0149089 A1* | 8/2003 | Heerding et al. | 514/396 |
| 2007/0197620 A1 | 8/2007 | Galley et al. | |
| 2007/0197622 A1 | 8/2007 | Galley et al. | |
| 2007/0197659 A1 | 8/2007 | Wells | |

FOREIGN PATENT DOCUMENTS

| | | |
|---|---|---|
| CA | 2 246 027 A1 | 2/2000 |
| CS | 261294 * | 1/1989 |
| DE | 22 03 373 | 8/1972 |
| EP | 0 125 410 A2 | 11/1984 |
| EP | 0 924 209 | 6/1999 |
| EP | 1 103 243 A2 | 5/2001 |
| ES | 323 985 | 12/1966 |
| FR | 6 551 | 12/1968 |
| WO | WO 98/12183 | 3/1998 |
| WO | WO 01/81334 A2 | 11/2001 |
| WO | WO 02/22801 A2 | 3/2002 |

OTHER PUBLICATIONS

Huh, "A novel synthetic method for 2-arylmethyl substituted imidazolines and imidazoles from 2-aryl-1,1-dibromoethenes", Tetrahedron, 2004, 60, pp. 9857-9862.*
Miller, "Optically Active Catecholimidazolines: A Study of Steric Interactions at a- Adrenoreceptors", J Med Chem, 1983,26, 957-963.*
Deutch et al., (1999) Neurotransmitters. In Fundamental Neuroscience ($2^{nd}$ ed.) pp. 193-234, Academic Press.
Wong, et al., (2001) Nat. Rev. Neurosci. 2, pp. 343-351.
Carlsson. et al. (2001) Annu. Rev. Pharmacol. Toxicol. 41, pp. 237-260.

(Continued)

*Primary Examiner*—Sreeni Padmanabhan
*Assistant Examiner*—Sahar Javanmard
(74) *Attorney, Agent, or Firm*—George W. Johnston; Patricia S. Rocha-Tramaloni; Kimberly J. Prior

(57) ABSTRACT

The present invention relates a method for treating depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders which comprises administering to an individual a therapeutically effective amount of a compound of formula I

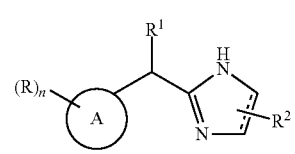

wherein
R, $R^1$, $R^2$, A and n are as defined in the specification
and to their pharmaceutically active salts. The invention also relates to novel compounds of formula I, pharmaceutical compositions containing them, and methods for their preparation.

4 Claims, No Drawings

OTHER PUBLICATIONS

Tuite et al., (2003) Expert Opin. Investig. Drugs 12, pp. 1335-1352.
Castellanos et al., (2002) Nat. Rev. Neurosci. 3, pp. 617-628.
Usdin, E.; Sandler, M.; Editors. Psychopharmacology Series, vol. 1: Trace Amines and the Brain. [Proceedings of a Study Group at the 14th Annual Meeting of the American College of Neuropsychoparmacology, San Juan, Puerto Rico] (1976), pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mousseau et al., (1995) Prog. Brain Res. 106, pp. 285-291.
McCormack et al. (1986) J. Neurosci. 6, pp. 94-101.
Dyck, L. E. (1989) Life Sci. 44, pp. 1149-1156.
Parker, et al. (1988) J. Pharmacol. Exp. Ther. 245, pp. 199-210.
Lindemann et al. (2005) Genomics 85, pp. 372-385.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Melloni et al., Eur. J. Med. Chem. vol. 26, pp. 207-213 (1991).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Bunzow, J.R., et al., Molecular Pharmacology, vol. 60(6), pp. 1181-1188 (2001), XP008008060.
Holt, Andrew, J. of Psychiatry & Neuroscience, vol. 28(6), pp. 409-414 (2003), XP002438693.
Yoshiya Amemiya, et al., J. of Medicinal Chemistry, vol. 35(4), pp. 750-755 (1992), XP002151512.
Faust, J.A., et al., J. of Organic Chemistry, vol. 26, pp. 4044-4047 (1961), XP002442336.
Savola, J.M., et al., Drug Research, vol. 38(1), pp. 29-35 (1988), XP002033085.
Nathanson, J.A., Molecular Pharmacology, col. 28(3), pp. 254-268 (1985), XP009085722.

* cited by examiner

METHOD FOR THE TREATMENT OF CNS DISORDERS WITH SUBSTITUTED 2-IMIDAZOLES OR IMIDAZOLE DERIVATIVES

PRIORITY TO RELATED APPLICATIONS

This application claims the benefit of European Application No. 06100955.1, filed Jan. 27, 2006, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

SUMMARY OF THE INVENTION

The present invention provides a method for treating a disorder selected from the group consisting of depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders which comprises administering to an individual a therapeutically effective amount of a compound of formula I

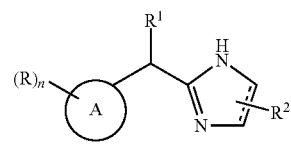

wherein
R is hydrogen,
   tritium,
   hydroxy,
   amino,
   lower alkyl,
   cycloalkyl,
   lower alkoxy,
   halogen,
   cyano,
   lower alkyl substituted by halogen,
   lower alkoxy substituted by halogen,
   phenyl, O-phenyl, or —S-phenyl, each of which is optionally substituted by halogen,
   benzyl,
   benzyloxy,
   NHC(O)-lower alkyl or
   pyridin-2, 3 or 4-yl;
$R^1$ is hydrogen, hydroxy or lower alkyl;
$R^2$ is hydrogen or lower alkyl;
A is an aryl group selected from the group consisting of phenyl, naphthalen-1-yl and naphthalen-2-yl; or a heteroaryl group, containing at least one O, N or S ring atom, selected from the group consisting of pyridine-3-yl, pyrazolyl, benzofuran-3-yl, benzofuran-4-yl, benzofuran-5-yl, benzofuran-6-yl, benzofuran-7-yl, thiophen-2-yl, thiophen-3-yl, benzo[b]thiophen-3-yl and indol-3-yl; and
n is 1, 2, 3, 4 or 5; when n is 2, 3, 4 or 5, R may be the same or different;
the dotted line represents an optional bond;
or a pharmaceutically active salt thereof.

The compounds of formula I have good affinity to the trace amine associated receptors (TAARs), especially for TAAR1.

Some of the compounds disclosed in formula I are known compounds, described for example in the below mentioned references, or are enclosed in public chemical libraries. Compounds of examples 1-113 and 155-223 are novel.

REFERENCES USED

1. Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2. Wong, M. L. and Licinio, J. (2001) Research and treatment approaches to depression. *Nat. Rev. Neurosci.* 2, 343-351;
3. Carlsson, A. et al. (2001) Interactions between monoamines, glutamate, and GABA in schizophrenia: new evidence. *Annu. Rev. Pharmacol. Toxicol.* 41, 237-260;
4. Tuite, P. and Riss, J. (2003) Recent developments in the pharmacological treatment of Parkinson's disease. *Expert Opin. Investig. Drugs* 12, 1335-1352,
5. Castellanos, F. X. and Tannock, R. (2002) Neuroscience of attention-deficit/hyperactivity disorder: the search for endophenotypes. *Nat. Rev. Neurosci.* 3, 617-628;
6. Usdin, E. and Sandler, M. eds. (1984), *Trace Amines and the brain*, Dekker;
7. Lindemann, L. and Hoener, M. (2005) A renaissance in trace amines inspired by a novel GPCR family. *Trends in Pharmacol. Sci.* 26, 274-281;
8. Branchek, T. A. and Blackburn, T. P. (2003) Trace amine receptors as targets for novel therapeutics: legend, myth and fact. *Curr. Opin. Pharmacol.* 3, 90-97;
9. Premont, R. T. et al. (2001) Following the trace of elusive amines. *Proc. Natl. Acad. Sci. U.S. A.* 98, 9474-9475;
10. Mousseau, D. D. and Butterworth, R. F. (1995) A high-affinity [3H] tryptamine binding site in human brain. *Prog. Brain Res.* 106, 285-291;
11. McCormack, J. K. et al. (1986) Autoradiographic localization of tryptamine binding sites in the rat and dog central nervous system. *J. Neurosci.* 6, 94-101;
12. Dyck, L. E. (1989) Release of some endogenous trace amines from rat striatal slices in the presence and absence of a monoamine oxidase inhibitor. *Life Sci.* 44, 1149-1156;
13. Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14. Lindemann, L. et al. (2005) Trace amine associated receptors form structurally and functionally distinct subfamilies of novel G protein-coupled receptors. *Genomics* 85, 372-385.

The preferred indications of the invention are depression, psychosis, Parkinson's disease, anxiety and attention deficit hyperactivity disorder (ADHD).

The invention relates also to novel compounds of formula I

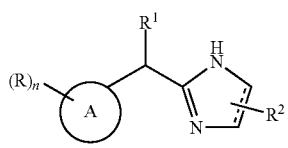

wherein
R is hydrogen,
 tritium,
 hydroxy,
 amino,
 lower alkyl,
 cycloalkyl,
 lower alkoxy,
 halogen,
 cyano,
 lower alkyl substituted by halogen,
 lower alkoxy substituted by halogen,
 phenyl, O-phenyl, —S-phenyl, each of which is optionally substituted by halogen,
 benzyl,
 benzyloxy,
 NHC(O)-lower alkyl or
 pyridin-2, 3 or 4-yl;
$R^1$ is hydrogen, hydroxy or lower alkyl;
$R^2$ is hydrogen or lower alkyl;
A is an aryl group selected from the group consisting of phenyl, naphthalen-1-yl and naphthalen-2-yl or a heteroaryl group, containing at least one O, N or S ring atom, selected from the group consisting of pyridine-3-yl, pyrazolyl, benzofuran-3-yl, benzofuran-4-yl, benzofuran-5-yl, benzofuran-6-yl, benzofuran-7-yl, thiophen-2-yl, thiophen-3-yl, benzo[b]thiophen-3-yl and indol-3-yl; and
n is 1, 2, 3, 4 or 5; when n is 2, 3, 4 or 5, R may be the same or different;
the dotted line represents an optional bond;

and their pharmaceutically active salts, with the exception of the following compounds ///
2-(4-tert-butyl-2,6-dimethyl-benzyl)-4,5-dihydro-1H-imidazole, Xylometazoline,
2-pentamethylphenylmethyl-4,5-dihydro-1H-imidazole,
2-(2,3,5,6-tetramethyl-benzyl)-4,5-dihydro-1H-imidazole,
6-tert-butyl-3-(4,5-dihydro-1H-imidazol-2-ylmethyl)-2,4-dimethyl-phenol, Oxymethazoline,
2-(2,4,6-trimethyl-benzyl)-4,5-dihydro-1H-imidazole, Trimizoline,
2-(2,6-dimethyl-benzyl)-4,5-dihydro-1H-imidazole,
2-(2,6-dichloro-benzyl)-4,5-dihydro-1H-imidazole,
2-(3,4-dichloro-benzyl)-4,5-dihydro-1H-imidazole,
2-(2,3-dimethoxy-benzyl)-4,5-dihydro-1H-imidazole,
2-(4-methoxy-2,6-dimethyl-benzyl)-4,5-dihydro-1H-imidazole,
2-(2-bromo-benzyl)-4,5-dihydro-1H-imidazole,
2,6-dichloro-4-(4,5-dihydro-1H-imidazol-2-ylmethyl)-phenylamine, Nemazoline,
2-(2-methyl-benzyl)-4,5-dihydro-1H-imidazole,
2-(2,5-dimethyl-benzyl)-4,5-dihydro-1H-imidazole,
2-(2-trifluoromethyl-benzyl)-4,5-dihydro-1H-imidazole,
2-(3-trifluoromethyl-benzyl)-4,5-dihydro-1H-imidazole,
2-benzyl-4,5-dihydro-1H-imidazole, Priscol, Tolazoline,
rac-2-(1-phenyl-ethyl)-4,5-dihydro-1H-imidazole,
rac-2-(1-phenyl-propyl)-4,5-dihydro-1H-imidazole,
rac-2-[1-(2-chloro-phenyl)-ethyl]-4,5-dihydro-1H-imidazole,
2-(2,5-dimethoxy-benzyl)-4,5-dihydro-1H-imidazole,
4-(4,5-dihydro-1H-imidazol-2-ylmethyl)-phenylamine,
2-(2-chloro-benzyl)-4,5-dihydro-1H-imidazole,
2-(2,4,6-trimethyl-benzyl)-1H-imidazole,
2-(2,6-dimethyl-benzyl)-1H-imidazole,
2-benzyl-1H-imidazole,
2-naphthalen-1-ylmethyl-4,5-dihydro-1H-imidazole, Privine,
2-naphthalen-2-ylmethyl-4,5-dihydro-1H-imidazole,
2-benzofuran-5-ylmethyl-4,5-dihydro-1H-imidazole,
2-benzo[b]thiophen-3-ylmethyl-4,5-dihydro-1H-imidazole,
2-thiophen-2-ylmethyl-4,5-dihydro-1H-imidazole,
2-thiophen-3-ylmethyl-4,5-dihydro-1H-imidazole,
3-(4,5-dihydro-1H-imidazol-2-ylmethyl)-1H-indole,
2-(1-phenyl-propyl)-4,5-dihydro-1H-imidazole,
2-(2-methoxy-benzyl)-1H-imidazole,
2-(2-methoxy-naphthalen-1-ylmethyl)-4,5-dihydro-1H-imidazole,
2-(4-methoxy-naphthalen-1-ylmethyl)-4,5-dihydro-1H-imidazole,
rac-2-(1-naphthalen-1-yl-ethyl)-4,5-dihydro-1H-imidazole,
2-biphenyl-2-ylmethyl-4,5-dihydro-1H-imidazole, 4-methyl-2-naphthalen-1-ylmethyl-4,5-dihydro-1H-imidazole, and
2-(2-methyl-naphthalen-1-ylmethyl)-4,5-dihydro-1H-imidazole.

Furthermore, the invention includes all racemic mixtures, all their corresponding enantiomers and/or optical isomers.

In addition, all tautomeric forms of compounds of formula I are also encompassed by the present invention.

The invention further provides a pharmaceutical composition comprising a therapeutically effective amount of a compound of formula I

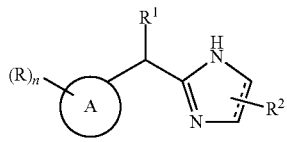

I wherein
R is hydrogen,
  tritium,
  hydroxy,
  amino,
  lower alkyl,
  cycloalkyl,
  lower alkoxy,
  halogen,
  cyano,
  lower alkyl substituted by halogen,
  lower alkoxy substituted by halogen,
  phenyl, O-phenyl, —S-phenyl, each of which is optionally substituted by halogen,
  benzyl,
  benzyloxy,
  NHC(O)-lower alkyl or
  pyridin-2, 3 or 4-yl;
$R^1$ is hydrogen, hydroxy or lower alkyl;
$R^2$ is hydrogen or lower alkyl;
A is an aryl group selected from the group consisting of phenyl, naphthalen-1-yl and naphthalen-2-yl or a heteroaryl group, containing at least one O, N or S ring atom, selected from the group consisting of pyridine-3-yl, pyrazolyl, benzofuran-3-yl, benzofuran-4-yl, benzofuran-5-yl, benzofuran-6-yl, benzofuran-7-yl, thiophen-2-yl, thiophen-3-yl, benzo[b]thiophen-3-yl and indol-3-yl; and
n is 1, 2, 3, 4 or 5; when n is 2, 3, 4 or 5, R may be the same or different;
the dotted line represents an optional bond;

and their pharmaceutically active salts, with the exception of the following compounds
2-(4-tert-butyl-2,6-dimethyl-benzyl)-4,5-dihydro-1H-imidazole, Xylometazoline,
2-pentamethylphenylmethyl-4,5-dihydro-1H-imidazole,
2-(2,3,5,6-tetramethyl-benzyl)-4,5-dihydro-1H-imidazole,
6-tert-butyl-3-(4,5-dihydro-1H-imidazol-2-ylmethyl)-2,4-dimethyl-phenol, Oxymethazoline,
2-(2,4,6-trimethyl-benzyl)-4,5-dihydro-1H-imidazole, Trimizoline,
2-(2,6-dimethyl-benzyl)-4,5-dihydro-1H-imidazole,
2-(2,6-dichloro-benzyl)-4,5-dihydro-1H-imidazole,
2-(3,4-dichloro-benzyl)-4,5-dihydro-1H-imidazole,
2-(2,3-dimethoxy-benzyl)-4,5-dihydro-1H-imidazole,
2-(4-methoxy-2,6-dimethyl-benzyl)-4,5-dihydro-1H-imidazole,
2-(2-bromo-benzyl)-4,5-dihydro-1H-imidazole,
2,6-dichloro-4-(4,5-dihydro-1H-imidazol-2-ylmethyl)-phenylamine, Nemazoline,
2-(2-methyl-benzyl)-4,5-dihydro-1H-imidazole,
2-(2,5-dimethyl-benzyl)-4,5-dihydro-1H-imidazole,
2-(2-trifluoromethyl-benzyl)-4,5-dihydro-1H-imidazole,
2-(3-trifluoromethyl-benzyl)-4,5-dihydro-1H-imidazole,
2-benzyl-4,5-dihydro-1H-imidazole, Priscol, Tolazoline,
rac-2-(1-phenyl-ethyl)-4,5-dihydro-1H-imidazole,
rac-2-(1-phenyl-propyl)-4,5-dihydro-1H-imidazole,
rac-2-[1-(2-chloro-phenyl)-ethyl]-4,5-dihydro-1H-imidazole,
2-(2,5-dimethoxy-benzyl)-4,5-dihydro-1H-imidazole,
4-(4,5-dihydro-1H-imidazol-2-ylmethyl)-phenylamine,
2-(2-chloro-benzyl)-4,5-dihydro-1H-imidazole,
2-(2,4,6-trimethyl-benzyl)-1H-imidazole,
2-(2,6-dimethyl-benzyl)-1H-imidazole,
2-benzyl-1H-imidazole,
2-naphthalen-1-ylmethyl-4,5-dihydro-1H-imidazole, Privine,
2-naphthalen-2-ylmethyl-4,5-dihydro-1H-imidazole,
2-benzofuran-5-ylmethyl-4,5-dihydro-1H-imidazole,
2-benzo[b]thiophen-3-ylmethyl-4,5-dihydro-1H-imidazole,
2-thiophen-2-ylmethyl-4,5-dihydro-1H-imidazole,
2-thiophen-3-ylmethyl-4,5-dihydro-1H-imidazole,
3-(4,5-dihydro-1H-imidazol-2-ylmethyl)-1H-indole,
2-(1-phenyl-propyl)-4,5-dihydro-1H-imidazole,
2-(2-methoxy-benzyl)-1H-imidazole,
2-(2-methoxy-naphthalen-1-ylmethyl)-4,5-dihydro-1H-imidazole,
2-(4-methoxy-naphthalen-1-ylmethyl)-4,5-dihydro-1H-imidazole,
rac-2-(1-naphthalen-1-yl-ethyl)-4,5-dihydro-1H-imidazole,
2-biphenyl-2-ylmethyl-4,5-dihydro-1H-imidazole,
4-methyl-2-naphthalen-1-ylmethyl-4,5-dihydro-1H-imidazole, and
2-(2-methyl-naphthalen-1-ylmethyl)-4,5-dihydro-1H-imidazole and a pharmaceutically acceptable carrier.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an, " and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, 1-butyl, 2-butyl, t-butyl and the like. Preferred alkyl groups are groups with 1-4 carbon atoms.

As used herein, the term "lower alkoxy" denotes a group having an alkyl residue as defined above which is attached via an oxygen atom.

As used herein, the term "cycloalkyl" denotes a saturated carbocyclic hydrocarbon group, containing 3-7 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CF_2CF_3$ and the like.

As used herein, the term "lower alkoxy substituted by halogen" denotes an alkoxy group as defined above, wherein at least one hydrogen atom is replaced by halogen, for example $OCF_3$, $OCHF_2$, $OCH_2F$, $OCH_2CF_3$, $OCH_2CF_2CF_3$ and the like.

As used herein, the term "thiophenyl" is synonymous with "thienyl" and each represents a thiophene substituent, i.e., $C_4H_4S$.

The term "halogen" denotes chlorine, iodine, fluorine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds of formula I for use in the method described above are those, wherein A is phenyl and R is other than hydrogen, for example the following compounds:
2-(2,6-diethyl-benzyl)-4,5-dihydro-1H-imidazole ////
2-(2-ethyl-6-methoxy-benzyl)-4,5-dihydro-1H-imidazole
2-(2-methoxy-6-methyl-benzyl)-4,5-dihydro-1H-imidazole
2-(2-ethyl-6-methyl-benzyl)-4,5-dihydro-1H-imidazole
2-(2-ethyl-6-isopropyl-benzyl)-4,5-dihydro-1H-imidazole
2-(2,3-dichloro-benzyl)-4,5-dihydro-1H-imidazole
rac-2-[1-(2,3-dimethyl-phenyl)-ethyl]-4,5-dihydro-1H-imidazole
2-(3-bromo-2,6-diethyl-benzyl)-4,5-dihydro-1H-imidazole
2-(4-methoxy-2,5-dimethyl-benzyl)-4,5-dihydro-1H-imidazole
2-(2-bromo-4,5-dimethoxy-benzyl)-4,5-dihydro-1H-imidazole
2-(2-ethyl-benzyl)-4,5-dihydro-1H-imidazole
2-(2-chloro-6-methoxy-benzyl)-4,5-dihydro-1H-imidazole
2-(2-cyclopropyl-benzyl)-4,5-dihydro-1H-imidazole
2-(2-bromo-6-methyl-benzyl)-4,5-dihydro-1H-imidazole
2-(3-bromo-5-methoxy-2-methyl-benzyl)-4,5-dihydro-1H-imidazole
2-(2-chloro-3-trifluoromethyl-benzyl)-4,5-dihydro-1H-imidazole
2-(2,6-diethyl-benzyl)-1H-imidazole
2-(2,3,5,6-tetramethyl-benzyl)-1H-imidazole
2-pentamethylphenylmethyl-1H-imidazole
2-(4-methoxy-2,6-dimethyl-benzyl)-1H-imidazole
2-(3-bromo-2,6-diethyl-benzyl)-1H-imidazole
2-(2,6-diethyl-3-tritio-benzyl)-1H-imidazole
2-(4-tert-butyl-2,6-dimethyl-benzyl)-4,5-dihydro-1H-imidazole, Xylometazoline
2-pentamethylphenylmethyl-4,5-dihydro-1H-imidazole
2-(2,3,5,6-tetramethyl-benzyl)-4,5-dihydro-1H-imidazole
6-tert-butyl-3-(4,5-dihydro-1H-imidazol-2-ylmethyl)-2,4-dimethyl-phenol, Oxymethazoline
2-(2,4,6-trimethyl-benzyl)-4,5-dihydro-1H-imidazole, Trimizoline
2-(2,6-dimethyl-benzyl)-4,5-dihydro-1H-imidazole
2-(2,6-dichloro-benzyl)-4,5-dihydro-1H-imidazole
2-(3,4-dichloro-benzyl)-4,5-dihydro-1H-imidazole
2-(2,3-dim ethoxy-benzyl)-4,5-dihydro-1H-imidazole
2-(4-methoxy-2,6-dimethyl-benzyl)-4,5-dihydro-1H-imidazole
2-(2-bromo-benzyl)-4,5-dihydro-1H-imidazole
2,6-dichloro-4-(4,5-dihydro-1H-imidazol-2-ylmethyl)-phenylamine, Nemazoline
2-(2,4,6-trimethyl-benzyl)-1H-imidazole
rac-2-[1-(4-benzyl-phenyl)-ethyl]-4,5-dihydro-1H-imidazole
2-(2-chloro-6-iodo-benzyl)-4,5-dihydro-1H-imidazole
2-(3-chloro-2,6-diethyl-benzyl)-4,5-dihydro-1H-imidazole
2-(3-chloro-2-ethyl-6-fluoro-benzyl)-4,5-dihydro-1H-imidazole
2-(2,6-diethyl-3-fluoro-benzyl)-1H-imidazole
2-(2,6-diethyl-3-methoxy-benzyl)-4,5-dihydro-1H-imidazole
2-(2,6-diethyl-4-methoxy-benzyl)-1H-imidazole
2-(4-ethoxy-2,6-diethyl-benzyl)-1H-imidazole
2-(3-ethoxy-2,6-diethyl-benzyl)-1H-imidazole
2-(3-benzyloxy-2,6-diethyl-benzyl)-1H-imidazole
2-(2,6-diethyl-4-phenoxy-benzyl)-1H-imidazole and
2-(2,6-diethyl-3-phenoxy-benzyl)-1H-imidazole.

Preferred compounds of formula I for use in the method described above are further those, wherein A is naphthyl and R is as described above, for example the following compounds:
2-(4-bromo-naphthalen-1-ylmethyl)-4,5-dihydro-1H-imidazole
4-tritio-2-naphthalen-1-ylmethyl-4,5-dihydro-1H-imidazole
2-naphthalen-1-ylmethyl-4,5-dihydro-1H-imidazole, Privine
2-naphthalen-2-ylmethyl-4,5-dihydro-1H-imidazole
2-(2-methoxy-naphthalen-1-ylmethyl)-4,5-dihydro-1H-imidazole
2-(2-methyl-naphthalen-1-ylmethyl)-4,5-dihydro-1H-imidazole
1-(4,5-dihydro-1H-imidazol-2-ylmethyl)-naphthalen-2-ol and
2-(1-bromo-naphthalen-2-ylmethyl)-4,5-dihydro-1H-imidazole.

Compounds of formula I for as use in the method described above, wherein A is benzofuranyl, are also preferred. Such compounds are
2-(7-methyl-benzofuran-6-ylmethyl)-4,5-dihydro-1H-imidazole
2-(6-methyl-benzofuran-7-ylmethyl)-4,5-dihydro-1H-imidazole
2-benzofuran-7-ylmethyl-4,5-dihydro-1H-imidazole
2-benzofuran-3-ylmethyl-4,5-dihydro-1H-imidazole
2-benzofuran-5-ylmethyl-4,5-dihydro-1H-imidazole
2-benzofuran-4-ylmethyl-4,5-dihydro-1H-imidazole
2-(4-methoxy-benzofuran-5-ylmethyl)-4,5-dihydro-1H-imidazole and
2-benzofuran-6-ylmethyl-4,5-dihydro-1H-imidazole hydrochloride.

Compounds of formula I for use in the method described above, wherein A is thiophenyl, are also preferred. Such compounds are
2-(2,4,5-trimethyl-thiophen-3-ylmethyl)-4,5-dihydro-1H-imidazole
2-(2,4,5-trimethyl-thiophen-3-ylmethyl)-1H-imidazole
2-thiophen-2-ylmethyl-1H-imidazole
2-thiophen-2-ylmethyl-4,5-dihydro-1H-imidazole or
2-thiophen-3-ylmethyl-4,5-dihydro-1H-imidazole.

Compounds of formula I for use in the method described above, wherein A is benzo[b]thiophenyl, are also preferred. One such compound is
2-benzo[b]thiophen-3-ylmethyl-4,5-dihydro-1H-imidazole.

Compounds of formula I for use in the method described above, wherein hetaryl is indol-3-yl are also preferred. One such compounds is
3-(4,5-dihydro-1H-imidazol-2-ylmethyl)-1H-indole.

Preferred novel compounds are the following:

Compounds of formula I, wherein A is phenyl and R is other than hydrogen, for example the following compounds
2-(2,6-diethyl-benzyl)-4,5-dihydro-1H-imidazole
2-(2-ethyl-6-methoxy-benzyl)-4,5-dihydro-1H-imidazole
2-(2-methoxy-6-methyl-benzyl)-4,5-dihydro-1H-imidazole
2-(2-ethyl-6-methyl-benzyl)-4,5-dihydro-1H-imidazole
2-(2-ethyl-6-isopropyl-benzyl)-4,5-dihydro-1H-imidazole
2-(2,3-dichloro-benzyl)-4,5-dihydro-1H-imidazole
rac-2-[1-(2,3-dimethyl-phenyl)-ethyl]-4,5-dihydro-1H-imidazole
2-(3-bromo-2,6-diethyl-benzyl)-4,5-dihydro-1H-imidazole
2-(4-methoxy-2,5-dimethyl-benzyl)-4,5-dihydro-1H-imidazole
2-(2-bromo-4,5-dimethoxy-benzyl)-4,5-dihydro-1H-imidazole
2-(2-ethyl-benzyl)-4,5-dihydro-1H-imidazole
2-(2-chloro-6-methoxy-benzyl)-4,5-dihydro-1H-imidazole
2-(2-cyclopropyl-benzyl)-4,5-dihydro-1H-imidazole
2-(2-bromo-6-methyl-benzyl)-4,5-dihydro-1H-imidazole
2-(3-bromo-5-methoxy-2-methyl-benzyl)-4,5-dihydro-1H-imidazole
2-(2-chloro-3-trifluoromethyl-benzyl)-4,5-dihydro-1H-imidazole
2-(2,6-diethyl-benzyl)-1H-imidazole
2-(2,3,5,6-tetramethyl-benzyl)-1H-imidazole
2-pentamethylphenylmethyl-1H-imidazole
2-(4-methoxy-2,6-dimethyl-benzyl)-1H-imidazole
2-(3-bromo-2,6-diethyl-benzyl)-1H-imidazole
2-(2,6-diethyl-3-tritio-benzyl)-1H-imidazole
rac-2-[1-(4-benzyl-phenyl)-ethyl]-4,5-dihydro-1H-imidazole
2-(2-chloro-6-iodo-benzyl)-4,5-dihydro-1H-imidazole
2-(3-chloro-2,6-diethyl-benzyl)-4,5-dihydro-1H-imidazole
2-(3-chloro-2-ethyl-6-fluoro-benzyl)-4,5-dihydro-1H-imidazole
2-(2,6-diethyl-3-fluoro-benzyl)-1H-imidazole
2-(2,6-diethyl-3-methoxy-benzyl)-4,5-dihydro-1H-imidazole
2-(2,6-diethyl-4-methoxy-benzyl)-1H-imidazole
2-(4-ethoxy-2,6-diethyl-benzyl)-1H-imidazole
2-(3-ethoxy-2,6-diethyl-benzyl)-1H-imidazole
2-(3-benzyloxy-2,6-diethyl-benzyl)-1H-imidazole
2-(2,6-diethyl-4-phenoxy-benzyl)-1H-imidazole and
2-(2,6-diethyl-3-phenoxy-benzyl)-1H-imidazole.

Compounds of formula I, wherein A is naphthyl and R is as described above, for example
2-(4-bromo-naphthalen-1-ylmethyl)-4,5-dihydro-1H-imidazole
4-tritio-2-naphthalen-1-ylmethyl-4,5-dihydro-1H-imidazole
1-(4,5-dihydro-1H-imidazol-2-ylmethyl)-naphthalen-2-ol and
2-(1-bromo-naphthalen-2-ylmethyl)-4,5-dihydro-1H-imidazole.

Compounds of formula I, wherein A is benzofuranyl, for example
2-(7-methyl-benzofuran-6-ylmethyl)-4,5-dihydro-1H-imidazole
2-(6-methyl-benzofuran-7-ylmethyl)-4,5-dihydro-1H-imidazole
2-benzofuran-7-ylmethyl-4,5-dihydro-1H-imidazole
2-benzofuran-3-ylmethyl-4,5-dihydro-1H-imidazole
2-benzofuran-4-ylmethyl-4,5-dihydro-1H-imidazole
2-(4-methoxy-benzofuran-5-ylmethyl)-4,5-dihydro-1H-imidazole and
2-benzofuran-6-ylmethyl-4,5-dihydro-1H-imidazole.

Compounds of formula I, wherein A is thiophenyl, for example
2-(2,4,5-trimethyl-thiophen-3-ylmethyl)-4,5-dihydro-1H-imidazole
2-(2,4,5-trimethyl-thiophen-3-ylmethyl)-1H-imidazole and
2-thiophen-2-ylmethyl-1H-imidazole.

The aryl or hetaryl substituted 2-imidazoles or imidazolines described in formula I of the present invention can be prepared in analogy to literature procedures following the pathways depicted in process steps a), b), c) and d) and in Schemes 1 to 8.

These procedures are described in following references:
[1] *Tetrahedron Letters* 1993, 34, 3255;
[2] *Liebigs Ann. Chem.* 1980, 2061;
[3] *Tetrahedron* 2002, 58, 9925;
[4] *Tetrahedron* 2004, 60, 9857;
[5] *J. Med. Chem.* 1998, 41, 2243;
[6] *J. Med. Chem.* 1986, 29, 1413;
[7] *Bull. Korean Chem. Soc.* 2003, 24, 1354;
[8] *J. Med. Chem.* 1987, 30, 1482;
[9] *Eur. J. Med. Chem.* 1991, 26, 207;
[10] *Bioorg. Med. Chem. Lett.* 2004, 14, 6079 and *Heterocycles* 1995, 40, 841;
[11] *Synth. Commun.* 1990, 20, 2483;
[12] *Chem. Pharm. Bull.* 1987, 35, 1058 and Synthesis 1990, 78;
[13] *Synlett* 1992, 647;
[14] *J. Org. Chem.* 1978, 43, 2480;
[15] *Synlett* 2004, 2803-2805;
[16] *Synthesis* 1999, 2138-2144;
[17] *Tetrahedron Lett.* 1998, 39, 2937-2940;
[18] *J. Chem. Soc., Perkin Trans.* 1 2002, 1061-1066.

The present compounds of formula I and their pharmaceutically acceptable salts can be prepared by methods known in the art, for example, by processes described below, which processes comprise a) reacting a compound of formula

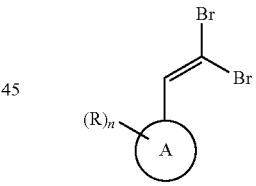

III with ethylenediamine of formula

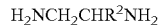

$H_2NCH_2CHR^2NH_2$    II to obtain a compound of formula

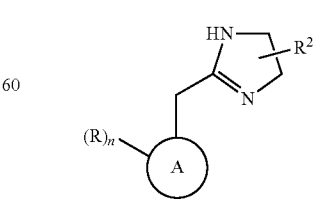

I-1 wherein R, $R^2$, aryl, hetaryl and n are as defined above, or b) reacting a compound of formula

[Structure showing R¹-CH(CN) attached to ring A with (R)ₙ substituents]

with ethylenediamine of formula $$H_2NCH_2CHR^2NH_2 \qquad II$$

to obtain a compound of formula I-2

[Structure of imidazoline I-2 with R¹, R², (R)ₙ, A]

wherein the substituents are as defined above, or c) reacting a solution of a compound of formula I-2

[Structure of imidazoline I-2]

with DMSO and oxalyl chloride in dichloromethane or potassium permanganate absorbed on silica gel in acetonitrile or with Pd/C in toluene to obtain a compound of formula I-3

[Structure of imidazole I-3]

wherein the substituents are as defined above, or d) reducing a compound of formula

[Structure with HO group, R¹, imidazole with R², and ring A with (R)ₙ]

to obtain a compound of formula V

[Structure of compound V with R¹, R², imidazole-NH, ring A with (R)ₙ]

wherein R¹ is hydrogen or lower alkyl and the other substituents are as defined above, and if desired, converting the compounds obtained into pharmaceutically acceptable acid addition salts.

The aryl or hetaryl substituted 2-imidazoles or imidazolines of the invention can be prepared in analogy to literature procedures following the pathways depicted in Scheme 1 to 8. The starting materials are either commercially available, are otherwise known in the chemical literature, or can be prepared in accordance with methods well known in the art.

Procedure A

Scheme 1
Synthesis of imidazolines and imidazoles of formula I
wherein R¹ = hydrogen

[Scheme showing:
IV: aldehyde (R)ₙ-A-CHO
→ Ph₃P, CBr₄, CH₂Cl₂ <5° C. [2, 3]
III: (R)ₙ-A-CH=CBr₂
→ H₂NCH₂CHR²NH₂ (II), CH₂Cl₂ r.t.
I-1: imidazoline (R)ₙ-A-CH₂-imidazoline with R², NH
→ DMSO, (COCl)₂, NEt₃, CH₂Cl₂, −78° C. [14]
or TCCA, DBU, MeCN [15]
I-3-1: imidazole (R)ₙ-A-CH₂-imidazole with R², NH]

The 2-imidazoles of formula I-3-1 can be synthesized from the corresponding 2-imidazolines of formula I-1 by oxidation as depicted in Scheme 1. Suitable reagents for this transformation include an oxidant which is prepared in situ from dimethylsulfoxide (DMSO) and oxalyl chloride, according to the procedure of Swern et al. [14]. The reaction is carried out in a halogenated solvent, preferably dichloromethane, at low temperature, preferably at a temperature between −78° C. and −60° C. The reaction is completed by treatment with an organic base such as triethylamine followed by warming to room temperature.

An alternative procedure by which the oxidation of imidazolines I-1 to imidazoles I-3-1 can be accomplished is treatment with trichloroisocyanuric acid (TCCA) and 1,8-diazabicyclo[5.4.0]undec-7-ene (DBU) [15]. This reaction is carried out in an aprotic polar solvent, preferably acetonitrile, at a temperature between −20° C. and +30° C., preferably room temperature.

The 2-imidazolines of formula I-1 can in turn be synthesized from an aldehyde of formula IV in two steps as depicted in Scheme 1. In the first step the aldehyde IV is treated at ambient temperature with a reagent prepared in situ from tetrabromomethane and triphenylphosphine in an organic solvent, preferably dichloromethane, below ambient temperature, usually between 0° C. and 10° C. In the second step the resulting 1,1-dibromovinyl derivative of formula III is reacted with ethylenediamine, or a derivative thereof bearing an additional substituent $R^2$, in dichloromethane at ambient temperature.

The compounds of formula III are new compounds, prepared from the corresponding aldehydes of formula IV. The aldehydes IV are either commercially available or described in the literature or accessible in analogy to syntheses described in the literature. Synthesis of aldehydes not reported in the literature and/or not available from a commercial source is described in schemes 2 and 3.

Preparation of the Starting Material (Aldehyde IV)

Starting aryl aldehydes or heteroaryl aldehydes of formula IV bearing substituents R" and R'" in ortho and ortho' position relative to the aldehyde functionality can be synthesized following a published reaction sequence depicted in Scheme 2 [1]. The starting material is an ortho,ortho'-dialkoxy-aryl aldehyde or ortho,ortho'-dialkoxy-heteroaryl aldehyde.

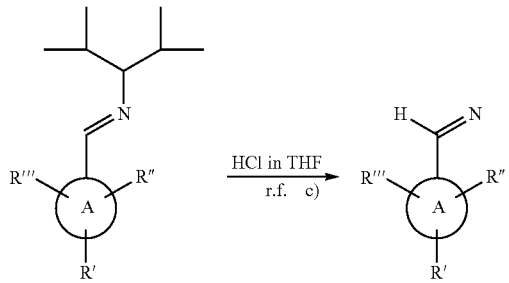

a) pTsOH, toluene, rf, 40 min,
b) 1.1 eq. R"Li, THF, -10° C., 2 h, followed by treatment with R'''Li, or in case of R" = R'" 2,3 eq. of the corresponding Li-compound, THF, -10° C., 2h,
c) 4M aq. HCl in THF, rf, 2-4 h.
R', R" and R'" are lower alkyl, cycloalkyl or phenyl. The substituents R" and R'" are always in the ortho and ortho' position on the aryl or heteroaryl ring relative to the aldehyde functionality.

Alternative Preparation of the Starting Material (Aldehyde IV)

Starting aryl aldehydes or heteroaryl aldehydes of formula IV bearing substituents R" and R'" in ortho and ortho' position relative to the aldehyde functionality can also be synthesized following a published reaction sequence depicted in Scheme 3 [16]. The starting material is an ortho,ortho'-dihalo-aryl aldehyde or ortho,ortho'-dihalo-heteroaryl aldehyde, where the halogen atoms present are either chloro or fluoro. The starting aldehyde is first transformed to the corresponding N-butyl imine derivative, by treatment with N-butylamine and p-toluenesulphonic acid in toluene at reflux. The two halogen substituents can then each in turn be displaced by an alkyl or aryl Grignard reagent of formula R"MgX and R'"MgX in the presence of manganese(II) chloride. The reaction is carried out in an ethereal solvent, preferably tetrahydrofuran, at a temperature between 0° C. and the reflux temperature of the solvent. Following this reaction, the imine can be hydrolysed to afford the corresponding aldehyde of formula IV. The hydrolysis can be accomplished by treatment with an aqueous acid, such as aqueous sulphuric acid or aqueous hydrochloric acid, at elevated temperature, or can also occur during chromatography of the imine on silica gel.

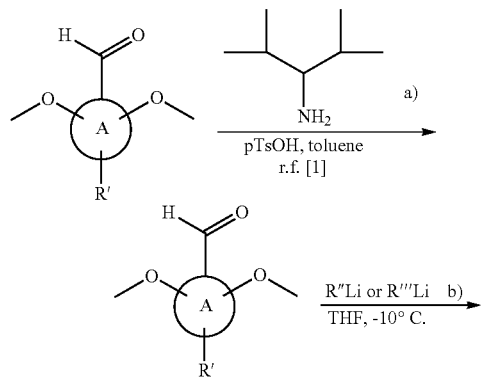

Scheme 2

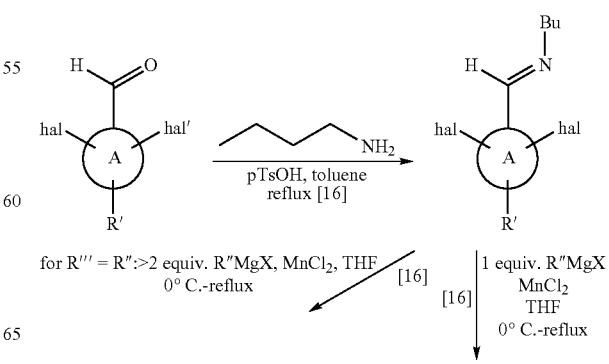

Scheme 3

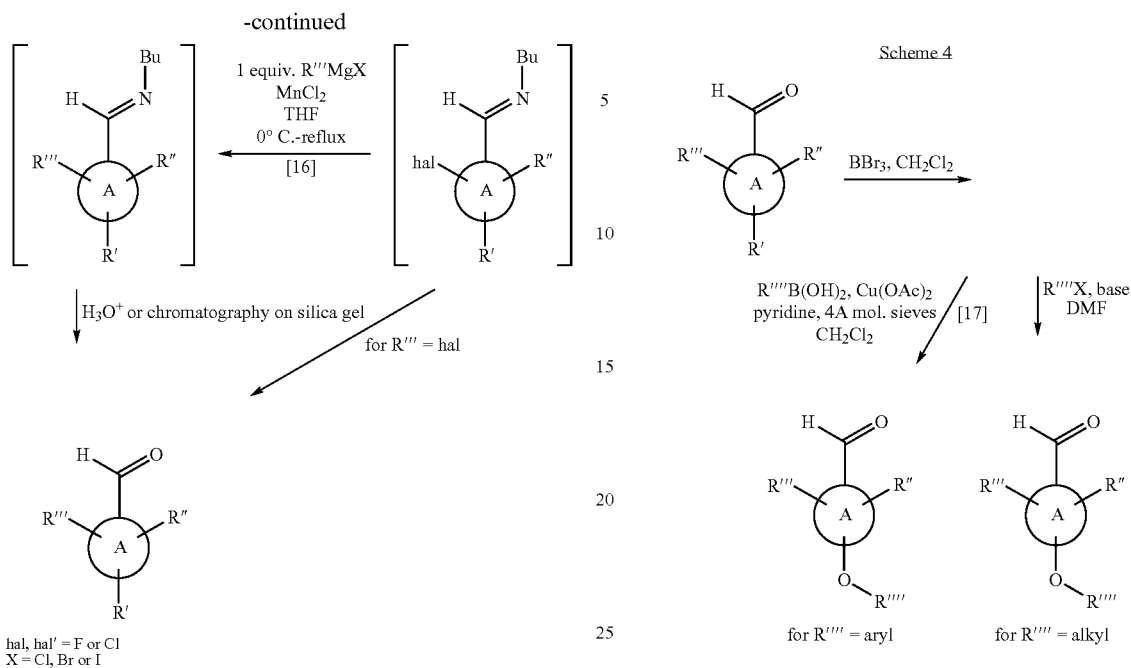

hal, hal' = F or Cl
X = Cl, Br or I

R' is lower alkyl, cycloalkyl, lower alkoxy, halogen or phenyl, R" and R''' are lower alkyl, cycloalkyl or phenyl. The substituents R" and R''' are always in the ortho and ortho' position on the aryl or heteroaryl ring relative to the aldehyde functionality.

Alternative Preparation of the Starting Material (Aldehyde IV)

Starting aryl aldehydes or heteroaryl aldehydes of formula IV bearing alkoxy or aryloxy substituents can be prepared by the reaction sequence depicted in Scheme 4. The starting material is the corresponding hydroxy-aryl aldehyde or hydroxy-heteroaryl aldehyde, or, where these compounds are not available, the corresponding methoxy-aryl aldehyde or methoxy-heteroaryl aldehyde can be used. The methoxy-aryl aldehyde or methoxy-heteroaryl aldehyde can be transformed to the corresponding hydroxy-aryl aldehyde or hydroxy-heteroaryl aldehyde by treatment with a Lewis acid such as boron tribromide in an inert solvent such as dichloromethane. The resulting free hydroxyl group can then be alkylated by treatment with a base, preferably cesium carbonate, and an alkylating agent such as an alkyl halide, in an aprotic polar solvent such as N,N-dimethylformamide, so as to afford the desired alkoxy-aryl aldehyde or alkoxy-heteroaryl aldehyde. Alternatively, aryloxy-aryl aldehydes or aryloxy-heteroaryl aldehydes can be obtained by reaction of the corresponding hydroxy-aryl aldehyde or hydroxy-heteroaryl aldehyde with an aryl boronic acid in the presence of copper(II) acetate, pyridine and 4 Å molecular sieves according to the procedure of Evans et al. [17]. This reaction is carried out in a halogenated organic solvent such as dichloromethane, preferably at room temperature.

R" and R''' are lower alkyl, cycloalkyl or phenyl. The substituents R" and R''' are always in the ortho and ortho' position on the aryl or heteroaryl ring relative to the aldehyde functionality.

Procedure B

Preparation of Compounds of Formula I Wherein $R^1$=Lower Alkyl

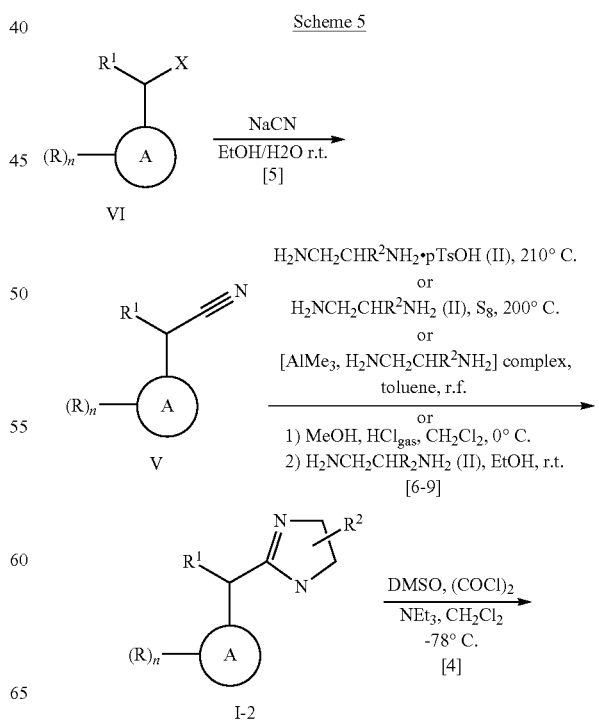

-continued

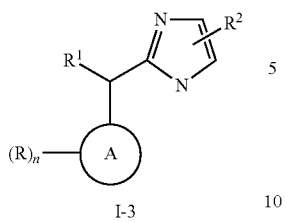

I-3 wherein X is halogen and the other definitions are as described above.

2-Imidazolines of formula I-2 can be prepared by reaction of a nitrile of formula V with ethylenediamine or a derivative thereof bearing an additional substituent $R^2$ as depicted in Scheme 5. This cyclization with a diamine II can be conducted by heating a diamine mono p-toluenesulfonic acid salt with a nitrile in the absence of additional solvent at a temperature between 100° C. and 250° C., preferably between 140° C. and 240° C., for several hours, preferably 2 to 6 hours, or by heating a solution of the nitrile in an excess of ethylenediamine or a derivative thereof ($R^2$=lower alkyl) in the presence of a catalytic amount of sulfur, preferably 10% to 50%, in a sealed tube under microwave irradiation at 200° C. for 10 to 60 minutes, preferred 15 to 30 minutes, or by reaction of a complex preformed from trimethylaluminum and ethylenediamine or a derivative thereof ($R^2$=lower alkyl) in toluene below ambient temperature, preferably at 0° C. to 10° C., with a nitrile in toluene at reflux temperature for 4 to 24 hours, preferably for 16 to 20 hours.

2-Imidazolines of formula I-2 can also be prepared by treatment of a nitrile V dissolved in an inert solvent like dichloromethane and a lower alcohol, preferably methanol or ethanol, with hydrogen chloride gas in a Pinner type reaction which provides an imidate. Reaction of this product with ethylenediamine or a derivative thereof in an alcohol, preferably methanol or ethanol, at ambient temperature for 16 to 24 hours leads to the 2-imidazoline.

The nitrites of formula V are prepared from aryl or hetaryl halides of formula VI by substitution with cyanide following literature procedures. Synthesis of nitriles not reported in the literature and/or not available from a commercial source is described below.

Procedure C

Preparation of Imidazoles by Dehydrogenation of Imidazolines

Scheme 6

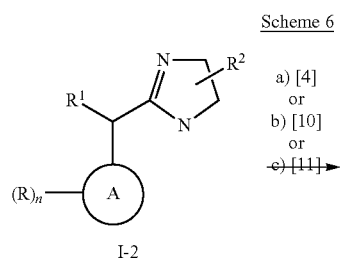

-continued

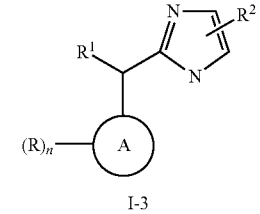

I-3 a) 1. DMSO, (COCl)$_2$, CH$_2$Cl$_2$, -78° C., 20 to 30 min., then addition of imidazoline in CH$_2$Cl$_2$, -78° C., 50 min., 2. NEt$_3$, warming up to rt;
b) KMnO$_4$ on silica gel, MeCN, rt, 16 h;
c) 10% Pd/C, toluene, rt, 88 h;

The 2-imidazoles of formula I-3 are prepared by dehydrogenation of the corresponding 2-imidazolines of formula I-2 as depicted in Scheme 6. Three procedures described in the literature have been used for this transformation, the Swern type oxidation (a), oxidation by potassium permanganate (b), and catalytic dehydrogenation (c).

Procedure D

Preparation of Imidazoles by Addition of an N-protected Imidazole

Scheme 7

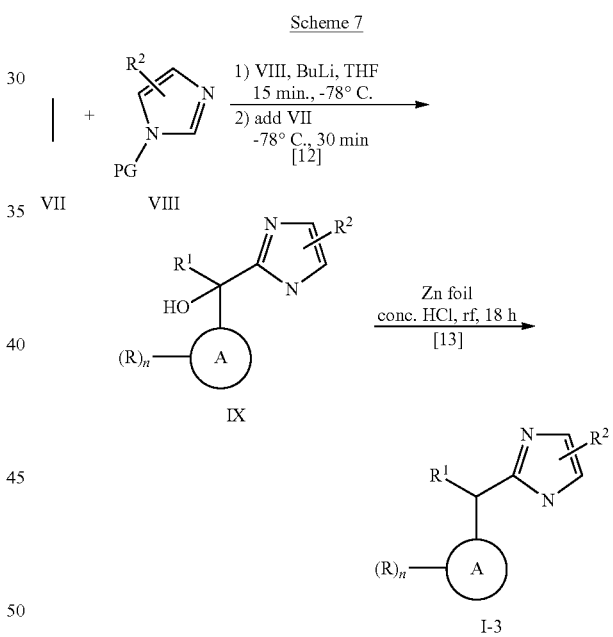

PG is a protecting group such as CH(OEt)$_2$ wherein $R^1$ is hydrogen or lower alkyl and the remaining substituents are as described above.

The 2-imidazoles of formula I-3 can also be prepared as depicted in Scheme 7. Direct introduction of the 2-imidazole can be achieved by reaction of an aryl/hetaryl aldehyde or ketone of formula VII with a metallated, preferably the lithium derivative, N-protected imidazole of formula VIII which is deprotonated with a strong base like alkyl or aryl lithium, preferably by n-butyl lithium, in an inert organic solvent, e.g. tetrahydrofuran or diethyl ether, below ambient temperature, preferably at −78° C. The N-protecting group can be removed after the reaction is complete, for instance the —CH(OEt)$_2$ protecting group is cleaved during the aqueous work-up of the reaction. The resulting alcohol of formula IX can be reduced by a Clemmensen type reduction with zinc foil as reductive agent in concentrated aqueous hydrochloric acid at reflux temperature for 16 to 24 h. An alternative procedure for the reduction of alcohols of formula IX involves treatment with triethylsilane and trifluoroacetic acid in a halogenated solvent such as dichloromethane or 1,2-dichloroethane [18]. The reaction can be carried out at room temperature or at elevated temperature, and is preferably performed in a sealed tube in order that the reaction mixture can be heated to temperatures above the boiling point of the solvent used, preferably to 100° C.

Procedure E

Preparation of Pyrazole Derivatives

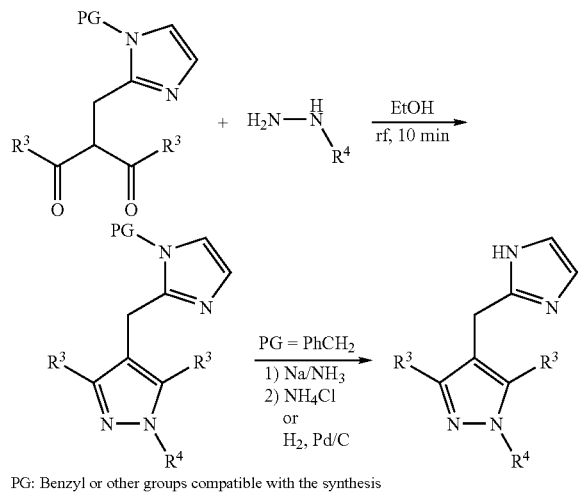

PG: Benzyl or other groups compatible with the synthesis
$R^3$: alkyl
$R^4$: H, alkyl Pyrazole derivatives can be prepared by condensation of a β-dicarbonyl compound bearing at the α-carbon a 1-benzyl-1H-imidazol-2-ylmethyl residue with an appropriate hydrazine derivative. Debenzylation of the resulting pyrazole derivative is performed either by catalytic hydrogenation or with sodium in liquid ammonia. The β-dicarbonyl compounds can be prepared following procedures well known in the art.

Preparation of Tritiated Derivatives

Compounds of formula I, wherein R is tritium can be prepared from the corresponding halogenated (chloro, bromo or iodo) compound, preferred is the bromo-substituted compound, by catalytic hydrogenation with tritium gas.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 μM). Competing ligands were tested in a wide range of concentrations (10 pM-30 μM). The final dimethylsulphoxide concentration in the assay was 2%, and it did not affect radioligand binding. Each experiment was performed in duplicate. Al incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse on TAAR1 in the range of 0.005-0.050. Values for representative compounds are shown in the table below.

| Example | Ki (μM) mouse | Example | Ki | Example | Ki |
|---|---|---|---|---|---|
| 1 | 0.007 | 107 | 0.022 | 158 | 0.021 |
| 9 | 0.010 | 109 | 0.004 | 168 | 0.045 |
| 10 | 0.023 | 110 | 0.021 | 169 | 0.045 |
| 11 | 0.007 | 112 | 0.025 | 170 | 0.026 |
| 12 | 0.030 | 113 | 0.007 | 172 | 0.050 |
| 17 | 0.021 | 114 | 0.006 | 175 | 0.011 |
| 18 | 0.027 | 115 | 0.007 | 187 | 0.016 |
| 32 | 0.005 | 116 | 0.008 | 196 | 0.023 |
| 33 | 0.014 | 117 | 0.008 | 198 | 0.036 |
| 34 | 0.031 | 118 | 0.017 | 202 | 0.034 |
| 54 | 0.016 | 119 | 0.021 | 206 | 0.038 |
| 55 | 0.017 | 120 | 0.022 | 210 | 0.048 |
| 56 | 0.025 | 121 | 0.023 | 215 | 0.029 |
| 57 | 0.029 | 122 | 0.025 | 217 | 0.024 |
| 58 | 0.030 | 123 | 0.028 | 218 | 0.047 |
| 59 | 0.041 | 124 | 0.044 | 219 | 0.012 |
| 70 | 0.025 | 125 | 0.048 | 220 | 0.013 |
| 71 | 0.010 | 137 | 0.038 | | |
| 72 | 0.017 | 140 | 0.007 | | |
| 73 | 0.049 | 141 | 0.029 | | |
| 77 | 0.026 | 143 | 0.004 | | |
| 104 | 0.008 | 149 | 0.012 | | |
| 106 | 0.017 | 154 | 0.010 | | |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD). Therefore, the invention provides a method for treating depression which comprises administering to an individual a therapeutically effective amount of a compound of the invention. The invention also provides a method for treating psychosis which comprises administering to an individual a therapeutically effective amount of a compound of the invention. The invention provides a method for treating Parkinson's disease which comprises administering to an individual a therapeutically effective amount of a compound of the invention. The invention provides a method for treating anxiety which comprises administering to an individual a therapeutically effective amount of a compound of the invention. The invention further provides a method for treating ADHD which comprises administering to an individual a therapeutically effective amount of a compound of the invention.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Procedure A

Example 1

2-(2,6-Diethyl-benzyl)-4,5-dihydro-1H-imidazole

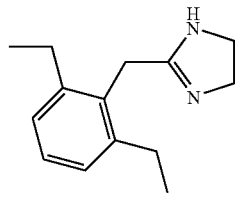

a) [1-(2,6-Dimethoxy-phenyl)-meth-(E)-ylidene]-(1-isopropyl-2-methyl-propyl)-amine

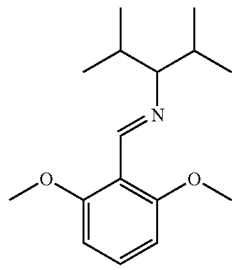

A mixture of 25.0 g (150 mmol) 2,6-dimethoxybenzaldehyde, 19.1 g (165 mmol) 3-amino-2,4-dimethylpentane and 0.500 g p-toluenesulfonic acid in 100 ml toluene was heated in a Dean-Stark apparatus to reflux for 2 hours. Then the cooled reaction mixture was washed with aqueous $NaHCO_3$ solution, brine dried over $Na_2SO_4$, filtered and evaporated. The crude product was filtered through a silica pad with heptane/ethyl acetate 2:1 as eluent: 22.0 g [1-(2,6-dimethoxy-phenyl)-meth-(E)-ylidene]-(1-isopropyl-2-methyl-propyl)-amine as slightly yellow crystals: MS (EI): 264.3 $((M+H)^{+\cdot})$, 262.3 $((M-H)^{+\cdot})$, 248.3 $((M-CH_3)^{+\cdot})$, 220.2 $((M-(CH_3)_2CH)^{+\cdot}, 100\%)$.

b) (E)-[1-(2,6-Diethyl-phenyl)-methylidene]-(1-isopropyl-2-methyl-propyl)-amine

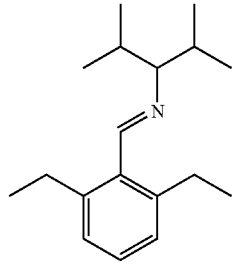

To a solution of 16.0 g (61 mmol) [1-(2,6-dimethoxy-phenyl)-meth-(E)-ylidene]-(1-isopropyl-2-methyl-propyl)-amine in 80 ml dry THF cooled to −40° C. were added 364 ml of a 0.5M solution of ethyl lithium in cyclohexane/benzene drop-wise to keep temperature below −20° C. Then the mixture was stirred at −20° C. for further 30 min and the reaction quenched by addition of water. The aqueous phase was extracted with ethyl acetate, the combined extracts washed with brine, dried over Na$_2$SO$_4$, filtered and evaporated: 15.6 g (E)-[1-(2,6-diethyl-phenyl)-methylidene]-(1-isopropyl-2-methyl-propyl)-amine as colourless liquid: MS (EI): 259.2 (M$^+$), 216.3 ((M-(CH$_3$)$_2$CH)$^+$)), 160.1 (((M-(((CH$_3$)$_2$CH)$_2$CH))$^+$), 100%).

c) 2,6-Diethyl-benzaldehyde

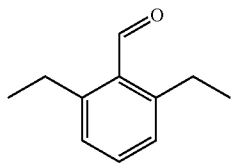

A solution of 15.6 g (E)-[1-(2,6-diethyl-phenyl)-methylidene]-(1-isopropyl-2-methyl-propyl)-amine in 60 ml THF and 120 ml 4N HCl was heated to reflux for 2 hours then cooled to ambient temperature and poured onto a 1N NaOH solution. The aqueous phase was extracted with ethyl acetate, the combined extracts washed with brine, dried over Na$_2$SO$_4$, filtered and evaporated. The residue was purified by flash-chromatography on silica gel with a heptane/ethyl acetate gradient as eluent: 8.35 g 2,6-diethyl-benzaldehyde as light yellow oil: MS (EI): 162.1 (M$^+$, 100%).

d) 2-(2,2-Dibromo-vinyl)-1,3-diethyl-benzene

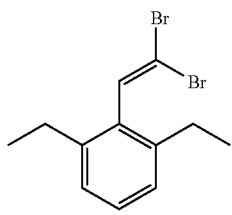

To a solution of 3.80 g (23.4 mmol) 2,6-diethyl-benzaldehyde and 12.3 g (47 mmol) triphenylphosphine in 100 ml dry dichloromethane cooled to −20° C. was added drop-wise a solution of 9.32 g (28.1 mmol) tetrabromomethane in 70 ml dichloromethane. The reaction temperature was kept below 5° C. After the addition the reaction mixture was kept at −10° C. for 5 minutes and then for 30 minutes at ambient temperature. The reaction mixture was poured onto water, extracted with ethyl acetate, the combined extracts washed with brine, dried over Na$_2$SO$_4$, filtered and evaporated. The residue was purified by flash-chromatography on silica gel with a heptane/ethyl acetate gradient as eluent: 4.50 g 2-(2,2-dibromo-vinyl)-1,3-diethyl-benzene as colourless liquid: MS (EI): 319.9 and 318.0 and 316.0 (M$^+$), 239.1 and 237.1 ((M-Br)$^+$), 158.2 ((M-Br$_2$)$^+$, 100%).

e) 2-(2,6-Diethyl-benzyl)-4,5-dihydro-1H-imidazole

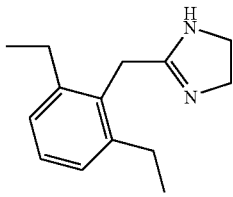

To 20 ml ethylene diamine were added at 0° C. 3.20 g (10 mmol) 2-(2,2-dibromo-vinyl)-1,3-diethyl-benzene and the mixture stirred at ambient temperature for 16 hours. The reaction was quenched by addition of aqueous 2N ammonia, extracted with ethyl acetate, the combined extracts washed with brine, dried over Na$_2$SO$_4$, filtered and evaporated. The residue was dissolved in ethyl acetate and crystallization at −10° C. provided 2.85 g 2-(2,6-diethyl-benzyl)-4,5-dihydro-1H-imidazole as colourless solid: MS (ISP): 217.1 ((M+H)$^+$).

In analogy to Example 1 were prepared Examples 2 to 16:

Example 2 rac-2-(2,6-Diethyl-benzyl)-4-methyl-4,5-dihydro-1H-imidazole or tautomer

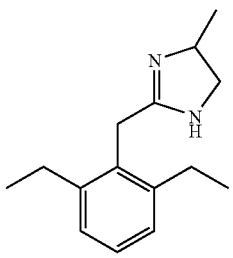

rac-2-(2,6-Diethyl-benzyl)-4-methyl-4,5-dihydro-1H-imidazole was prepared from 2-(2,2-dibromo-vinyl)-1,3-diethyl-benzene and 1,2-diaminopropane in analogy to Example 1 e): orange crystals; MS (EI): 230.2 (M$^+$), 215.2 ((M-CH$_3$)$^+$), 201.2 (((M-CH$_3$CH$_2$)$^+$), 100%).

Example 3

2-(2,6-Dimethoxy-benzyl)-4,5-dihydro-1H-imidazole a) 2-(2,2-Dibromo-vinyl)-1,3-dimethoxy-benzene

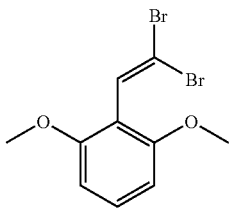

2-(2,2-Dibromo-vinyl)-1,3-dimethoxy-benzene was prepared from 2,6-dimethoxy-benzaldehyde in analogy to Example 1d): colourless liquid.

b) 2-(2,6-Dimethoxy-benzyl)-4,5-dihydro-1H-imidazole

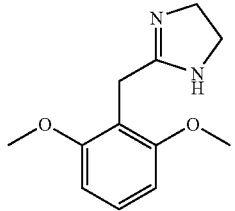

2-(2,6-Dimethoxy-benzyl)-4,5-dihydro-1H-imidazole was prepared from 2-(2,2-dibromo-vinyl)-1,3-dimethoxy-benzene in analogy to Example 1e): light yellow crystals; MS (EI): 220.0 (M$^{+\cdot}$), 189.1 ((M-OCH$_3$)$^{+\cdot}$, 100%).

Example 4

2-(2,6-Diisopropyl-benzyl)-4,5-dihydro-1H-imidazole a) 2-(2,2-Dibromo-vinyl)-1,3-diisopropyl-benzene

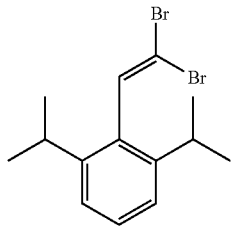

2-(2,2-Dibromo-vinyl)-1,3-diisopropyl-benzene was prepared from 2,6-diisopropyl-benzaldehyde in analogy to Example 1d): light yellow liquid; MS (EI): 348.0 and 346.0 and 344.0 (M$^{+\cdot}$), 265.1 ((M-Br)$^{+\cdot}$), 186.2 (((M-2Br)$^{+\cdot}$), 100%).

b) 2-(2,6-Diisopropyl-benzyl)-4,5-dihydro-1H-imidazole

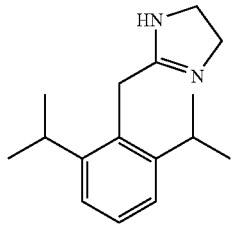

2-(2,6-Diisopropyl-benzyl)-4,5-dihydro-1H-imidazole was prepared from 2-(2,2-Dibromo-vinyl)-1,3-diisopropyl-benzene in analogy to Example 1e): colourless solid: MS (ISP): 245.1 ((M+H)$^{+\cdot}$).

Example 5

2-(2,6-Diisobutyl-benzyl)-4,5-dihydro-1H-imidazole a) 2,6-Diisobutyl-benzaldehyde

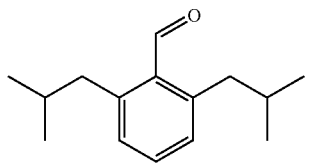

2,6-Diisobutyl-benzaldehyde was prepared from [1-(2,6-dimethoxy-phenyl)-meth-(E)-ylidene]-(1-isopropyl-2-methyl-propyl)-amine and isobutyl lithium in analogy to Example 1b) followed by hydrolysis of the intermediate in analogy to Example 1c): light yellow liquid; MS (EI): 218.2 (M$^{+\cdot}$), 200.2 ((M-H$_2$O)$^{+\cdot}$), 185.2 ((M-(H$_2$O+CH$_3$))$^{+\cdot}$), 161.1 (((M-(C$_4$H$_9$))$^{+\cdot}$), 100%).

b) 2-(2,2-Dibromo-vinyl)-1,3-diisobutyl-benzene

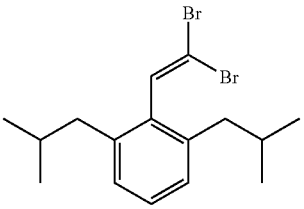

2-(2,2-Dibromo-vinyl)-1,3-diisobutyl-benzene was prepared from 2,6-diisobutyl-benzaldehyde in analogy to Example 1d): colourless liquid; MS (EI): 376.0 and 374.0 and 372.0 (M$^{+\cdot}$), 157.1 ((M-(2Br+CH$_3$+C$_3$H$_6$))$^{+\cdot}$, 100%).

c) 2-(2,6-Diisobutyl-benzyl)-4,5-dihydro-1H-imidazole

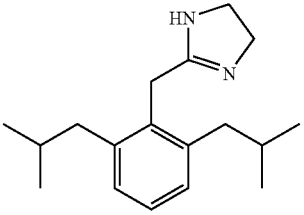

2-(2,6-Diisobutyl-benzyl)-4,5-dihydro-1H-imidazole was prepared from 2-(2,2-Dibromo-vinyl)-1,3-diisobutyl-benzene in analogy to Example 1e): yellow oil; MS (ISP): 273.1 ((M+H)$^{+\cdot}$).

Example 6 rac-2-(2,6-Di-sec-butyl-benzyl)-4,5-dihydro-1H-imidazole a) rac-2,6-Di-sec-butyl-benzaldehyde

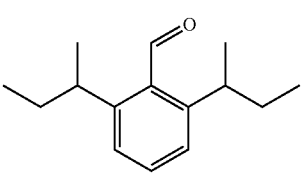

rac-2,6-Di-sec-butyl-benzaldehyde was prepared from [1-(2,6-dimethoxy-phenyl)-meth-(E)-ylidene]-(1-isopropyl-2-methyl-propyl)-amine and sec-butyl lithium in analogy to Example 1b) followed by hydrolysis of the intermediate in analogy to Example 1c): colourless oil; MS (EI): 218.2 (M$^{+\cdot}$), 189.1 ((M-C$_2$H$_5$)$^{+\cdot}$), 171.1 ((M-(C$_2$H$_5$+H$_2$O))$^{+\cdot}$, 100%).

b) rac-1,3-Di-sec-butyl-2-(2,2-dibromo-vinyl)-benzene

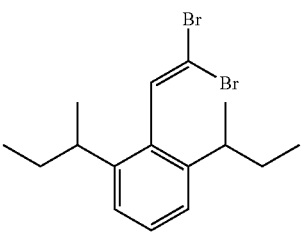

rac-1,3-Di-sec-butyl-2-(2,2-dibromo-vinyl)-benzene benzene was prepared from rac-2,6-di-sec-butyl-benzaldehyde in analogy to Example 1d): colourless liquid; MS (EI): 376.1 and 374.0 and 372.0 (M$^{+\cdot}$), 346.9 and 345.0 and 343.0 ((M-(CH$_3$CH$_2$))$^{+\cdot}$), 295.1 and 293.1 ((M-Br)$^{+\cdot}$), 214.2 (((M-2Br)$^{+\cdot}$), 100%).

c) rac-2-(2,6-Di-sec-butyl-benzyl)-4,5-dihydro-1H-imidazole

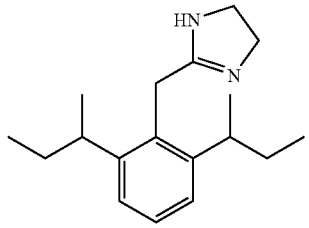

rac-2-(2,6-Di-sec-butyl-benzyl)-4,5-dihydro-1H-imidazole was prepared from rac-1,3-di-sec-butyl-2-(2,2-dibromo-vinyl)-benzene in analogy to Example 1e): colourless crystals; MS (EI): 272.3 (M$^{+\cdot}$), 257.2 ((M-CH$_3$)$^{+\cdot}$), 243.2 ((M-CH$_3$CH$_2$)$^{+\cdot}$), 215.2 ((M-(CH$_3$CH$_2$+C$_2$H$_4$))$^{+\cdot}$, 100%).

Example 7

2-(2,6-Dibutyl-benzyl)-4,5-dihydro-1H-imidazole a) 1,3-Dibutyl-2-(2,2-dibromo-vinyl)-benzene

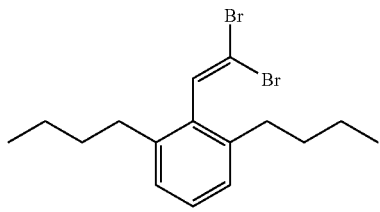

1,3-Dibutyl-2-(2,2-dibromo-vinyl)-benzene was prepared from 2,6-dibutyl-benzaldehyde in analogy to Example 1d): colourless liquid; MS (EI): 376.0 and 374.0 and 372.0 (M$^{\cdot+}$), 295.2 and 293.2 ((M-Br)$^{+\cdot}$), 214.3 ((M-2Br)$^{+\cdot}$), 171.1 ((M-(2Br+C$_3$H$_7$))$^{+\cdot}$, 129.1 (((M-(2Br+C$_3$H$_7$+C$_3$H$_6$))$^{+\cdot}$), 100%).

b) 2-(2,6-Dibutyl-benzyl)-4,5-dihydro-1H-imidazole

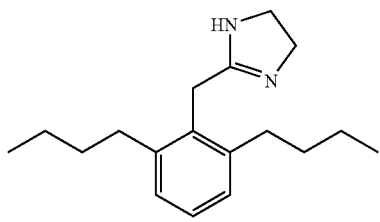

2-(2,6-Dibutyl-benzyl)-4,5-dihydro-1H-imidazole was prepared from 1,3-dibutyl-2-(2,2-dibromo-vinyl)-benzene in analogy to Example 1e): colourless crystals; MS (ISP): 273.1 ((M+H)$^{+\cdot}$).

Example 8

2-[1,1';3',1'']Terphenyl-2'-ylmethyl-4,5-dihydro-1H-imidazole a) 2'-(2,2-Dibromo-vinyl)-[1,1';3',1'']terphenyl

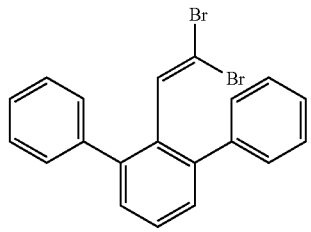

2'-(2,2-Dibromo-vinyl)-[1,1';3',1''] terphenyl was prepared from 2,6-diphenylbenzaldehyde in anology to Example 1d): light yellow crystals; MS (EI): 416.2 and 414.5 and 412.2 (M$^{+\cdot}$), 335.0 and 333.0 ((M-Br)$^{+\cdot}$), 254.2 (((M-2Br)$^{+\cdot}$), 100%).

b) 2-[1,1';3',1'']Terphenyl-2'-ylmethyl-4,5-dihydro-1H-imidazole

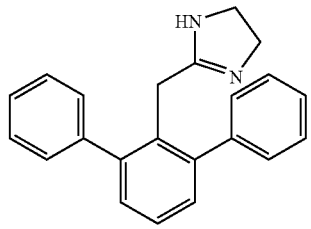

2-[1,1';3',1'']Terphenyl-2'-ylmethyl-4,5-dihydro-1H-imidazole was prepared from 2'-(2,2-Dibromo-vinyl)-[1,1';3',1''] terphenyl in analogy to Example 1e): light yellow crystals; MS (ISP): 312.9 ((M+H)$^{+\cdot}$).

Example 9

2-(2-Ethyl-6-methoxy-benzyl)-4,5-dihydro-1H-imidazole a) (E)-[1-(2-Ethyl-6-methoxy-phenyl)-methylidene]-(1-isopropyl-2-methyl-propyl)-amine

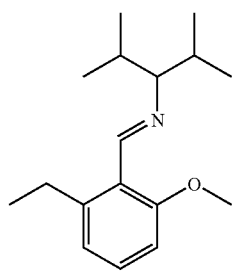

To a solution of 10.0 g (38 mmol) [1-(2,6-dimethoxyphenyl)-meth-(E)-ylidene]-(1-isopropyl-2-methyl-propyl)-amine in 30 ml dry THF cooled to −20° C. were added 91.2 ml of a 0.5M solution of ethyl lithium in cyclohexane/benzene drop-wise to keep temperature below 0° C. Then the mixture was stirred at −20° C. for further 30 min and the reaction quenched by addition of water. The aqueous phase was extracted with ethyl acetate, the combined extracts washed with brine, dried over Na$_2$SO$_4$, filtered and evaporated. Purification of the crude product by flash chromatography on silica gel with a heptane/ethyl acetate gradient provided 4.30 g (E)-[1-(2-ethyl-6-methoxy-phenyl)-methylidene]-(1-isopropyl-2-methyl-propyl)-amine as colourless liquid: MS (EI): 261.4 (M$^+$·), 218.3 ((M-((CH$_3$)$_2$CH)$^+$·), 100%).

b) 2-Ethyl-6-methoxy-benzaldehyde

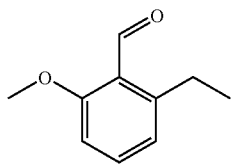

A solution of 1.0 g (E)-[1-(2-ethyl-6-methoxy-phenyl)-methylidene]-(1-isopropyl-2-methyl-propyl)-amine in 1 ml THF and 0.19 ml 4N HCl was heated to reflux for 1 hour then cooled to ambient temperature and poured onto a 1N aqueous NaOH solution. The aqueous phase was extracted with ethyl acetate, the combined extracts washed with brine, dried over Na$_2$SO$_4$, filtered and evaporated. The residue was purified by flash-chromatography on silica gel with a heptane/ethyl acetate gradient as eluent: 0.50 g 2-ethyl-6-methoxy-benzaldehyde as colourless oil: MS (EI): 261.2 (M$^+$·), 218.2 ((M-((CH$_3$)$_2$CH))$^+$·, 100%).

c) 2-(2,2-Dibromo-vinyl)-1-ethyl-3-methoxy-benzene

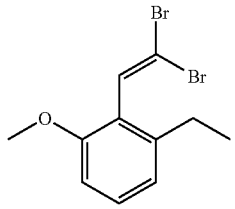

2-(2,2-Dibromo-vinyl)-1-ethyl-3-methoxy-benzene was prepared from 2-ethyl-6-methoxy-benzaldehyde in analogy to Example 1d): colourless liquid; MS (EI): 321.9 and 319.9 and 318.0 (M$^+$·), 241.1 and 239.1 ((M-Br)$^+$·), 160.1 (((M-2Br)$^+$·), 100%).

d) 2-(2-Ethyl-6-methoxy-benzyl)-4,5-dihydro-1H-imidazole

2-(2-Ethyl-6-methoxy-benzyl)-4,5-dihydro-1H-imidazole was prepared from 2-(2,2-dibromo-vinyl)-1-ethyl-3-methoxy-benzene in analogy to Example 1e): light yellow solid: MS (EI): 218.2 (M$^+$·), 187.2 ((M-(CH$_3$NH$_2$))$^+$·, 100%).

Example 10

2-(2-Methoxy-6-methyl-benzyl)-4,5-dihydro-1H-imidazole a) 2-(2,2-Dibromo-vinyl)-1-methoxy-3-methyl-benzene

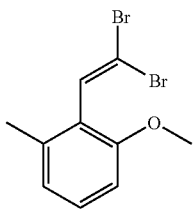

2-(2,2-Dibromo-vinyl)-1-methoxy-3-methyl-benzene was prepared from 2-methoxy-6-methyl-benzaldehyde in analogy to Example 1d): $^1$H-NMR (CDCl$_3$): 2.26 s, 3H(CH$_3$-aryl), 3.81 s, 3H(CH$_3$—O), 6.73 d, 1H and 6.82 d, 1H and 7.22 t, 1H (aryl-H), 7.32 s, 1H(HC=).

b) 2-(2-Methoxy-6-methyl-benzyl)-4,5-dihydro-1H-imidazole

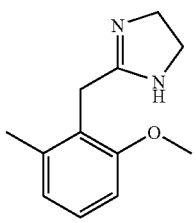

2-(2-Methoxy-6-methyl-benzyl)-4,5-dihydro-1H-imidazole was prepared from 2-(2,2-dibromo-vinyl)-1-methoxy-3-methyl-benzene in analogy to Example 1e): light yellow solid: MS (ISP): 205.0 ((M+H)$^+$·).

Example 11

2-(2-Ethyl-6-methyl-benzyl)-4,5-dihydro-1H-imidazole a) 2-(2,2-Dibromo-vinyl)-1-ethyl-3-methyl-benzene

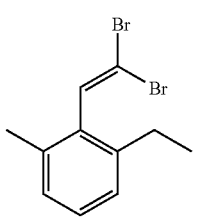

2-(2,2-Dibromo-vinyl)-1-ethyl-3-methyl-benzene was prepared from 2-ethyl-6-methyl-benzaldehyde in analogy to Example 1d): $^1$H-NMR (CDCl$_3$): 1.19 t, 3H(CH$_3$—CH$_2$), 2,26 s, 3H (CH$_7$-aryl), 2.56 q, 3H(CH$_3$—CH$_2$), 7.07 m, 2H and 7.22 t, 1H (aryl-H), 7.44 s, 1H(HC=).

b) 2-(2-Ethyl-6-methyl-benzyl)-4,5-dihydro-1H-imidazole

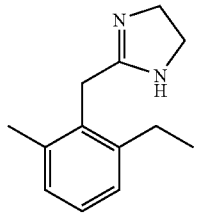

2-(2-Ethyl-6-methyl-benzyl)-4,5-dihydro-1H-imidazole was prepared from) 2-(2,2-dibromo-vinyl)-1-ethyl-3-methyl-benzene in analogy to Example 1e): light yellow solid: MS (ISP): 202.9 ((M+H)$^{+\cdot}$).

Example 12

2-(2-Ethyl-6-isopropyl-benzyl)-4,5-dihydro-1H-imidazole a) (E)-[1-(2-Ethyl-6-isopropyl-phenyl)-methylidene]-(1-isopropyl-2-methyl-propyl)-amine

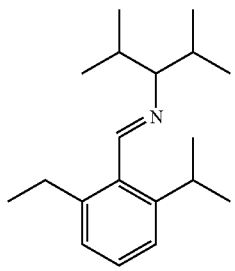

To a solution of 0.8 g (3.1 mmol) (E)-[1-(2-ethyl-6-methoxy-phenyl)-methylidene]-(1-isopropyl-2-methyl-propyl)-amine (Example 3 a)) in 3 ml dry THF cooled to −20° C. were added 9.62 ml of a 0.7M solution of isopropyl lithium in pentane drop-wise to keep temperature below 0° C. Then the mixture was stirred at −20° C. for further 30 min and the reaction quenched by addition of water. The aqueous phase was extracted with ethyl acetate, the combined extracts washed with brine, dried over Na$_2$SO$_4$, filtered and evaporated. Purification of the crude product by flash chromatography on silica gel with heptane as eluent provided 0.220 g (E)-[1-(2-ethyl-6-isopropyl-phenyl)-methylidene]-(1-isopropyl-2-methyl-propyl)-amine as colourless liquid: MS (ISP): 274.1 (M+H$^{+\cdot}$).

b) 2-(2-Ethyl-6-isopropyl-benzyl)-4,5-dihydro-1H-imidazole

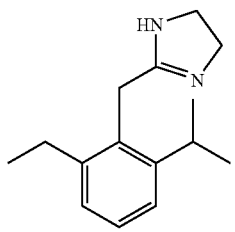

2-(2-Ethyl-6-isopropyl-benzyl)-4,5-dihydro-1H-imidazole imidazole was prepared from (E)-[1-(2-ethyl-6-isopropyl-phenyl)-methylidene]-(1-isopropyl-2-methyl-propyl)-amine following reaction sequence Example 1 c) to e): yellow solid: MS (EI): 230.3 (M$^{+\cdot}$), 215.2 ((M-(CH$_3$)$^{+\cdot}$), 100%).

Example 13

2-(3-Ethyl-biphenyl-2-ylmethyl)-4,5-dihydro-1H-imidazole a) (E)-[1-(3-Ethyl-biphenyl-2-yl)-methylidene]-(1-isopropyl-2-methyl-propyl)-amine

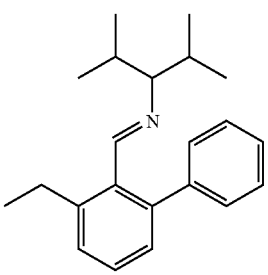

(E)-[1-(3-Ethyl-biphenyl-2-yl)-methylidene]-(1-isopropyl-2-methyl-propyl)-amine was prepared from (E)-[1-(2-ethyl-6-methoxy-phenyl)-methylidene]-(1-isopropyl-2-methyl-propyl)-amine (Example 3 a) and phenyl lithium in analogy to procedure Example 5 a): colourless liquid: MS (ISP): 308.1 ((M+H)$^{+\cdot}$), 192.9 (((M-((iPr$_2$)$_2$CHNH$_2$))$^{+\cdot}$), 100%).

b) 2-(3-Ethyl-biphenyl-2-ylmethyl)-4,5-dihydro-1H-imidazole

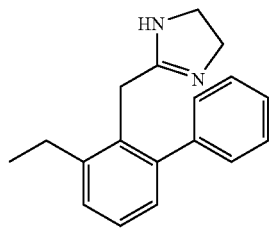

2-(3-Ethyl-biphenyl-2-ylmethyl)-4,5-dihydro-1H-imidazole was prepared from (E)-[1-(3-Ethyl-biphenyl-2-yl)-methylidene]-(1-isopropyl-2-methyl-propyl)-amine following reaction sequence Example 1 c) to e): light yellow solid: MS (EI): 264.2 (M$^{+\cdot}$), 263.3 (((M-H)$^{+\cdot}$), 100%).

Example 14 rac-2-(2-sec-Butyl-6-ethyl-benzyl)-4,5-dihydro-1H-imidazole a) rac-(E)-[1-(2-sec-Butyl-6-ethyl-phenyl)-methylidene]-(1-isopropyl-2-methyl-propyl)-amine

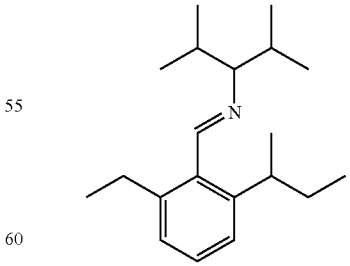

rac-(E)-[1-(2-sec-Butyl-6-ethyl-phenyl)-methylidene]-(1-isopropyl-2-methyl-propyl)-amine was prepared from (E)-[1-(2-ethyl-6-methoxy-phenyl)-methylidene]-(1-isopropyl-2-methyl-propyl)-amine (Example 3 a) and sec.-butyl lithium in analogy to procedure Example 5 a): colourless liquid: MS (ISP): 288.1 ((M+H)$^{+\cdot}$).

b) rac-2-sec-Butyl-6-ethyl-benzaldehyde

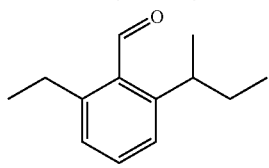

rac-2-sec-Butyl-6-ethyl-benzaldehyde was prepared from rac-(E)-[1-(2-sec-butyl-6-ethyl-phenyl)-methylidene]-(1-isopropyl-2-methyl-propyl)-amine in analogy to Example 1 c): colourless liquid.

c) rac-1-sec-Butyl-2-(2,2-dibromo-vinyl)-3-ethyl-benzene

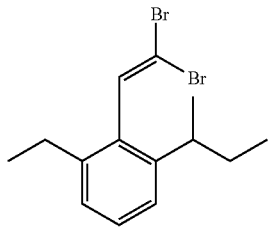

rac-1-sec-Butyl-2-(2,2-dibromo-vinyl)-3-ethyl-benzene was prepared from rac-2-sec-butyl-6-ethyl-benzaldehyde in anology to Example 1 d): colourless liquid; MS (EI): 348.0 and 346.0 and 343.9 ($M^{+\cdot}$), 186.1 (($M-2Br)^{+\cdot}$), 157.0 (($M-(2Br+CH_3CH_2))^{+\cdot}$, 100%).

d) rac-2-(2-sec-Butyl-6-ethyl-benzyl)-4,5-dihydro-1H-imidazole

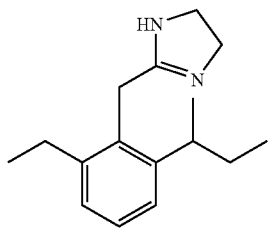

rac-2-(2-sec-Butyl-6-ethyl-benzyl)-4,5-dihydro-1H-imidazole was prepared from rac-1-sec-butyl-2-(2,2-dibromo-vinyl)-3-ethyl-benzene in analogy to Example 1 e): light yellow crystals; MS (EI): 244.3 ($M^{+}$ ), 229.3 ((($M-CH_3)^{+\cdot}$), 100%).

Example 15

2-(2-Ethyl-6-isobutyl-benzyl)-4,5-dihydro-1H-imidazole a) (E)-[1-(2-Ethyl-6-isobutyl-phenyl)-methylidene]-(1-isopropyl-2-methyl-propyl)-amine

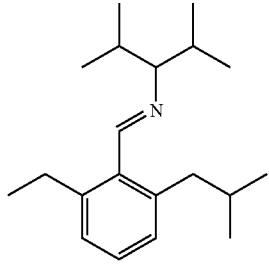

(E)-[1-(2-Ethyl-6-isobutyl-phenyl)-methylidene]-(1-isopropyl-2-methyl-propyl)-amine was prepared from (E)-[1-(2-ethyl-6-methoxy-phenyl)-methylidene]-(1-isopropyl-2-methyl-propyl)-amine (Example 3 a) and isobutyl lithium in analogy to procedure Example 5 a): colourless liquid; NMR (CDCl$_3$, ppm): 0.88 t, 18H (2×(CH$_3$)$_2$C), 1.20 t, 3H(CH$_3$—CH$_2$), 1.88 septett, 1H(CH(CH$_3$)$_2$), 2.08 m, 2H(NCH(CH(CH$_3$)$_2$)$_2$), 2.48 t, 1H(NCH), 2.68 d, 2H (aryl -CH$_2$CH), 2.88 q, 2H(CH$_3$-CH$_2$), 7.00 d, 1H and 7.08 d, 1H and 7.19 t, 1H (aryl-H), 8.49 1H (=CHN).

b) 2-Ethyl-6-isobutyl-benzaldehyde

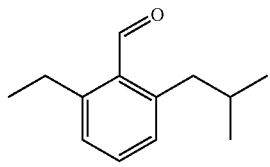

2-Ethyl-6-isobutyl-benzaldehyde was prepared from (E)-[1-(2-Ethyl-6-isobutyl-phenyl)-methylidene]-(1-isopropyl-2-methyl-propyl)-amine in analogy to Example 1 c): colourless liquid.

c) 2-(2,2-Dibromo-vinyl)-1-ethyl-3-isobutyl-benzene

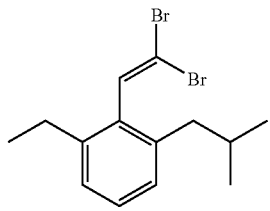

2-(2,2-Dibromo-vinyl)-1-ethyl-3-isobutyl-benzene was prepared from 2-ethyl-6-isobutyl-benzaldehyde in anology to Example 1 d): colourless liquid; MS (EI): 347.9 and 346.0 and 344.0 ($M^{+\cdot}$), 267.1 and 265.1 (($M-Br)^{+\cdot}$), 186.2 (($M-2Br)^{+\cdot}$), 143.1 (($M-(2Br+(CH_3)_2CH_2))^{+\cdot}$, 100%).

d) 2-(2-Ethyl-6-isobutyl-benzyl)-4,5-dihydro-1H-imidazole

2-(2-Ethyl-6-isobutyl-benzyl)-4,5-dihydro-1H-imidazole was prepared from 2-(2,2-Dibromo-vinyl)-1-ethyl-3-isobutyl-benzene in analogy to Example 1 e): colourless crystals; MS (EI): 244.3 ($M^{+\cdot}$), 229.2 (($M-CH_3)^{+\cdot}$, 100%).

Example 16

2-(2-Butyl-6-ethyl-benzyl)-4,5-dihydro-1H-imidazole a) (E)-[1-(2-Butyl-6-ethyl-phenyl)-methylidene]-(1-isopropyl-2-methyl-propyl)-amine

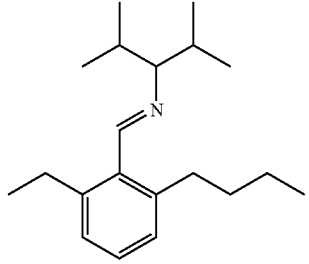

(E)-[1-(2-Butyl-6-ethyl-phenyl)-methylidene]-(1-isopropyl-2-methyl-propyl)-amine was prepared from (E)-[1-(2-ethyl-6-methoxy-phenyl)-methylidene]-(1-isopropyl-2-methyl-propyl)-amine (Example 3a) and butyl lithium in analogy to procedure Example 5 a): colourless liquid; NMR (CDCl$_3$, ppm): 0.90 m, 15H (2×(CH$_3$)$_2$C, CH$_3$(CH$_2$)$_3$), 1.20 t, 3H(CH$_3$-CH$_2$), 1.35 m, 2H(CH$_3$CH$_2$(CH$_2$)$_2$), 1.60 m, 2H(CH$_2$CH$_2$CH$_2$), 2.08 m, 2H(NCH(CH(CH$_3$)$_2$)$_2$), 2.48 t, 1H (NCH), 2.84 m, 2H (aryl-CH$_2$CH$_2$), 2.88 q, 2H(CH$_3$-CH$_2$), 7.04-7.08 m, 2H, and 7.20 t, 1H (aryl-H), 8.49 1H (=CHN).

b) 2-Butyl-6-ethyl-benzaldehyde

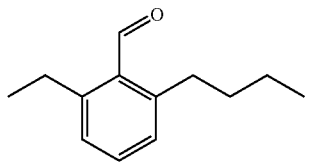

2-Butyl-6-ethyl-benzaldehyde was prepared from (E)-[1-(2-butyl-6-ethyl-phenyl)-methylidene]-(1-isopropyl-2-methyl-propyl)-amine in analogy to Example 1c): colourless liquid.

c) 1-Butyl-2-(2,2-dibromo-vinyl)-3-ethyl-benzene

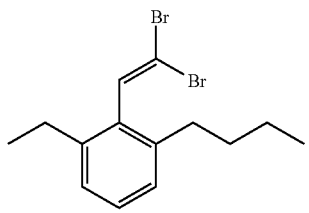

Butyl-2-(2,2-dibromo-vinyl)-3-ethyl-benzene was prepared from 2-butyl-6-ethyl-benzaldehyde in analogy to Example 1d): colourless liquid; MS (EI): 347.9 and 346.0 and 344.0 (M$^{+\cdot}$), 267.1 and 265.1 ((M-Br)$^{+\cdot}$), 186.2 ((M-2Br)$^{+\cdot}$), 143.1 ((M-(2Br+(CH$_3$(CH$_2$)$_2$)))$^{+\cdot}$, 100%).

d) 2-(2-Butyl-6-ethyl-benzyl)-4,5-dihydro-1H-imidazole

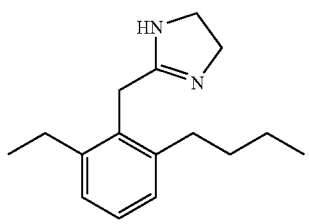

2-(2-Butyl-6-ethyl-benzyl)-4,5-dihydro-1H-imidazole was prepared from 1-butyl-2-(2,2-dibromo-vinyl)-3-ethyl-benzene in analogy to Example 1e): light yellow crystals; MS (EI): 244.3 (M$^{+\cdot}$), 215.2 (((M-CH$_3$CH$_2$)$^{+\cdot}$), 100%).

Procedure B

Example 17

2-(2,3-Dichloro-benzyl)-4,5-dihydro-1H-imidazole

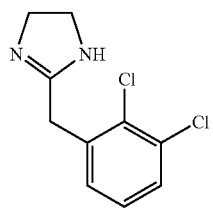

A mixture of 500 mg (2.7 mmol) 2,3-dichlorophenylacetonitrile and 624 mg (2.7 mmol) ethylene diamine p-toluenesulfonic acid mono salt was heated neat to 140° C. and the liquid stirred for 5h at this temperature. Then the cooled reaction mixture was diluted with water and extracted with ethyl acetate, the combined extracts washed with brine, dried over Na$_2$SO$_4$, filtered and evaporated. Trituration of the crude product in tert-butyl methyl ether provided pure 2-(2,3-dichloro-benzyl)-4,5-dihydro-1H-imidazole as colourless crystals: MS (ISP): 231.1 and 229.1 ((M+H)$^{+\cdot}$).

In analogy to Example 17 were prepared Examples 18, 104 to 108, 175.

Example 18 rac-2-[1-(2,3-Dimethyl-phenyl)-ethyl]-4,5-dihydro-1H-imidazole hydrochloride

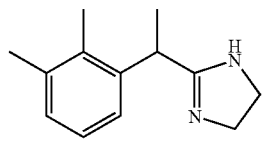

rac-2-[1-(2,3-Dimethyl-phenyl)-ethyl]-4,5-dihydro-1H-imidazole hydrochloride was prepared from rac-2-(2,3-dimethyl-phenyl)-propionitrile in analogy to Example 17: colourless crystals; MS (EI): 202.2 (M$^{+\cdot}$).

Example 19

2-(4-Fluoro-2,6-dimethyl-benzyl)-4,5-dihydro-1H-imidazole a) (4-Fluoro-2,6-dimethyl-phenyl)-acetonitrile

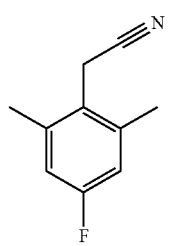

A solution of 1.86 g (9 mmol) 2,6-dimethyl-4-fluoro-benzyl bromide and 0.420 g (9 mmol) sodium cyanide in 21 ml ethanol/water 6:1 was heated to reflux for 4h. The cooled reaction mixture was concentrated and extracted with ethyl acetate. The combined extracts were washed with brine, dried over Na$_2$SO$_4$, filtered and evaporated. Filtration of the residue through a silica gel pad with heptane/ethyl acetate 1:1 provided (4-fluoro-2,6-dimethyl-phenyl)-acetonitrile as colourless solid: MS (EI): 163.1 (M$^+$·), 148.1 ((M-CH$_3$)$^+$·), 136.1 ((M-HCN)$^+$·, 100%).

b) 2-(4-Fluoro-2,6-dimethyl-benzyl)-4,5-dihydro-1H-imidazole

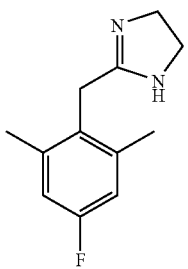

A mixture of 1.30 g (8 mmol) (4-fluoro-2,6-dimethyl-phenyl)-acetonitrile, 3.83 g (4.27 ml, 64 mmol) ethylene diamine and 0.128 g (4 mmol) sulfur in a pressurized glass tube was heated under microwave irradiation to 200° C. for 20 min. The cooled reaction mixture was poured onto water, extracted with methylene chloride, the combined extracts washed with brine, dried over Na$_2$SO$_4$, filtered and evaporated. Purification of the residue by flash-chromatography over silica gel with a ethyl acetate/methanol gradient containing 1% conc. ammonia provided 2-(4-fluoro-2,6-dimethyl-benzyl)-4,5-dihydro-1H-imidazole as light yellow solid: MS (EI): 206.1 ((M$^+$·), 100%).

In analogy to Example 19 b) were prepared Examples 20, 21, 44 to 49 and 51 to 69, 109, 154, 179, 180, and 182.

Example 20

2-(2,6-Bis-trifluoromethyl-benzyl)-4,5-dihydro-1H-imidazole a) 2-Bromomethyl-1,3-bis-trifluoromethyl-benzene

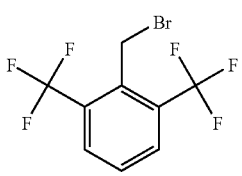

To 1 ml of a mixture of 48% aqueous HBr solution and conc. sulfuric acid (2:1 v/v) were added 0.81 g (3.3 mmol) (2,6-bis-trifluoromethyl-phenyl)-methanol and the solution heated to reflux for 6 h. Then the reaction mixture was cooled to rt, diluted with water and extracted with tert-butyl methyl ether. The combined extracts were washed with brine, dried over Na$_2$SO$_4$, filtered and evaporated. Kugelrohr distillation provided 2-bromomethyl-1,3-bis-trifluoromethyl-benzene as colourless oil of b.p. 135-140° C./22 mbar: MS (EI): 307.9 and 305.9 (M$^+$·), 227.1 (((M-Br)$^+$·), 100%).

b) (2,6-Bis-trifluoromethyl-phenyl)-acetonitrile

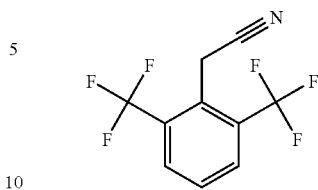

A solution of 0.73 g (2.4 mmol) 2-bromomethyl-1,3-bistrifluoromethyl-benzene and 0.183 g (3.7 mmol) sodium cyanide in 10 ml EtOH/H$_2$O 6:1 (v/v) was hated to reflux for 3h. Then the reaction mixture was evaporated, the residue taken up in water and extracted with tert-butyl methyl ether. The combined extracts were washed with saturated aqueous NaHCO$_3$ solution and brine, dried over Na$_2$SO$_4$ and evaporated. Purification by flash chromatography on silica gel with a gradient of 95:5 to 70:30% heptane/ethyl acetate provided (2,6-bis-trifluoromethyl-phenyl)-acetonitrile as colourless crystalline product of m.p. 84.5-86° C.: MS (EI): 253.0 (M$^+$·), 234.1 ((M-F) ·$^+$), 233.1 ((M-HF)$^+$·), 184.0 (((M-CF$_3$)$^+$·), 100%).

c) 2-(2,6-Bis-trifluoromethyl-benzyl)-4,5-dihydro-1H-imidazole

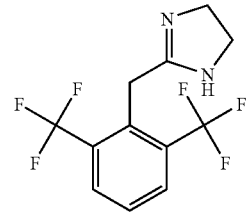

2-(2,6-Bis-trifluoromethyl-benzyl)-4,5-dihydro-1H-imidazole was prepared from (2,6-bis-trifluoromethyl-phenyl)-acetonitrile and ethylene diamine in analogy to Example 19 b): colourless crystals; MS (EI): 296.2 (M$^+$·), 275.1 ((M-F)$^+$·), 267.1 ((M-C$_2$H$_5$)$^+$·), 227.1 (((M-imidazoline)$^+$·), 100%).

Example 21 rac-2-(2,6-Dimethyl-benzyl)-5-methyl-4,5-dihydro-1H-imidazole or tautomer

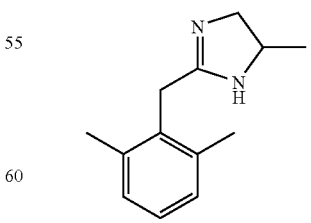

rac-2-(2,6-Dimethyl-benzyl)-5-methyl-4,5-dihydro-1H-imidazole was prepared from 2,6-dimethyl-phenyl-acetonitrile and 1,2-diaminopropane in analogy to Example 19 b): orange powder; MS (EI): 202.3 (M$^+$·).

Example 22 rac-2-[1-(3-Bromo-phenyl)-propyl]-4,5-dihydro-1H-imidazole

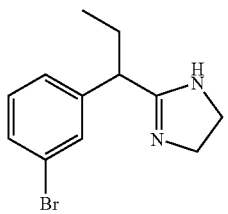

rac-2-[1-(3-Bromo-phenyl)-propyl]-4,5-dihydro-1H-imidazole was prepared from 2-(3-bromo-phenyl)-butyronitrile and ethylene diamine in analogy to Example 19 b) but the reaction mixture was heated under microwave irradiation to 130° C. for 1 hour: colourless powder; MS (ISP): 269.0 and 267.0 ((M+H)$^{+ \cdot}$).

In analogy to Example 22 were prepared Examples 23 to 31 and 33 to 43.

Example 23 rac-2-(1-p-Tolyl-propyl)-4,5-dihydro-1H-imidazole a) rac-1-p-Tolyl-propan-1-ol

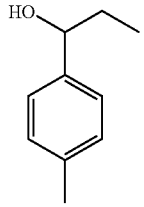

1.60 g (42.2 mmol) Sodium borohydride were added portion-wise, with stirring to a solution of 5.0 g (33.7 mmol) 4-methyl-propiophenone in 50 ml methanol at 0° C., over a three hour period. The reaction mixture was allowed to warm to ambient temperature over 2 hours and the solvent was then removed in vacuo. The residue obtained was partitioned between dichloromethane and water. The organic phase was separated and the aqueous phase extracted with dicholoromethane. The combined organic phase was washed with water then brine, dried over MgSO$_4$ and concentrated to give rac-1-p-tolyl-propan-1-ol as a colourless oil. NMR (CDCl$_3$, ppm): 0.81 (3H, t), 1.72 (2H, m), 2.26 (3H, s), 4.56 (1H, t), 7.05 (4H, m).

b) rac-1-(1-Bromo-propyl)-4-methyl-benzene

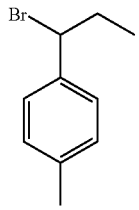

4.5 g (1.6 ml, 16.7 mmol) Phosphorus tribromide were added portion-wise, with stirring to a solution of 4.98 g (33.0 mmol) rac-1-p-tolyl-propan-1-ol and 0.37 ml pyridine in 17 ml anhydrous diethyl ether at 0° C. The reaction mixture was warmed to ambient temperature and the reaction monitored by HPLC to completion. The reaction mixture was poured onto ice-water and the whole was extracted with dichloromethane. The organic phase was washed with brine, dried over MgSO$_4$ and evaporated to give rac-1-(1-bromo-propyl)-4-methyl-benzene as a colourless oil that did not require further purification: NMR (CDCl$_3$, ppm): 1.01 (3H, t), 2.28 (2H, m), 2.40 (3H, s), 4.92 (1H, t), 7.20 (4H, m).

c) rac-2-p-tolyl-butyronitrile

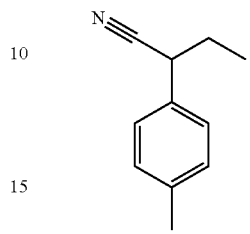

7.36 g (74.4 mmol) Trimethylsilyl cyanide was added to a solution of 74.4 ml (1.0 M in THF, 74.4 mmol) tetrabutylammonium flouride in 300 ml acetonitrile and the mixture was stirred for 5 minutes. 5.28 g (24.8 mmol) rac-1-(1-Bromo-propyl)-4-methylbenzene were added and the reaction mixture was stirred at ambient temperature for 16 hours. The solvent was removed in vacuo and the viscous residue obtained was partitioned between water and dichloromethane. The dichloromethane was separated, then washed with water, dried over MgSO$_4$ and evaporated to dryness. Purification of the residue by column chromatography on silica gel with a gradient of heptane to 9:1 heptane/ethyl acetate afforded rac-2-p-tolyl-butyronitrile as a colourless oil. NMR (CDCl$_3$, ppm): 0.95 (3H, t), 1.77 (2H, m), 2.21 (3H, s), 3.58 (1H, t), 7.07 (4H, m).

d) rac-2-(1-p-Tolyl-propyl)-4,5-dihydro-1H-imidazole

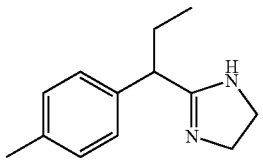

rac-2-(1-p-Tolyl-propyl)-4,5-dihydro-1H-imidazole was prepared from rac-2-p-tolyl-butyronitrile and ethylene diamine in analogy to Example 22: colourless powder; MS (ISP): 203.0 ((M+H)$^{+ \cdot}$).

Example 24 rac-2-[1-(3-Chloro-phenyl)-propyl]-4,5-dihydro-1H-imidazole a) rac-2-(3-chloro-phenyl)-butyronitrile

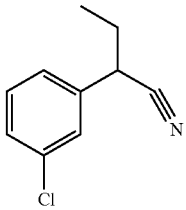

rac-2-(3-chloro-phenyl)-butyronitrile was prepared from rac-1-(1-bromo-propyl)-3-chloro-benzene and trimethylsilyl cyanide in analogy to Example 23 c): colourless oil.

b) rac-2-[1-(3-Chloro-phenyl)-propyl]-4,5-dihydro-1H-imidazole

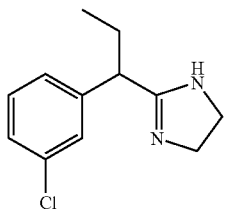

rac-2-[1-(3-Chloro-phenyl)-propyl]-4,5-dihydro-1H-imidazole was prepared from 2-(3-chloro-phenyl)-butyronitrile and ethylene diamine in analogy to Example 22: colourless powder;MS (ISP): 223.0 ((M+H)$^{+\cdot}$).

Example 25 rac-2-[1-(4-Chloro-phenyl)-propyl]-4,5-dihydro-1H-imidazole a) rac-2-(4-Chloro-phenyl)-butyronitrile

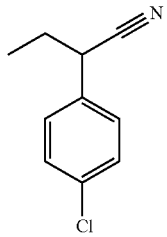

To a suspension of 0.42 g (10.5 mmol) NaH (60% dispersion in mineral oil) were added at ambient temperature 1.67 g (11 mmol) 4-chlorophenyl-acetonitrile in 10 ml anhydrous tetrahydrofuran. The reaction mixture was stirred at ambient temperature for 2 hours and then cooled to −20° C. 0.78 ml (10.5 mmol) Bromoethane was added drop-wise to the reaction mixture over 30 minutes. The reaction was warmed to ambient temperature while stirring over 2 hours. The reaction mixture was quenched by addition of 20 ml of saturated ammonium chloride solution. Dichloromethane was added, the organic phase was separated and the aqueous phase washed with dichloromethane. The combined organic phase was dried over MgSO$_4$ and evaporated to afford rac-2-(4-chloro-phenyl)butyronitrile as a brown oil that did not require further purification. NMR (CDCl$_3$, ppm): 0.80 (3H, t), 1.82 (2H, dq), 3.64 (1H, t), 7.30-7.15 (4H, m).

b) rac-2-[1-(4-Chloro-phenyl)-propyl]-4,5-dihydro-1H-imidazole

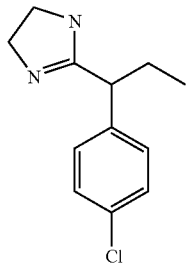

rac-2-[1-(4-Chloro-phenyl)-propyl]-4,5-dihydro-1H-imidazole was prepared from rac-2-(4-chloro-phenyl)butyronitrile and ethylene diamine in analogy to Example 22: colourless powder; MS (ISP): 223.0 ((M+H)$^{+\cdot}$).

Example 26 rac-2-[1-(3-Trifluoromethyl-phenyl)-propyl]-4,5-dihydro-1H-imidazole

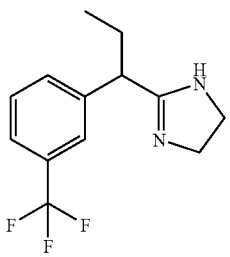

rac-2-[1-(3-Trifluoromethyl-phenyl)-propyl]-4,5-dihydro-1H-imidazole was prepared from rac-2-(3-trifluoromethyl-phenyl)-butyronitrile and ethylene diamine in analogy to Example 22: colourless powder; MS (ISP): 257.0 ((M+H)$^{+\cdot}$).

Example 27 rac-2-[1-(4-Fluoro-phenyl)-propyl]-4,5-dihydro-1H-imidazole

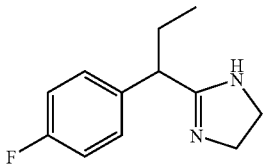

rac-2-[1-(4-Fluoro-phenyl)-propyl]-4,5-dihydro-1H-imidazole was prepared from rac-2-(4-fluoro-phenyl)-butyronitrile and ethylene diamine in analogy to Example 22: colourless powder; MS (ISP): 207.0 ((M+H)$^{+\cdot}$).

Example 28 rac-2-[1-(2,3-Difluoro-phenyl)-propyl]-4,5-dihydro-1H-imidazole a) rac-1-(1-Bromo-propyl)-2,3-difluoro-benzene

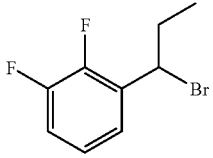

rac-1-(1-Bromo-propyl)-2,3-difluoro-benzene was prepared from rac-1-(2,3-Difluoro-phenyl)-propan-1-ol and phosphorus tribromide in analogy to Example 23 b): colourless oil.

b) rac-2-(2,3-Difluoro-phenyl)-butyronitrile

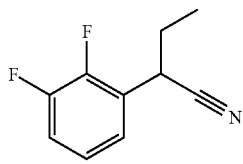

rac-2-(2,3-Difluoro-phenyl)-butyronitrile was prepared from rac-1-(1-bromo-propyl)-2,3-difluoro-benzene and trimethylsilyl cyanide in analogy to Example 23 c): colourless oil.

c) rac-2-[1-(2,3-Difluoro-phenyl)-propyl]-4,5-dihydro-1H-imidazole

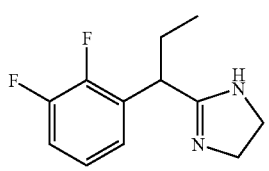

rac-2-[1-(2,3-Difluoro-phenyl)-propyl]-4,5-dihydro-1H-imidazole was prepared from rac-2-(2,3-difluoro-phenyl)-butyronitrile and ethylene diamine in analogy to Example 22: colourless powder; MS (ISP): 225.0 ((M+H)$^{+\cdot}$).

Example 29 rac-2-(2-Methyl-1-phenyl-propyl)-4,5-dihydro-1H-imidazole

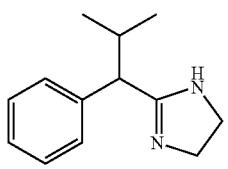

rac-2-(2-Methyl-1-phenyl-propyl)-4,5-dihydro-1H-imidazole was prepared from rac-3-methyl-2-phenyl-butyronitrile and ethylene diamine in analogy to Example 22: colourless powder; MS (ISP): 203.0 ((M+H)$^{+\cdot}$).

Example 30 rac-2-[1-(2,5-Difluoro-phenyl)-propyl]-4,5-dihydro-1H-imidazole a) rac-1-(2,5-Difluoro-phenyl)-propan-1-ol

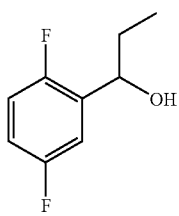

rac-1-(2,5-Difluoro-phenyl)-propan-1-ol was prepared from 1-(2,5-difluoro-phenyl)-propan-1-one in analogy to Example 23 a): colourless oil.

b) rac-2-(1-Bromo-propyl)-1,4-difluoro-benzene

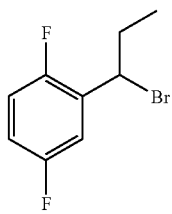

rac-2-(1-Bromo-propyl)-1,4-difluoro-benzene was prepared from rac-1-(2,5-difluoro-phenyl)-propan-1-ol and phosphorus tribromide in analogy to Example 23 b): colourless oil.

c) rac-2-(2,5-Difluoro-phenyl)-butyronitrile

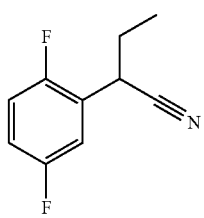

rac-2-(2,5-Difluoro-phenyl)-butyronitrile was prepared from rac-2-(1-bromo-propyl)-1,4-difluoro-benzene and trimethylsilyl cyanide in analogy to Example 23 c): colourless oil.

d) rac-2-[1-(2,5-Difluoro-phenyl)-propyl]-4,5-dihydro-1H-imidazole

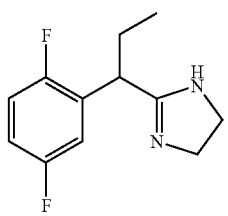

rac-2-[1-(2,5-Difluoro-phenyl)-propyl]-4,5-dihydro-1H-imidazole was prepared from rac-2-(2,5-difluoro-phenyl)-butyronitrile and ethylene diamine in analogy to Example 22: colourless powder; MS (ISP): 225.0 ((M+H)$^{+\cdot}$).

Example 31 rac-2-[1-(4-Trifluoromethyl-phenyl)-propyl]-4,5-dihydro-1H-imidazole

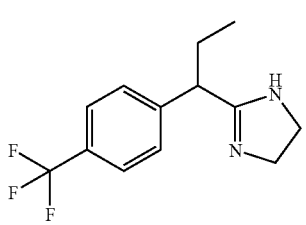

rac-2-[1-(4-Trifluoromethyl-phenyl)-propyl]-4,5-dihydro-1H-imidazole was prepared from rac-2-(4-trifluoromethyl-phenyl)-butyronitrile and ethylene diamine in analogy to Example 22: colourless powder; MS (ISP): 257.0 ((M+H)+·).

Example 32

2-(3-Bromo-2,6-diethyl-benzyl)-4,5-dihydro-1H-imidazole a) 3-Bromo-2,6-diethyl-benzaldehyde

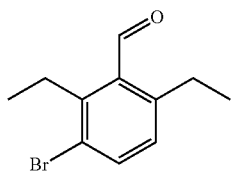

To a solution of 8.01 g (60 mmol) aluminum trichloride in 10 ml dichloromethane were added at ambient temperature drop-wise 5.52 g (34 mmol) 2,6-diethyl-benzaldehyde (Example 1 c)); exothermic reaction. To the resulting dark red solution was added slowly drop-wise a solution of 5.5 g (34 mmol) bromine in 7 ml dichloromethane; strong exothermic reaction. Then the mixture was heated to 40° C. for 3 hours. The reaction mixture was cooled to ambient temperature and poured onto ice. The organic phase was separated and the aqueous solution extracted with dichloromethane, the combined extracts washed with 2N HCl solution, saturated sodium bicarbonate solution and brine, dried over MgSO$_4$, filtered and evaporated: 7.0 g 3-bromo-2,6-diethyl-benzaldehyde of 90% purity (HPLC) that did not require further purification.

b) (3-Bromo-2,6-diethyl-phenyl)-methanol

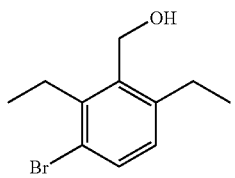

(3-Bromo-2,6-diethyl-phenyl)-methanol was prepared from 3-bromo-2,6-diethyl-benzaldehyde in analogy to Example 23 a): brown oil that did not require further purification.

c) 1-Bromo-3-chloromethyl-2,4-diethyl-benzene

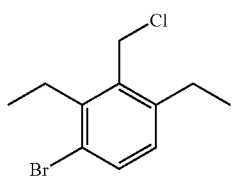

To a solution of 5.84 g (24 mmol) (3-bromo-2,6-diethyl-phenyl)-methanol in 60 ml dichloromethane were added 10 drops N,N-dimethylformamide and drop-wise within 5 minutes 5.71 g (3.5 ml, 5.71 mmol) thionyl chloride. The mixture was stirred at ambient temperature over night, then the volatile parts distilled off under reduced pressure. 1-Bromo-3-chloromethyl-2,4-diethyl-benzene was obtained as an oily residue which was used immediately for the following reaction.

d) (3-Bromo-2,6-diethyl-phenyl)-acetonitrile

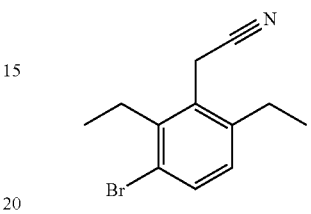

To a solution of 6.28 g (24 mmol) 1-bromo-3-chloromethyl-2,4-diethyl-benzene in 120 ml tetrahydrofurane/N,N-dimethylformamide 1:1 cooled to 0° C. were added 1.76 g (36 mmol) sodium cyanide. The mixture was warmed to 50° C. and stirred at this temperature over night. Then the reaction mixture was diluted with ethyl acetate and extracted several times with water. The organic phase was dried over Na$_2$SO$_4$, filtered and evaporated: 7.2 g (3-bromo-2,6-diethyl-phenyl)-acetonitrile that did not require further purification.

e) 2-(3-Bromo-2,6-diethyl-benzyl)-4,5-dihydro-1H-imidazole

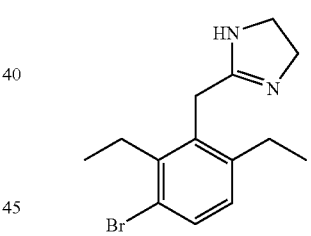

Through a solution of 6.05 g (24 mmol) (3-bromo-2,6-diethyl-phenyl)-acetonitrile in 120 ml dichloromethane and 15 ml methanol was bubbled at 0° C. HCl gas for 30 minutes. Then the mixture was stirred in a closed vessel at ambient temperature over night. The mixture was cooled down to 0° C. again and HCl gas bubbled through the mixture for 60 minutes and stirred at ambient temperature for 6 hours; no more starting material detectable by HPLC. The reaction mixture was evaporated and the residue taken up in 90 ml ethanol. To this solution were added 12 ml ethylene diamine and the mixture stirred at ambient temperature over night. Ethyl acetate was added and the organic phase washed with water, 0.1N HCl solution and brine. The organic extract was dried over Na$_2$SO$_4$, filtered and evaporated. The residue was purified by chromatography on silica gel with ethyl acetate as eluent: 2.4 g d) 2-(3-bromo-2,6-diethyl-benzyl)-4,5-dihydro-1H-imidazole as slightly red powder; MS (ISP): 297.1 and 295.1 ((M+H)+·).

Example 33

2-(4-Methoxy-2,5-dimethyl-benzyl)-4,5-dihydro-1H-imidazole hydrochloride

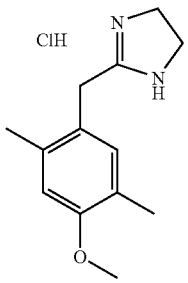

2-(4-Methoxy-2,5-dimethyl-benzyl)-4,5-dihydro-1H-imidazole was prepared from (4-methoxy-2,5-dimethyl-phenyl)-acetonitrile and ethylene diamine in analogy to Example 22; isolated as hydrochloride: colourless powder; MS (ISP): 219.1 ((M+H)$^{+\cdot}$).

Example 34

2-(2-Bromo-4,5-dimethoxy-benzyl)-4,5-dihydro-1H-imidazole hydrochloride

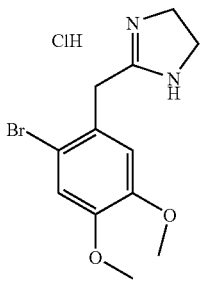

2-(2-Bromo-4,5-dimethoxy-benzyl)-4,5-dihydro-1H-imidazole was prepared from (2-bromo-4,5-dimethoxy-phenyl)-acetonitrile and ethylene diamine in analogy to Example 22; isolated as hydrochloride: colourless powder; MS (ISP): 301.0 and 299.0 ((M+H)$^{+\cdot}$).

Example 35 rac-2-(1-p-Tolyl-ethyl)-4,5-dihydro-1H-imidazole hydrochloride

rac-2-(1-p-Tolyl-ethyl)-4,5-dihydro-1H-imidazole was prepared from rac-2-p-tolyl-propionitrile and ethylene diamine in analogy to Example 22; isolated as hydrochloride: colourless crystals; MS (EI): 188.2 (M$^{+\cdot}$), 187.2 (((M-H)$^{+\cdot}$) 100%).

Example 36 rac-2-[1-(4-Methoxy-phenyl)-ethyl]-4,5-dihydro-1H-imidazole hydrochloride

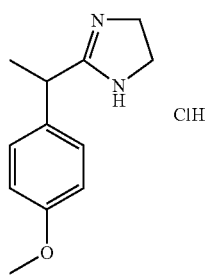

rac-2-[1-(4-Methoxy-phenyl)-ethyl]-4,5-dihydro-1H-imidazole was prepared from rac-2-(4-methoxy-phenyl)-propionitrile and ethylene diamine in analogy to Example 22; isolated as hydrochloride: off-white crystals; MS (EI): 204.3 (M$^{+\cdot}$), 203.2 (((M-H)$^{+\cdot}$), 100%).

Example 37

2-(2-Isopropoxy-3-methoxy-benzyl)-4,5-dihydro-1H-imidazole oxalate

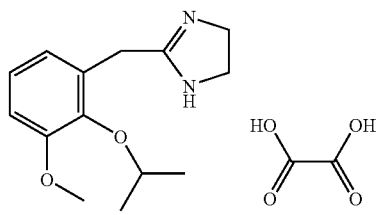

2-(2-Isopropoxy-3-methoxy-benzyl)-4,5-dihydro-1H-imidazole was prepared from (2-isopropoxy-3-methoxy-phenyl)-acetonitrile and ethylene diamine in analogy to Example 22; isolated as salt with oxalic acid: colourless platelets; MS (ISP): 249.0 ((M+H)$^{+\cdot}$).

Example 38

2-(2,6-Difluoro-benzyl)-4,5-dihydro-1H-imidazole hydrochloride

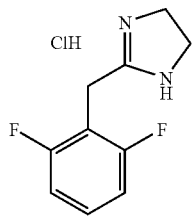

2-(2,6-Difluoro-benzyl)-4,5-dihydro-1H-imidazole was prepared from 2,6-difluoro-phenyl)-acetonitrile and ethylene diamine in analogy to Example 22; isolated as hydrochloride: colourless powder; MS (ISP): 197.0 ((M+H)$^{+\cdot}$).

Example 39

2-(2-Chloro-6-fluoro-benzyl)-4,5-dihydro-1H-imidazole hydrochloride

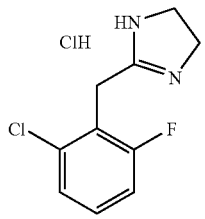

2-(2-Chloro-6-fluoro-benzyl)-4,5-dihydro-1H-imidazole was prepared from (2-chloro-6-fluoro-phenyl)-acetonitrile and ethylene diamine in analogy to Example 22; isolated as hydrochloride: colourless powder; MS (ISP): 212.9 ((M+H)$^{+\cdot}$).

Example 40

N-[4-(4,5-Dihydro-1H-imidazol-2-ylmethyl)-phenyl]-acetamide hydrochloride

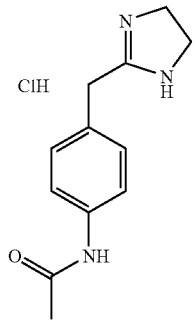

N-[4-(4,5-Dihydro-1H-imidazol-2-ylmethyl)-phenyl]-acetamide was prepared from N-(4-cyanomethyl-phenyl)-acetamide and ethylene diamine in analogy to Example 22; isolated as hydrochloride: light-brown powder; MS (ISP): 218.0 ((M+H)$^{+\cdot}$).

Example 41 rac-2-(1-Phenyl-butyl)-4,5-dihydro-1H-imidazole hydrochloride

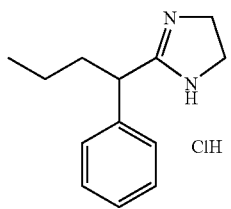

rac-2-(1-Phenyl-butyl)-4,5-dihydro-1H-imidazole was prepared from rac-2-phenyl-pentanenitrile and ethylene diamine in analogy to Example 22; isolated as hydrochloride: colourless crystals; MS (ISP): 203.2 ((M+H)$^{+\cdot}$).

Example 42

2-(2-Fluoro-6-trifluoromethyl-benzyl)-4,5-dihydro-1H-imidazole hydrochloride

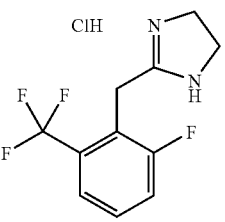

2-(2-Fluoro-6-trifluoromethyl-benzyl)-4,5-dihydro-1H-imidazole was prepared from (2-fluoro-6-trifluoromethyl-phenyl)-acetonitrile and ethylene diamine in analogy to Example 22; isolated as hydrochloride: colourless crystals; MS (ISP): 246.9 ((M+H)$^{+\cdot}$).

Example 43

2-(4-Fluoro-2-trifluoromethyl-benzyl)-4,5-dihydro-1H-imidazole hydrochloride

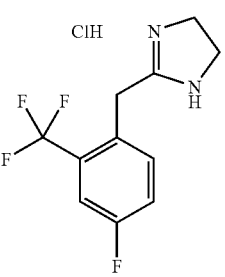

2-(4-Fluoro-2-trifluoromethyl-benzyl)-4,5-dihydro-1H-imidazole was prepared from (4-fluoro-2-trifluoromethyl-phenyl)-acetonitrile and ethylene diamine in analogy to Example 22; isolated as hydrochloride: colourless powder; MS (EI): 246.2 (M$^{+\cdot}$), 245.1 (M-H$^{+\cdot}$), 217.1 ((M-C$_2$H$_5$)$^{+\cdot}$), 177.1 (((M-imidazoline)$^{+\cdot}$), 100%).

Example 44

2-(5-Fluoro-2-methyl-benzyl)-4,5-dihydro-1H-imidazole hydrochloride

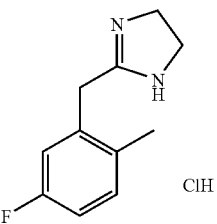

2-(5-Fluoro-2-methyl-benzyl)-4,5-dihydro-1H-imidazole was prepared from (5-fluoro-2-methyl-phenyl)-acetonitrile and ethylene diamine in analogy to Example 19 b); isolated as hydrochloride: light yellow powder; MS (ISP): 193.1 ((M+H)$^{+\cdot}$).

Example 45

2-(2-Fluoro-5-methyl-benzyl)-4,5-dihydro-1H-imidazole a) (2-Fluoro-5-methyl-phenyl)-acetonitrile

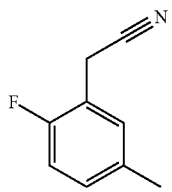

(2-Fluoro-5-methyl-phenyl)-acetonitrile was prepared from 2-bromomethyl-1-fluoro-4-methyl-benzene and sodium cyanide in presence of a catalytic amount of 15-crown-5 in acetonitrile at ambient temperature over night in analogy to R. B. Katz et al., Tetrahedron 45, 1801 (1989): light yellow liquid; MS (EI): 149.1 (M$^{+\cdot}$).

b) 2-(2-Fluoro-5-methyl-benzyl)-4,5-dihydro-1H-imidazole

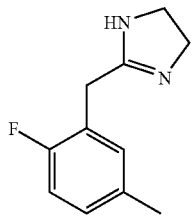

2-(2-Fluoro-5-methyl-benzyl)-4,5-dihydro-1H-imidazole was prepared from (2-fluoro-5-methyl-phenyl)-acetonitrile and ethylene diamine in analogy to Example 19 b): light yellow powder; MS (ISP): 193.0 ((M+H)$^{+\cdot}$).

Example 46

2-(2,6-Difluoro-3-methyl-benzyl)-4,5-dihydro-1H-imidazole

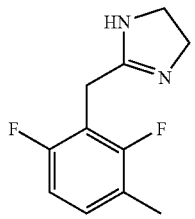

2-(2,6-Difluoro-3-methyl-benzyl)-4,5-dihydro-1H-imidazole was prepared from (2,6-difluoro-3-methyl-phenyl)-acetonitrile and ethylene diamine in analogy to Example 19 b): colourless powder; MS (ISP): 210.1 ((M+H)$^{+\cdot}$).

Example 47 rac-2-[1-(3-Fluoro-phenyl)-propyl]-4,5-dihydro-1H-imidazole

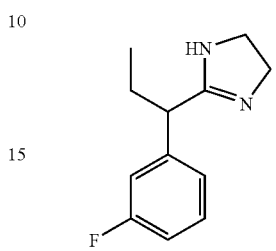

rac-2-[1-(3-Fluoro-phenyl)-propyl]-4,5-dihydro-1H-imidazole was prepared from rac-2-(3-fluoro-phenyl)-butyronitrile and ethylene diamine in analogy to Example 19 b): colourless powder; MS (ISP): 207.1 ((M+H)$^{+\cdot}$).

Example 48 rac-2-[1-(2-Fluoro-3-trifluoromethyl-phenyl)-propyl]-4,5-dihydro-1H-imidazole

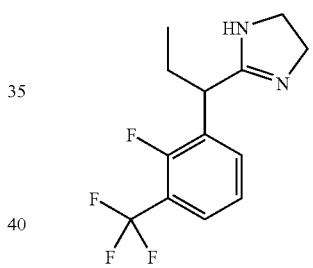

rac-2-[1-(2-Fluoro-3-trifluoromethyl-phenyl)-propyl]-4,5-dihydro-1H-imidazole was prepared from rac-2-(2-fluoro-3-trifluoromethyl-phenyl)-butyronitrile and ethylene diamine in analogy to Example 19 b): colourless powder; MS (ISP): 275.0 ((M+H)$^{+\cdot}$).

Example 49

2-(2-Trifluoromethoxy-benzyl)-4,5-dihydro-1H-imidazole

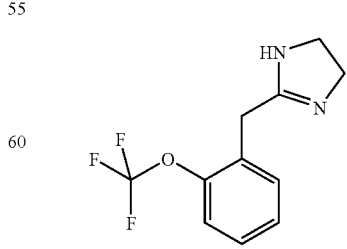

2-(2-Trifluoromethoxy-benzyl)-4,5-dihydro-1H-imidazole was prepared from (2-trifluoromethoxy-phenyl)-acetonitrile and ethylene diamine in analogy to Example 19 b): yellow powder; MS (ISP): 245.0 ((M+H)⁺·).

Example 50

2-(5-Fluoro-2-trifluoromethyl-benzyl)-4,5-dihydro-1H-imidazole

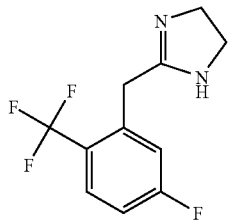

2-(5-Fluoro-2-trifluoromethyl-benzyl)-4,5-dihydro-1H-imidazole was prepared from (2-fluoro-5-trifluoromethyl-phenyl)-acetonitrile and the complex of trimethylaluminium with ethylene diamine in toluene at reflux for 18 hours in analogy to M. P. Wentland et al., J. Med. Chem. 30, 1482 (1987): brown solid; MS (ISP): 247.0 ((M+H)⁺·).

Example 51 rac-2-[1-(2-Fluoro-phenyl)-propyl]-4,5-dihydro-1H-imidazole

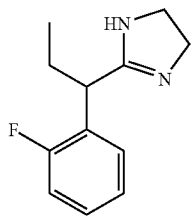

rac-2-[1-(2-Fluoro-phenyl)-propyl]-4,5-dihydro-1H-imidazole was prepared from rac-2-(2-fluoro-phenyl)-butyronitrile and ethylene diamine in analogy to Example 19 b): light yellow powder; MS (ISP): 207.0 ((M+H)⁺·).

Example 52

2-(2-Fluoro-5-trifluoromethyl-benzyl)-4,5-dihydro-1H-imidazole

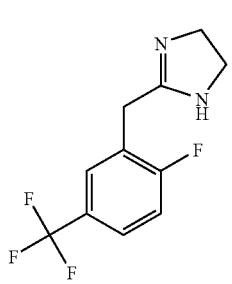

2-(2-Fluoro-5-trifluoromethyl-benzyl)-4,5-dihydro-1H-imidazole was prepared from (2-fluoro-5-trifluoromethyl-phenyl)-acetonitrile and ethylene diamine in analogy to Example 19 b): brown solid; MS (ISP): 247.3 ((M+H)⁺·).

Example 53

2-(2-Chloro-6-fluoro-3-methyl-benzyl)-4,5-dihydro-1H-imidazole

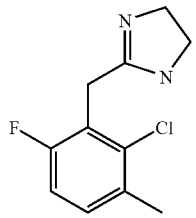

2-(2-Chloro-6-fluoro-3-methyl-benzyl)-4,5-dihydro-1H-imidazole was prepared from (2-chloro-6-fluoro-3-methylphenyl)-acetonitrile and ethylene diamine in analogy to Example 19 b): off-white solid; MS (ISP): 227.0 ((M+H)⁺·).

Example 54

2-(2-Ethyl-benzyl)-4,5-dihydro-1H-imidazole

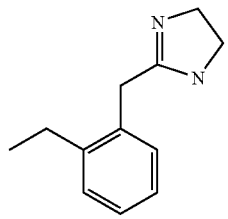

2-(2-Ethyl-benzyl)-4,5-dihydro-1H-imidazole was prepared from (2-ethylphenyl)-acetonitrile and ethylene diamine in analogy to Example 19 b): light yellow powder; MS (ISP): 189.4 ((M+H)⁺·).

Example 55

2-(2-Chloro-6-methoxy-benzyl)-4,5-dihydro-1H-imidazole

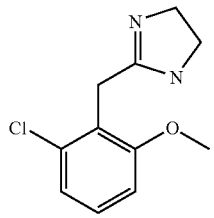

2-(2-Chloro-6-methoxy-benzyl)-4,5-dihydro-1H-imidazole was prepared from (2-chloro-6-methoxyphenyl)-acetonitrile and ethylene diamine in analogy to Example 19 b): light brown powder; MS (ISP): 224.9 ((M+H)⁺·).

Example 56

2-(2-Cyclopropyl-benzyl)-4,5-dihydro-1H-imidazole a) (2-Cyclopropyl-phenyl)-acetonitrile

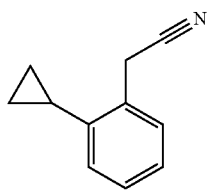

To a solution of 0.784 g (4 mmol) 2-bromophenyl-acetonitrile in 16 ml toluene were added 0.8 ml water, 0.412 g (4.8 mmol) cyclopropylboronic acid, 2.97 g (14 mmol) tribasic potassium phosphate, 0.112 g (0.4 mmol) tricyclohexylphosphine and 0.045 g (0.2 mmol) palladium(II) acetate. The reaction mixture was stirred at 100° C. for 2 days. The solvent was evaporated and the residue taken up in water and ethyl acetate. The organic layer was washed with brine, dried over MgSO$_4$, filtered and evaporated. The residue was purified using column chromatography (SiO$_2$, heptane/ethyl acetate 98:2) to yield 0.40 g of (2-cyclopropyl-phenyl)-acetonitrile as a light-yellow oil that was used directly for the next step.

b) 2-(2-Cyclopropyl-benzyl)-4,5-dihydro-1H-imidazole

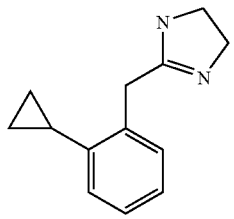

2-(2-Cyclopropyl-benzyl)-4,5-dihydro-1H-imidazole was prepared from (2-cyclopropyl-phenyl)-acetonitrile and ethylene diamine in analogy to Example 19 b): light brown powder; MS (ISP): 201.4 ((M+H)$^{+\cdot}$).

Example 57

2-(2-Bromo-6-methyl-benzyl)-4,5-dihydro-1H-imidazole

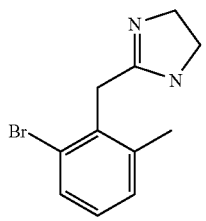

2-(2-Bromo-6-methyl-benzyl)-4,5-dihydro-1H-imidazole was prepared from (2-bromo-6-methylphenyl)-acetonitrile and ethylene diamine in analogy to Example 19 b): off-white solid;
MS (EI): 173.1 (100%); 252.2; 254.1 ((M+H)$^+$).

Example 58

2-(3-Bromo-5-methoxy-2-methyl-benzyl)-4,5-dihydro-1H-imidazole

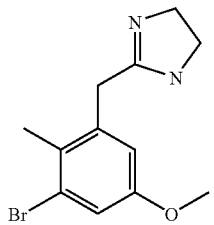

2-(3-Bromo-5-methoxy-2-methyl-benzyl)-4,5-dihydro-1H-imidazole was prepared from 3-bromo-5-methoxy-2-methyl-benzyl bromide in analogy to Example 19 a) and b): white solid; MS (ISP): 282.8; 284.8 ((M+H)$^{+\cdot}$).

Example 59

2-(2-Chloro-3-trifluoromethyl-benzyl)-4,5-dihydro-1H-imidazole

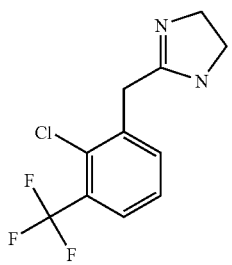

2-(2-Chloro-3-trifluoromethyl-benzyl)-4,5-dihydro-1H-imidazole was prepared from (2-chloro-3-trifluoromethylphenyl)-acetonitrile and ethylene diamine in analogy to Example 19 b): white solid; MS (ISP): 262.8 ((M+H)$^{+\cdot}$).

Example 60 rac-2-[1-(2,6-Difluoro-phenyl)-ethyl]-4,5-dihydro-1H-imidazole

rac-2-[1-(2,6-Difluoro-phenyl)-ethyl]-4,5-dihydro-1H-imidazole was prepared from rac-2-(2,6-difluoro-phenyl)-propionitrile and ethylene diamine in analogy to Example 19 b): white solid; MS (ISP): 211.1 ((M+H)$^{+\cdot}$).

Example 61 rac-2-[1-(2,5-Dichloro-phenyl)-ethyl]-4,5-dihydro-1H-imidazole

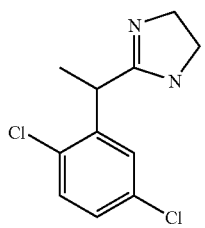

rac-2-[1-(2,5-Dichloro-phenyl)-ethyl]-4,5-dihydro-1H-imidazole was prepared from rac-2-(2,5-dichloro-phenyl)-propionitrile and ethylene diamine in analogy to Example 19 b): white solid; MS (ISP): 243.0 ((M+H)$^+$).

Example 62 rac-2-[1-(3-Bromo-phenyl)-ethyl]-4,5-dihydro-1H-imidazole

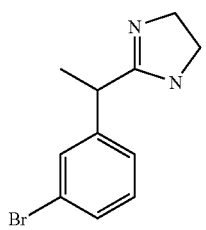

rac-2-[1-(3-Bromo-phenyl)-ethyl]-4,5-dihydro-1H-imidazole was prepared from rac-2-(3-bromo-phenyl)-propionitrile and ethylene diamine in analogy to Example 19 b): light yellow solid; MS (ISP): 252.9; 254.9 ((M+H)$^+$).

Example 63

2-(6-Chloro-2-fluoro-3-methyl-benzyl)-4,5-dihydro-1H-imidazole

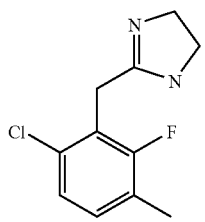

2-(6-Chloro-2-fluoro-3-methyl-benzyl)-4,5-dihydro-1H-imidazole was prepared from 6-chloro-2-fluoro-3-methyl-benzyl bromide in analogy to Example 19 a) and b): light yellow solid; MS (ISP): 227.0 ((M+H)$^+$).

Example 64

2-[2-(4-Fluoro-phenylsulfanyl)-5-methyl-benzyl]-4,5-dihydro-1H-imidazole

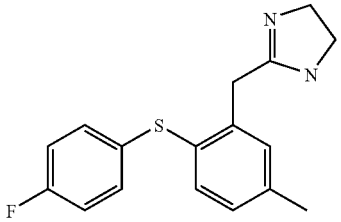

2-[2-(4-Fluoro-phenylsulfanyl)-5-methyl-benzyl]-4,5-dihydro-1H-imidazole was prepared from 2-(4-fluoro-phenylsulfanyl)-5-methyl-benzyl chloride via nitrile in analogy to Example 19 a) and Example 19 b): off-white solid; MS (ISP): 301.1 ((M+H)$^+$).

Example 65

2-[1-(2,3-Difluoro-phenyl)-ethyl]-4,5-dihydro-1H-imidazole a) rac-2-(2,3-Difluoro-phenyl)-propionitrile

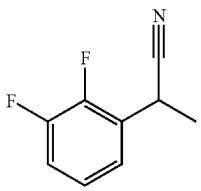

A solution of 1.586 g (16 mmol) diisopropylamine in 25 ml tetrahydrofuran was cooled with sodium chloride/ice to −10° C. A solution of 9 ml (14 mmol) 1.6 M butyl lithium in hexanes was added drop-wise. After stirring for 10 min the resulting LDA solution was cooled to −78° C. and a solution of 2.00 g (13 mmol) 2,3-difluorophenyl-acetonitrile in 5 ml tetrahydrofuran slowly added. The reaction mixture was stirred at −78° C. for 40 min, then 2.22 g (16 mmol) methyl iodide were added and the cooling bath was removed after 5 min. The mixture was stirred for 2.5 h at room temperature, and then aqueous ammonium chloride solution was added. The mixture was extracted twice with ethyl acetate. The combined organic layers were dried over MgSO$_4$, filtered and evaporated. The residue was purified using column chromatography (SiO$_2$, heptanes/ethyl acetate 9:1) to yield 1.12 g of rac-2-(2,3-difluoro-phenyl)-propionitrile as a light yellow liquid; MS (EI): 167.1 (M$^+$), 152.1 (((M-CH$_3$)$^+$), 100%).

b) rac-2-[1-(2,3-Difluoro-phenyl)-ethyl]-4,5-dihydro-1H-imidazole

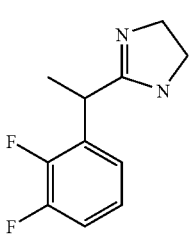

rac-2-[1-(2,3-Difluoro-phenyl)-ethyl]-4,5-dihydro-1H-imidazole was prepared from rac-2-(2,3-difluoro-phenyl)-propionitrile and ethylene diamine in analogy to Example 19 b): off-white solid; MS (EI): 210.1 ((M+H)$^{+\cdot}$).

Example 66 rac-2-[1-(2-Bromo-phenyl)-ethyl]-4,5-dihydro-1H-imidazole

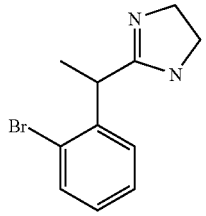

rac-2-[1-(2-Bromo-phenyl)-ethyl]-4,5-dihydro-1H-imidazole was prepared from rac-2-(2-bromo-phenyl)-propionitrile and ethylene diamine in analogy to Example 19 b): off-white solid; MS (EI): 251.0 and 253.0 (M$^{+\cdot}$), 173.1 (((M-Br)$^{+\cdot}$), 100%).

Example 67 rac-2-[1-(2-Iodo-phenyl)-ethyl]-4,5-dihydro-1H-imidazole

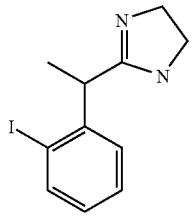

rac-2-[1-(2-Iodo-phenyl)-ethyl]-4,5-dihydro-1H-imidazole was prepared from rac-2-(2-iodo-phenyl)-propionitrile and ethylene diamine in analogy to Example 19 b): white solid; MS (EI): 301.0 ((M+H)$^{+\cdot}$).

Example 68

2-[2-(4-Chloro-phenylsulfanyl)-benzyl]-4,5-dihydro-1H-imidazole

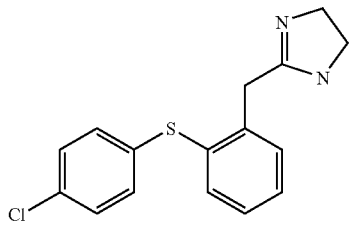

2-[2-(4-Chloro-phenylsulfanyl)-benzyl]-4,5-dihydro-1H-imidazole was prepared from 2-(4-chloro-phenylsulfanyl)-phenyl-acetonitrile and ethylene diamine in analogy to Example 19 b): white solid; MS (EI): 302.9 ((M+H)$^{+\cdot}$).

Example 69 rac-2-[1-(2-Ethyl-phenyl)-ethyl]-4,5-dihydro-1H-imidazole a) rac-2-(2-Ethyl-phenyl)-propionitrile

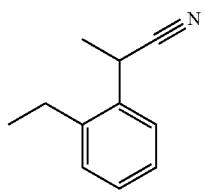

rac-2-(2-Ethyl-phenyl)-propionitrile was prepared from (2-ethyl-phenyl)-acetonitrile and methyl iodide in analogy to Example 65a): light-yellow liquid; MS (EI): 159.1 (M$^{+\cdot}$).

b) rac-2-[1-(2-Ethyl-phenyl)-ethyl]-4,5-dihydro-1H-imidazole

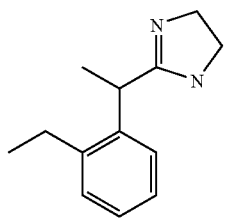

rac-2-[1-(2-Ethyl-phenyl)-ethyl]-4,5-dihydro-1H-imidazole was prepared from rac-2-(2-ethyl-phenyl)-propionitrile and ethylene diamine in analogy to Example 19 b): off-white solid;
MS (EI): 203.1 ((M+H)$^{+\cdot}$).

Example 70

Procedure C (a)

2-(2,6-Diethyl-benzyl)-1H-imidazole

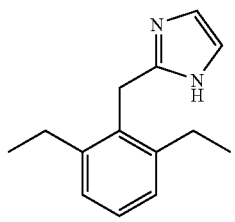

a) To a solution of 1.08 g (14 mmol) dimethylsulfoxide in 100 ml dichloromethane cooled to –78° C. was added a solution of 1.82 g (14 mmol) oxalyl chloride in 7 ml dichloromethane. The mixture was stirred for 50 minutes at –78° C. and then a solution of 0.620 g (3 mmol) 2-(2,6-diethyl-benzyl)-4,5-dihydro-1H-imidazole in 80 ml dichloromethane was added and stirring continued at −78° C. for 90 minutes. Then 2.90 g triethylamine were added and the reaction mixture warmed to ambient temperature and stirring continued for 2 hours. Concentrated ammonia was added and the reaction mixture extracted with ethyl acetate, the combined extracts washed with brine, dried over $Na_2SO_4$, filtered and evaporated. Purification on silica gel by flash-chromatography with a heptane/ethyl acetate gradient followed by trituration of residue of the collected and evaporated fractions in tert.-butyl methyl ether provided 0.475 g 2-(2,6-diethyl-benzyl)-1H-imidazole as colourless solid: MS (ISP): 215.2 ((M+H)$^{+}$).

In analogy to Example 70 a) were prepared Examples 71 to 80, 97 to 103, 110, 111, 177 to 179, 181, 182, 184 and 200.

Procedure C (c)

b) To a solution of 90 mg (0.39 mmol) (2,6-diethyl-phenyl)-(1H-imidazol-2-yl)-methanol (Example 96) in 2 ml concentrated aqueous HCl solution were added 500 mg zinc foil and heated to reflux for 20 hours. Then the mixture was cooled to ambient temperature, aqueous sodium hydroxide solution added, the turbid solution filtered and the filtrate extracted with ethyl acetate. The combined extracts were washed with brine, dried over $Na_2SO_4$, filtered and evaporated. 2-(2,6-Diethyl-benzyl)-1H-imidazole was obtained as off-white solid: MS (EI): 214.3 (M$^{+\cdot}$).

Example 71

2-(2,3,5,6-Tetramethyl-benzyl)-1H-imidazole

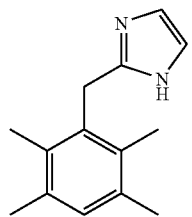

2-(2,3,5,6-Tetramethyl-benzyl)-1H-imidazole was prepared from 2-(2,3,5,6-Tetramethyl-benzyl)-4,5-dihydro-1H-imidazole in analogy to Example 70 a): light-yellow solid; MS (EI): 214.2 (M$^{+\cdot}$), 199.2 (((M-CH$_3$)$^{+\cdot}$), 100%).

Example 72

2-Pentamethylphenylmethyl-1H-imidazole

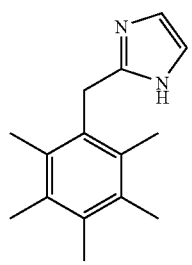

2-Pentamethylphenylmethyl-1H-imidazole was prepared from 2-pentamethylphenylmethyl-4,5-dihydro-1H-imidazole in analogy to Example 70 a): light-yellow solid; MS (EI): 228.2 (M$^{+\cdot}$), 213.2 (((M-CH$_3$)$^{+\cdot}$), 100%).

Example 73

2-(4-Methoxy-2,6-dimethyl-benzyl)-1H-imidazole

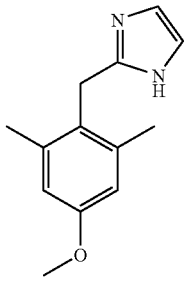

2-(4-Methoxy-2,6-dimethyl-benzyl)-1H-imidazole was prepared from 2-(4-methoxy-2,6-dimethyl-benzyl)-4,5-dihydro-1H-imidazole in analogy to Example 70 a): light-brown solid; MS (EI): 216.2 (M$^{+\cdot}$).

Example 74

2-(2,5-Dimethyl-benzyl)-1H-imidazole

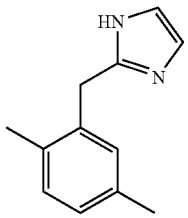

2-(2,5-Dimethyl-benzyl)-1H-imidazole was prepared from 2-(2,5-dimethyl-benzyl)-4,5-dihydro-1H-imidazole in analogy to Example 70 a): colourless solid; MS (EI): 186.1 (M$^{+\cdot}$).

Example 75

2-(4-Fluoro-2,6-dimethyl-benzyl)-1H-imidazole

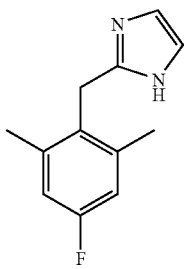

2-(4-Fluoro-2,6-dimethyl-benzyl)-1H-imidazole was prepared from 2-(4-fluoro-2,6-dimethyl-benzyl)-4,5-dihydro-1H-imidazole in analogy to Example 70 a): light-brown solid; MS (EI): 204.1 (M+·).

Example 76

2-(2,6-Dimethyl-benzyl)-5-methyl-1H-imidazole

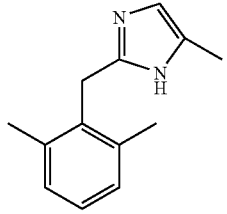

2-(2,6-Dimethyl-benzyl)-5-methyl-1H-imidazole was prepared from 2-(2,6-dimethyl-benzyl)-5-methyl-4,5-dihydro-1H-imidazole in analogy to Example 70 a): colourless solid; MS (ISP): 201.1 ((M+H)+·).

Example 77

2-(3-Bromo-2,6-diethyl-benzyl)-1H-imidazole

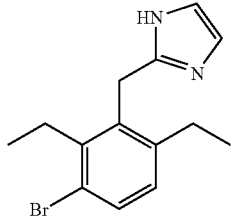

2-(3-Bromo-2,6-diethyl-benzyl)-1H-imidazole was prepared from 2-(3-bromo-2,6-diethyl-benzyl)-4,5-dihydro-1H-imidazole in analogy to Example 70 a): off-white solid; MS (EI): 294.2 and 292.1 (M+·), 265.1 and 263.0 ((M-C₂H₅)+·), 213.2 (((M-Br)+·) 100%).

Example 78

2-(5-Fluoro-2-methyl-benzyl)-1H-imidazole

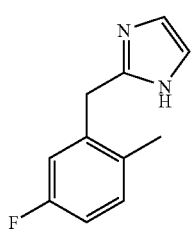

2-(5-Fluoro-2-methyl-benzyl)-1H-imidazole was prepared from 2-(5-fluoro-2-methyl-benzyl)-4,5-dihydro-1H-imidazole in analogy to Example 70 a): off-white solid; MS (ISP): 191.2 ((M+H)+·).

Example 79

2-(2-Fluoro-5-methyl-benzyl)-1H-imidazole

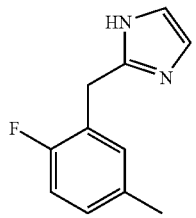

2-(2-Fluoro-5-methyl-benzyl)-1H-imidazole was prepared from 2-(2-fluoro-5-methyl-benzyl)-4,5-dihydro-1H-imidazole in analogy to Example 70 a): light-brown solid; MS (EI): 190.1 (M+·).

Example 80

2-(2,6-Difluoro-3-methyl-benzyl)-1H-imidazole

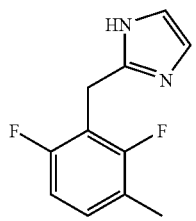

2-(2,6-Difluoro-3-methyl-benzyl)-1H-imidazole was prepared from 2-(2,6-difluoro-3-methyl-benzyl)-4,5-dihydro-1H-imidazole in analogy to Example 70 a): colourless solid; MS (EI): 208.2 (M+·), 193.1 ((M-CH₃)+), 189.1 (((M-F)+·) 100%).

Procedure C (b)

Example 81 rac-2-[1-(4-Chloro-phenyl)-propyl]-1H-imidazole

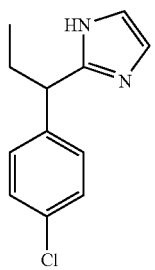

0.79 g (5 mmol) Potassium permanganate and 1.25 g silica were ground together in a mortar until a fine homogenous powder was obtained. This powder was added to a suspension of 0.37 g, (1.7 mmol) rac-2-[1-(4-chloro-phenyl)-propyl]-4,5-dihydro-1H-imidazole in 25 ml acetonitrile and the reaction mixture was stirred at ambient temperature for 16 hours. Ethanol was added to the reaction mixture to reduce excess oxidant. The mixture was filtered and the solid obtained, was washed with acetonitrile. The filtrate was evaporated in vacuo to afford 0.27 g amorphous solid. A portion of the crude material (100 mg) was purified by preparative HPLC to afford 38 mg (27%) rac-2-[1-(4-chloro-phenyl)-propyl]-1H-imidazole as colourless solid; MS (ISP): 221.0 ((M+H)$^{+\cdot}$).

In analogy to Example 81 were prepared Examples 82 to 95.

Example 82 rac-2-(1-Phenyl-propyl)-1H-imidazole

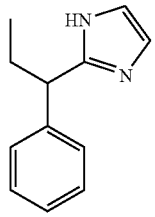

rac-2-(1-Phenyl-propyl)-1H-imidazole was prepared from rac-2-(1-phenyl-propyl)-4,5-dihydro-1H-imidazole in analogy to Example 81: off-white solid; MS (ISP): 187.1 ((M+H)$^{+\cdot}$).

Example 83 rac-2-[1-(3-Chloro-phenyl)-propyl]-1H-imidazole

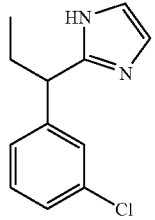

rac-2-[1-(3-Chloro-phenyl)-propyl]-1H-imidazole was prepared from rac-2-[1-(3-chloro-phenyl)-propyl]-4,5-dihydro-1H-imidazole in analogy to Example 81: off-white solid; MS (ISP): 221.0 ((M+H)$^{+\cdot}$).

Example 84 rac-2-(1-p-Tolyl-propyl)-1H-imidazole

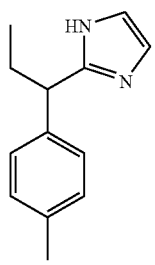

rac-2-(1-p-Tolyl-propyl)-1H-imidazole was prepared from rac-2-(1-p-tolyl-propyl)-4,5-dihydro-1H-imidazole in analogy to Example 81: off-white solid; MS (ISP): 201.1 ((M+H)$^{+\cdot}$).

Example 85 rac-2-(1-Phenyl-ethyl)-1H-imidazole

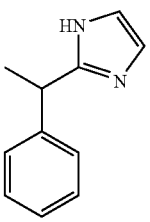

rac-2-(1-Phenyl-ethyl)-1H-imidazole was prepared from rac-2-(1-phenyl-ethyl)-4,5-dihydro-1H-imidazole in analogy to Example 81: off-white solid; MS (ISP): 173.1 ((M+H)$^{+\cdot}$).

Example 86 rac-2-[1-(3-Bromo-phenyl)-propyl]-1H-imidazole

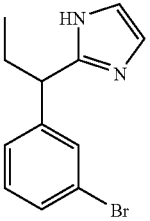

rac-2-[1-(3-Bromo-phenyl)-propyl]-1H-imidazole was prepared from rac-2-[1-(3-bromo-phenyl)-propyl]-4,5-dihydro-1H-imidazole in analogy to Example 81: off-white solid; MS (ISP): 267.1 and 265.0 ((M+H)$^{+\cdot}$).

Example 87 rac-2-[1-(3-Fluoro-phenyl)-propyl]-1H-imidazole

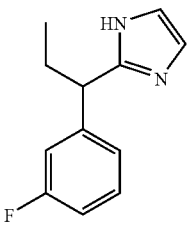

rac-2-[1-(3-Fluoro-phenyl)-propyl]-1H-imidazole was prepared from rac-2-[1-(3-fluoro-phenyl)-propyl]-4,5-dihydro-1H-imidazole in analogy to Example 81: off-white solid; MS (ISP): 205.0 ((M+H)$^{+\cdot}$).

Example 88 rac-2-[1-(2-Fluoro-3-trifluoromethyl-phenyl)-propyl]-1H-imidazole

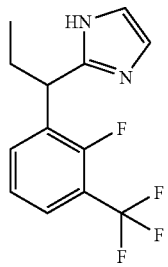

rac-2-[1-(2-Fluoro-3-trifluoromethyl-phenyl)-propyl]-1H-imidazole was prepared from rac-2-[1-(2-fluoro-3-trifluoromethyl-phenyl)-propyl]-4,5-dihydro-1H-imidazole in analogy to Example 81: off-white solid; MS (ISP): 273.0 ((M+H)$^{+\cdot}$).

Example 89 rac-2-[1-(2-Fluoro-phenyl)-propyl]-1H-imidazole

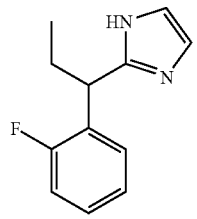

rac-2-[1-(2-Fluoro-phenyl)-propyl]-1H-imidazole was prepared from rac-2-[1-(2-fluoro-phenyl)-propyl]-4,5-dihydro-1H-imidazole in analogy to Example 81: off-white solid; MS (ISP): 205.1 ((M+H)$^{+\cdot}$).

Example 90 rac-2-[1-(3-Trifluoromethyl-phenyl)-propyl]-1H-imidazole

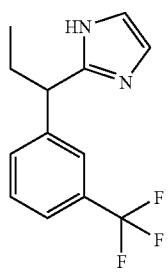

rac-2-[1-(3-Trifluoromethyl-phenyl)-propyl]-1H-imidazole was prepared from rac-2-[1-(3-trifluoromethyl-phenyl)-propyl]-4,5-dihydro-1H-imidazole in analogy to Example 81: off-white solid; MS (ISP): 255.1 ((M+H)$^{+\cdot}$).

Example 91 rac-2-[1-(4-Fluoro-phenyl)-propyl]-1H-imidazole

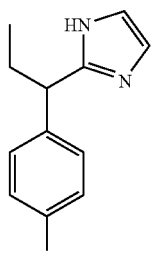

rac-2-[1-(4-Fluoro-phenyl)-propyl]-1H-imidazole was prepared from rac-2-[1-(4-fluoro-phenyl)-propyl]-4,5-dihydro-1H-imidazole in analogy to Example 81: off-white solid; MS (ISP): 205.1 ((M+H)$^{+\cdot}$).

Example 92 rac-2-[1-(2,3-Difluoro-phenyl)-propyl]-1H-imidazole

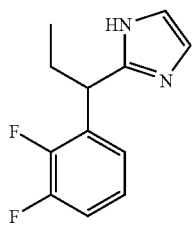

rac-2-[1-(2,3-Difluoro-phenyl)-propyl]-1H-imidazole was prepared from rac-2-[1-(2,3-difluoro-phenyl)-propyl]-4,5-dihydro-1H-imidazole in analogy to Example 81: off-white solid; MS (ISP): 223.0 ((M+H)$^{+\cdot}$).

Example 93 rac-2-[1-(2,5-Difluoro-phenyl)-propyl]-1H-imidazole

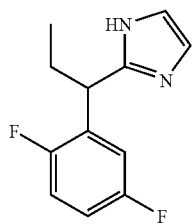

rac-2-[1-(2,5-Difluoro-phenyl)-propyl]-1H-imidazole was prepared from rac-2-[1-(2,5-difluoro-phenyl)-propyl]-4, 5-dihydro-1H-imidazole in analogy to Example 81: off-white solid;MS (ISP): 223.0 ((M+H)+·).

Example 94 rac-2-(1-Phenyl-butyl)-1H-imidazole

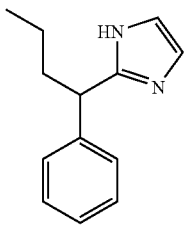

rac-2-(1-Phenyl-butyl)-1H-imidazole was prepared from rac-2-(1-phenyl-butyl)-4,5-dihydro-1H-imidazole in analogy to Example 81: colourless solid; MS (ISP): 201.0 ((M+H)+·).

Example 95 rac-2-[1-(4-Trifluoromethyl-phenyl)-propyl]-1H-imidazole

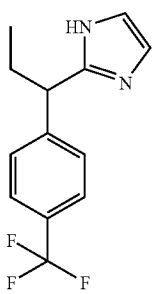

rac-2-[1-(4-Trifluoromethyl-phenyl)-propyl]-1H-imidazole was prepared from rac-2-[1-(4-trifluoromethyl-phenyl)-propyl]-4,5-dihydro-1H-imidazole in analogy to Example 81: colourless solid; MS (ISP): 255.1 ((M+H)+·).

Procedure D

Example 96 rac-(2,6-Diethyl-phenyl)-(1H-imidazol-2-yl)-methanol

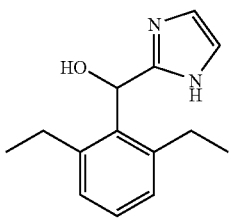

To a solution cooled to −78° C. of 2.1 g (12 mmol) 1,1-diethoxymethyl-1H-imidazole in 25 ml tetrahydrofuran were added drop-wise 8.09 ml (13 mmol) of a 1.6M butyl lithium solution in hexane. The mixture was stirred at −78° C. for 15 min. and then was added a solution of 2.00 g (12 mmol) 2,6-diethyl-benzaldehyde in 2 ml tetrahydrofuran. The mixture was stirred at −78° C. for 30 min., at −20° C. for 30 min. and at 0° C. also for 30 min. The reaction was quenched by addition of 10% aq. HCl solution and stirred at rt over night. Solid potassium carbonate was added to the mixture and the alkaline solution extracted with ethyl acetate. The combined extracts were washed with brine, dried over $Na_2SO_4$, filtered and evaporated. Trituration of the residue in ethyl acetate provided rac-(2,6-diethyl-phenyl)-(1H-imidazol-2-yl)-methanol as colourless crystals;MS (ISP): 230.9 ((M+H)+·).

Example 97

2-[1-(2-Chloro-phenyl)-ethyl]-1H-imidazole

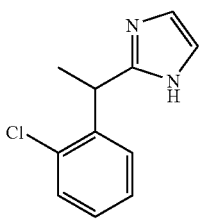

2-[1-(2-Chloro-phenyl)-ethyl]-1H-imidazole was prepared from 2-[1-(2-chloro-phenyl)-ethyl]-4,5-dihydro-1H-imidazole in analogy to Example 70 a): white solid; MS (EI): 205.2 (M+·), 171.1 (((M-Cl)+·), 100%).

Example 98

2-(2-Cyclopropyl-benzyl)-1H-imidazole

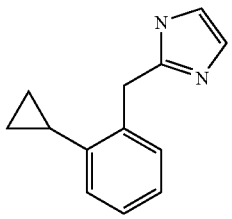

2-(2-Cyclopropyl-benzyl)-1H-imidazole was prepared from 2-(2-cyclopropyl-benzyl)-4,5-dihydro-1H-imidazole in analogy to Example 70 a): yellow solid; MS (ISP): 199.1 ((M+H)+·).

Example 99

2-(2-Bromo-6-methyl-benzyl)-1H-imidazole

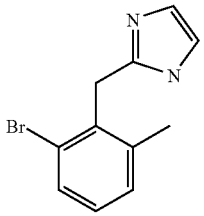

2-(2-Bromo-6-methyl-benzyl)-1H-imidazole was prepared from 2-(2-bromo-6-methyl-benzyl)-4,5-dihydro-1H-imidazole in analogy to Example 70 a): light brown solid; MS (EI): 250,1; 252.1 (M$^{+\cdot}$), 171.1 (((M-Br)$^{+\cdot}$), 100%).

Example 100 rac-2-[1-(2,5-Dichloro-phenyl)-ethyl]-1H-imidazole

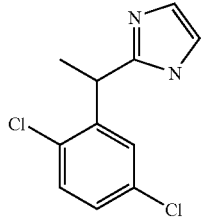

rac-2-[1-(2,5-Dichloro-phenyl)-ethyl]-1H-imidazole was prepared from rac-2-[1-(2,5-dichloro-phenyl)-ethyl]-4,5-dihydro-1H-imidazole in analogy to Example 70 a): white solid; MS (EI): 241.0 (M$^{+\cdot}$), 205.1 (((M-Cl)$^{+\cdot}$), 100%).

Example 101 rac-2-[1-(3-Bromo-phenyl)-ethyl]-1H-imidazole

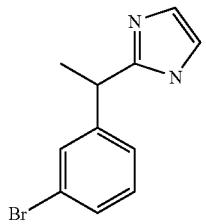

rac-2-[1-(3-Bromo-phenyl)-ethyl]-1H-imidazole was prepared from rac-2-[1-(3-bromo-phenyl)-ethyl]-4,5-dihydro-1H-imidazole in analogy to Example 70 a): white solid; MS (EI): 250.0; 252.0 (M$^{+\cdot}$), 249.0; 251.0 (((M-H)$^{+\cdot}$).

Example 102 rac-2-[1-(2-Bromo-phenyl)-ethyl]-1H-imidazole

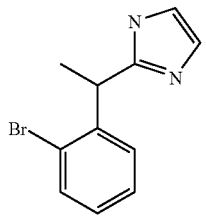

rac-2-[1-(2-Bromo-phenyl)-ethyl]-1H-imidazole was prepared from rac-2-[1-(2-bromo-phenyl)-ethyl]-4,5-dihydro-1H-imidazole in analogy to Example 70 a): white solid; MS (EI): 249.0; 251.1 (M$^{+\cdot}$), 171.1 (((M-Br)$^{+\cdot}$), 100%).

Example 103 rac-2-[1-(2-Ethyl-phenyl)-ethyl]-1H-imidazole

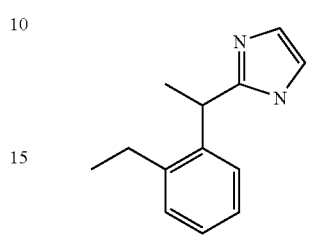

rac-2-[1-(2-Ethyl-phenyl)-ethyl]-1H-imidazole was prepared from rac-2-[1-(2-ethyl-phenyl)-ethyl]-4,5-dihydro-1H-imidazole in analogy to Example 70 a): white solid; MS (EI): 200.1 (M$^{+\cdot}$), 171.1 (((M-C$_2$H$_5$)$^{+\cdot}$), 100%).

Example 104

2-(4-Bromo-naphthalen-1-ylmethyl)-4,5-dihydro-1H-imidazole

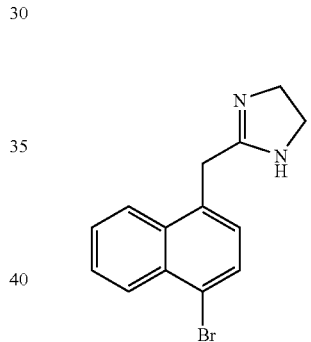

2-(4-Bromo-naphthalen-1-ylmethyl)-4,5-dihydro-1H-imidazole was prepared from (4-bromo-naphthalen-1-yl)-acetonitrile in analogy to Example 17 but heated to 150° C. for 6 hours: colourless solid, m.p. 133-135° C.; MS (EI): 290.1 and 288.0 (M$^{+\cdot}$), 289.1 and 287.0 (((M-H)$^{+\cdot}$), 100%).

Example 105

2-(7-Methyl-benzofuran-6-ylmethyl)-4,5-dihydro-1H-imidazole a) 7-Bromomethyl-6-methyl-benzofuran and 6-Bromomethyl-7-methyl-benzofuran 7-Bromomethyl-6-methyl-benzofuran and 6-bromomethyl-7-methyl-benzofuran were obtained by bromination of 6,7-dimethyl-benzofuran with NBS in presence of a catalytic amount of 2,2'-azobis(2-methylpropionitrile) in carbon tetrachloride under irradiation with a 300 W lamp and at reflux for 40 min. Distillation by Kugelrohr provided a colourless semi-solid of b.p. 150° C./3 mbar. The product mixture was directly used for the following step.

b) (7-Methyl-benzofuran-6-yl)-acetonitrile and (6-Methyl-benzofuran-7-yl)-acetonitrile

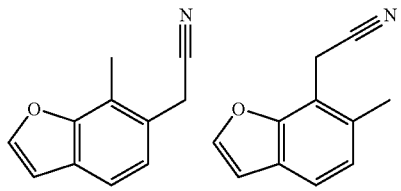

(7-Methyl-benzofuran-6-yl)-acetonitrile and (6-methyl-benzofuran-7-yl)-acetonitrile were obtained by reaction of mixture described in Example 105 a) with sodium cyanide and a catalytic amount of sodium iodide in acetone at ambient temperature over night. The mixture of regioisomers was separated by preparative HPLC on a CombiHTxDB-C18 column. (7-Methyl-benzofuran-6-yl)-acetonitrile: colourless crystals: $^1$H-NMR (CDCl$_3$): 2.53 s, 3H(C(7) -CH$_3$), 3.78 s, 2H(CH$_2$—CN), 6.75 d, J=1.8 Hz, 1H(C(3)-H), 7.22 d, J=6.0 Hz, 1H(C(5)-H), 7.43 d, J=6.0 Hz, 1H(C(4)-H), 7.64 d, J=1.8 Hz, 1H(C(2)-H); MS (EI): 171.2 (M$^{+\cdot}$). (6-Methyl-benzofuran-7-yl)-acetonitrile: light yellow oil: $^1$H-NMR (CDCl$_3$): 2.52 s, 3H(C(6) -CH$_3$), 3.97 s,2H(CH$_2$—CN), 6.75 d, J=1.8 Hz, 1H(C(3)-H), 7.11 d, J=6.0 Hz, 1H(C(5)-H), 7.46 d, J=6.0 Hz, 1H(C(4)-H), 7.61 d, J=1.8 Hz, 1H(C(2)-H); MS (EI): 171.1 (M$^{+\cdot}$).

c) 2-(7-Methyl-benzofuran-6-ylmethyl)-4,5-dihydro-1H-imidazole

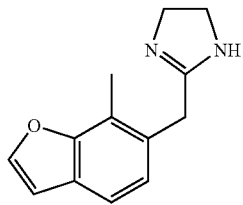

2-(7-Methyl-benzofuran-6-ylmethyl)-4,5-dihydro-1H-imidazole was prepared from (7-methyl-benzofuran-6-yl)-acetonitrile in analogy to Example 17: light brown solid; MS (ISP): 215.4 ((M+H)$^{+\cdot}$).

Example 106

2-(6-Methyl-benzofuran-7-ylmethyl)-4,5-dihydro-1H-imidazole

2-(6-Methyl-benzofuran-7-ylmethyl)-4,5-dihydro-1H-imidazole was prepared from (6-methyl-benzofuran-7-yl)-acetonitrile in analogy to Example 17: colourless crystalline solid; MS (EI): 214.2 (M$^{+\cdot}$).

Example 107

2-Benzofuran-7-ylmethyl-4,5-dihydro-1H-imidazole

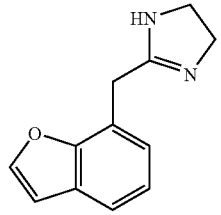

2-Benzofuran-7-ylmethyl-4,5-dihydro-1H-imidazole was prepared from benzofuran-7-yl-acetonitrile in analogy to Example 17: light brown oil; MS (EI): 200.1 (M$^{+\cdot}$).

Example 108

2-Benzofuran-3-ylmethyl-4,5-dihydro-1H-imidazole hydrochloride

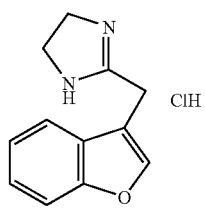

2-Benzofuran-3-ylmethyl-4,5-dihydro-1H-imidazole was prepared from benzofuran-3-yl-acetonitrile in analogy to Example 17; isolated as hydrochloride: off-white solid; MS (EI): 200.1 (M$^{+\cdot}$).

Example 109

2-(2,4,5-Trimethyl-thiophen-3-ylmethyl)-4,5-dihydro-1H-imidazole

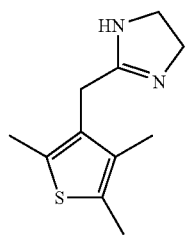

2-(2,4,5-Trimethyl-thiophen-3-ylmethyl)-4,5-dihydro-1H-imidazole was prepared from (2,4,5-trimethyl-thiophen-3-yl)-acetonitrile in analogy to Example 19 b); yellow solid; MS (ISP): 208.9 ((M+H)$^{+\cdot}$).

Example 110

2-(2,4,5-Trimethyl-thiophen-3-ylmethyl)-1H-imidazole

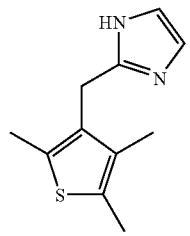

2-(2,4,5-Trimethyl-thiophen-3-ylmethyl)-1H-imidazole was prepared from (2-(2,4,5-trimethyl-thiophen-3-ylmethyl)-4,5-dihydro-1H-imidazole in analogy to Example 70 a); light yellow solid; MS (EI): 206.2 ($M^{+\cdot}$).

Example 111

2-Thiophen-2-ylmethyl-1H-imidazole

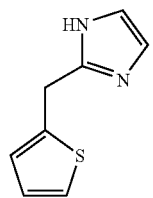

2-Thiophen-2-ylmethyl-1H-imidazole was prepared from 2-thiophen-2-ylmethyl-4,5-dihydro-1H-imidazole in analogy to Example 70 a); light yellow solid; MS (EI): 164.1 ($M^{+\cdot}$).

Example 112

2-(2,6-Diethyl-3-tritio-benzyl)-1H-imidazole cf. Example 70 for unlabeled cpd.; starting material cf. Example 77

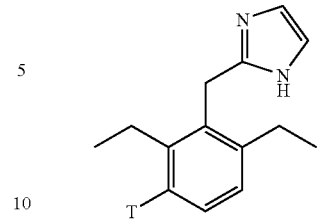

2-(2,6-Diethyl-3-tritio-benzyl)-1H-imidazole was prepared from 2-(3-bromo-2,6-diethyl-benzyl)-1H-imidazole by catalytic hydrogenation with tritium gas: >97% radiochemical purity, specific activity 25.9 Ci/mmol.

Example 113

4-Tritio-2-naphthalen-1-ylmethyl-4,5-dihydro-1H-imidazole cf. Example 140 for unlabeled cpd.; starting material cf. Example 104

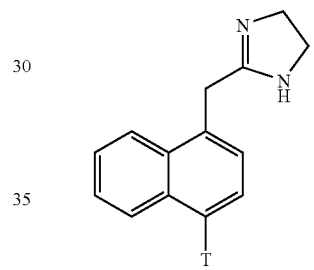

4-Tritio-2-naphthalen-1-ylmethyl-4,5-dihydro-1H-imidazole was prepared from 2-(4-bromo-naphthalen-1-ylmethyl)-4,5-dihydro-1H-imidazole by catalytic hydrogenation with tritium gas: >98% radiochemical purity, specific activity 20.7 Ci/mmol.

Known compounds:

Prepared following PROCEDURE A or B and for 2-imidazoles oxidation of corresponding 2-imidazoline following PROCEDURE C:

| Example No. | Structure | Name |
|---|---|---|
| 114 | ![structure] | 2-(4-tert-Butyl-2,6-dimethyl-benzyl)-4,5-dihydro-1H-imidazole, Xylometazoline |

-continued

| Example No. | Structure | Name |
|---|---|---|
| 115 | 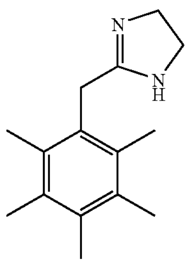 | 2-Pentamethylphenylmethyl-4,5-dihydro-1H-imidazole |
| 116 | 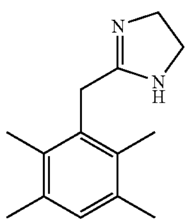 | 2-(2,3,5,6-Tetramethyl-benzyl)-4,5-dihydro-1H-imidazole |
| 117 | ClH | 6-tert-Butyl-3-(4,5-dihydro-1H-imidazol-2-ylmethyl)-2,4-dimethyl-phenol, Oxymethazoline |
| 118 | 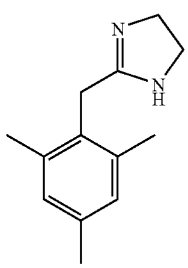 | 2-(2,4,6-Trimethyl-benzyl)-4,5-dihydro-1H-imidazole, Trimizoline |
| 119 | 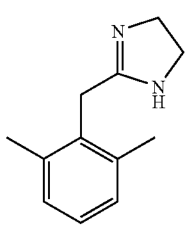 | 2-(2,6-Dimethyl-benzyl)-4,5-dihydro-1H-imidazole |
| 120 | ClH | 2-(2,6-Dichloro-benzyl)-4,5-dihydro-1H-imidazole |
| 121 | 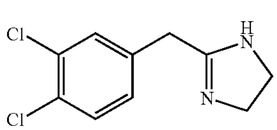 | 2-(3,4-Dichloro-benzyl)-4,5-dihydro-1H-imidazole |

-continued

| Example No. | Structure | Name |
|---|---|---|
| 122 | 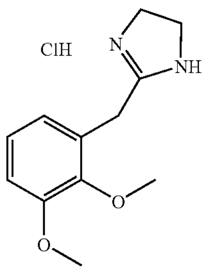 | 2-(2,3-Dimethoxy-benzyl)-4,5-dihydro-1H-imidazole |
| 123 | 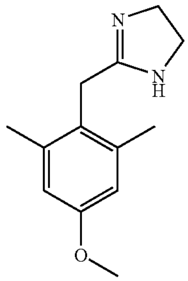 | 2-(4-Methoxy-2,6-dimethyl-benzyl)-4,5-dihydro-1H-imidazole |
| 124 | 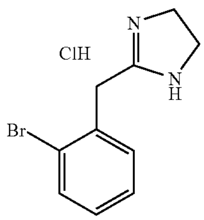 | 2-(2-Bromo-benzyl)-4,5-dihydro-1H-imidazole |
| 125 | 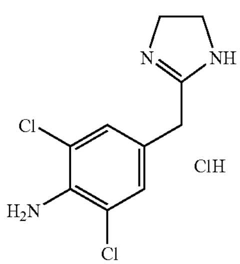 | 2,6-Dichloro-4-(4,5-dihydro-1H-imidazol-2-ylmethyl)-phenylamine, Nemazoline |
| 126 | 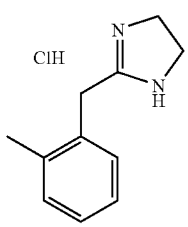 | 2-(2-Methyl-benzyl)-4,5-dihydro-1H-imidazole |
| 127 | 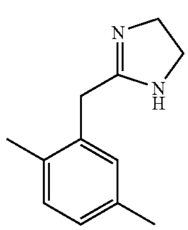 | 2-(2,5-Dimethyl-benzyl)-4,5-dihydro-1H-imidazole |

-continued

| Example No. | Structure | Name |
|---|---|---|
| 128 | 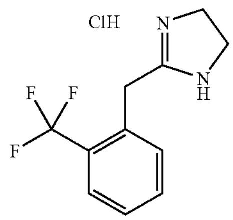 | 2-(2-Trifluoromethyl-benzyl)-4,5-dihydro-1H-imidazole |
| 129 | 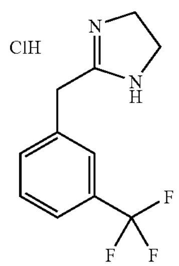 | 2-(3-Trifluoromethyl-benzyl)-4,5-dihydro-1H-imidazole |
| 130 | 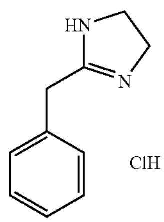 | 2-Benzyl-4,5-dihydro-1H-imidazole hydrochloride, Priscol, Tolazoline |
| 131 | 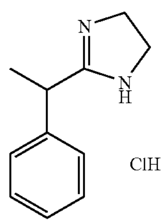 | rac-2-(1-Phenyl-ethyl)-4,5-dihydro-1H-imidazole |
| 132 | 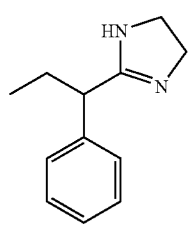 | rac-2-(1-Phenyl-propyl)-4,5-dihydro-1H-imidazole |
| 133 | 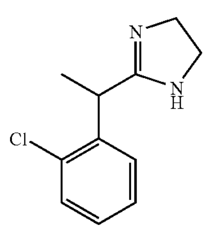 | rac-2-[1-(2-Chloro-phenyl)-ethyl]-4,5-dihydro-1H-imidazole |

-continued
| Example No. | Structure | Name |
|---|---|---|
| 134 | 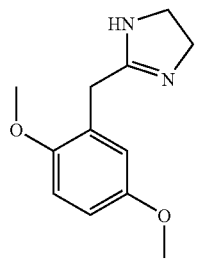 | 2-(2,5-Dimethoxy-benzyl)-4,5-dihydro-1H-imidazole |
| 135 | 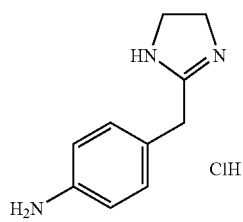 | 4-(4,5-Dihydro-1H-imidazol-2-ylmethyl)-phenylamine |
| 136 | 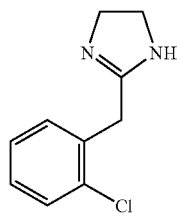 | 2-(2-Chloro-benzyl)-4,5-dihydro-1H-imidazole |
| 137 | 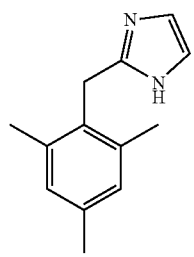 | 2-(2,4,6-Trimethyl-benzyl)-1H-imidazole |
| 138 | 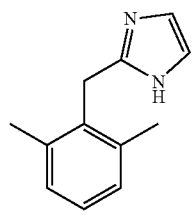 | 2-(2,6-Dimethyl-benzyl)-1H-imidazole |
| 139 | 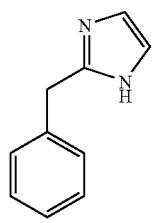 | 2-Benzyl-1H-imidazole |

-continued

| Example No. | Structure | Name |
|---|---|---|
| 140 | 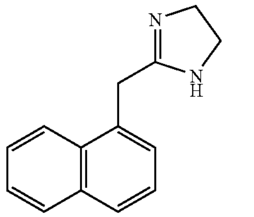 | 2-Naphthalen-1-ylmethyl-4,5-dihydro-1H-imidazole, Privine |
| 141 | 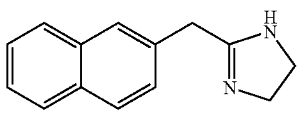 | 2-Naphthalen-2-ylmethyl-4,5-dihydro-1H-imidazole |
| 142 | 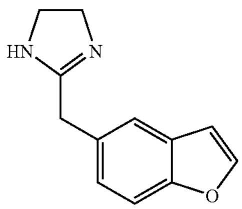 | 2-Benzofuran-5-ylmethyl-4,5-dihydro-1H-imidazole |
| 143 | 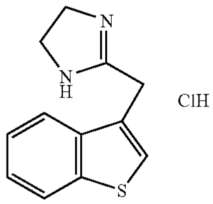 | 2-Benzo[b]thiophen-3-ylmethyl-4,5-dihydro-1H-imidazole |
| 144 | 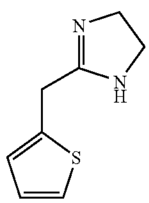 | 2-Thiophen-2-ylmethyl-4,5-dihydro-1H-imidazole |
| 145 | 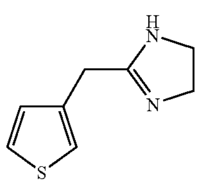 | 2-Thiophen-3-ylmethyl-4,5-dihydro-1H-imidazole |
| 146 | 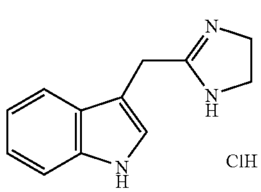 | 3-(4,5-Dihydro-1H-imidazol-2-ylmethyl)-1H-indole |
| 147 | 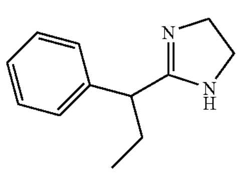 | 2-(1-Phenyl-propyl)-4,5-dihydro-1H-imidazole |

-continued

| Example No. | Structure | Name |
|---|---|---|
| 148 | 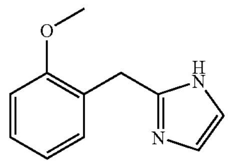 | 2-(2-Methoxy-benzyl)-1H-imidazole |
| 149 | 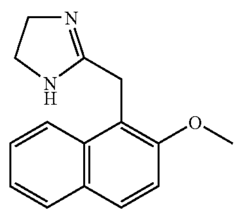 | 2-(2-Methoxy-naphthalen-1-ylmethyl)-4,5-dihydro-1H-imidazole |
| 150 | 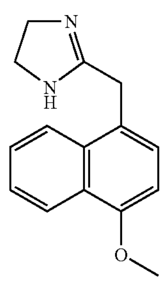 | 2-(4-Methoxy-naphthalen-1-ylmethyl)-4,5-dihydro-1H-imidazole |
| 151 | 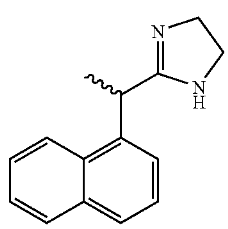 | Rac-2-(1-Naphthalen-1-yl-ethyl)-4,5-dihydro-1H-imidazole |
| 152 | 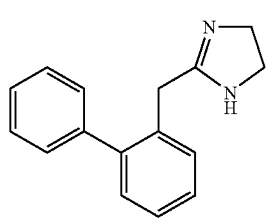 | 2-Biphenyl-2-ylmethyl-4,5-dihydro-1H-imidazole |
| 153 | 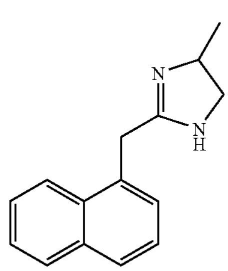 | Rac-4-Methyl-2-naphthalen-1-ylmethyl-4,5-dihydro-1H-imidazole or tautomer |

| Example No. | Structure | Name |
|---|---|---|
| 154 | 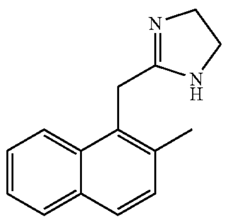 | 2-(2-Methyl-naphthalen-1-ylmethyl)-4,5-dihydro-1H-imidazole |

Example 155 rac-2-[1-(4-Phenoxy-phenyl)-ethyl]-4,5-dihydro-1H-imidazole hydrochloride rac-2-[1-(4-Phenoxy-phenyl)-ethyl]-4,5-dihydro-1H-imidazole was prepared from rac-2-(4-phenoxy-phenyl)-propionitrile in analogy to Example 17; isolated as hydrochloride: white powder; MS (EI): 267.1((M$^{+ \cdot}$).

Example 156 rac-2-[1-(4-Methoxy-2,3-dimethyl-phenyl)-ethyl]-4,5-dihydro-1H-imidazole hydrochloride rac-2-(4-Methoxy-2,3-dimethyl-phenyl)-propionitrile which was prepared from 2-(4-methoxy-2,3-dimethyl-phenyl)-acetonitrile and methyl iodide in analogy to Example 65a) was reacted with ethylenediamine to form rac-2-[1-(4-methoxy-2,3-dimethyl-phenyl)-ethyl]-4,5-dihydro-1H-imidazole in analogy to Example 19b; isolated as hydrochloride: white powder; MS (EI): 233.3 ((M$^{+ \cdot}$).

Example 157 rac-2-[1-(4-Benzyloxy-phenyl)-ethyl]-4,5-dihydro-1H-imidazole hydrochloride rac-2-[(1-(4-Benzyloxy-phenyl)-ethyl]-4,5-dihydro-1H-imidazole was prepared from rac-2-(4-benzyloxy-phenyl)-propionitrile in analogy to Example 17; isolated as hydrochloride: light yellow solid; MS (EI): 281.3((M$^{+ \cdot}$).

Example 158 rac-2-[1-(4-Benzyl-phenyl)-ethyl]-4,5-dihydro-1H-imidazole hydrochloride rac-2-[1-(4-Benzyl-phenyl)-ethyl]-4,5-dihydro-1H-imidazole was prepared from rac-2-(4-benzyl-phenyl)-propionitrile in analogy to Example 17; isolated as hydrochloride: white solid;

MS (EI): 265.1((M$^{+ \cdot}$).

Example 159 rac-2-[1-(4-Ethyl-phenyl)-ethyl]-4,5-dihydro-1H-imidazole hydrochloride a) rac-2-(4-Ethyl-phenyl)-propionitrile

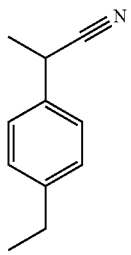

rac-2-(4-Ethyl-phenyl)-propionitrile was prepared from 1-(1-bromo-ethyl)-4-ethyl-benzene in analogy to Example 45 a). The product was directly used for the next reaction step.

b) rac-2-[1-(4-Ethyl-phenyl)-ethyl]-4,5-dihydro-1H-imidazole hydrochloride

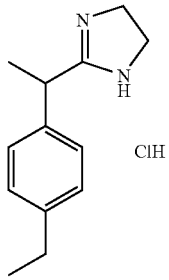

rac-2-[1-(4-Ethyl-phenyl)-ethyl]-4,5-dihydro-1H-imidazole was prepared from rac-2-(4-ethyl-phenyl)-propionitrile in analogy to Example 17; isolated as hydrochloride: beige powder;
MS (EI): 203.4 ((M$^{+\cdot}$).

Example 160 rac-2-[1-(4-Isopropyl-phenyl)-ethyl]-4,5-dihydro-1H-imidazole hydrochloride

rac-2-[1-(4-Isopropyl-phenyl)-ethyl]-4,5-dihydro-1H-imidazole was prepared from rac-2-(4-isopropyl-phenyl)-propionitrile in analogy to Example 17; isolated as hydrochloride: white powder; MS (EI): 217.3((M$^{+\cdot}$).

Example 161 rac-2-(1-Biphenyl-4-yl-ethyl)-4,5-dihydro-1H-imidazole hydrochloride

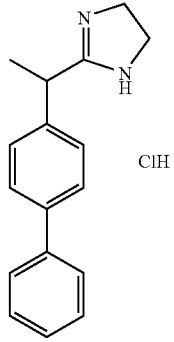

rac-2-(1-Biphenyl-4-yl-ethyl)-4,5-dihydro-1H-imidazole was prepared from rac-2-biphenyl-4-yl-propionitrile in analogy to Example 17; isolated as hydrochloride: white powder; MS (EI): 251.3 ((M$^{+\cdot}$).

Example 162 rac-2-[1-(4-Butoxy-phenyl)-ethyl]-4,5-dihydro-1H-imidazole hydrochloride

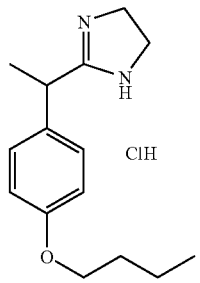

rac-2-[1-(4-Butoxy-phenyl)-ethyl]-4,5-dihydro-1H-imidazole was prepared from rac-2-(4-butoxy-phenyl)-propionitrile in analogy to Example 17; isolated as hydrochloride: light yellow solid; MS (EI): 247.4 ((M$^{+\cdot}$).

Example 163 rac-2-[1-(4-Ethoxy-phenyl)-ethyl]-4,5-dihydro-1H-imidazole hydrochloride

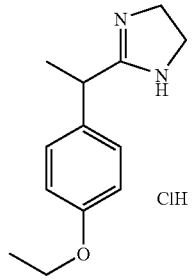

rac-2-[1-(4-Ethoxy-phenyl)-ethyl]-4,5-dihydro-1H-imidazole was prepared from rac-2-(4-ethoxy-phenyl)-propioni-

Example 164 rac-4-[1-(4,5-Dihydro-1H-imidazol-2-yl)-ethyl]-phenol hydrobromide

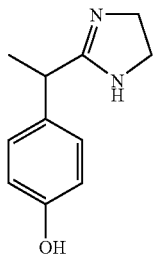

rac-4-[1-(4,5-Dihydro-1H-imidazol-2-yl)-ethyl]-phenol was prepared from rac-2-(4-hydroxy-phenyl)-propionitrile in analogy to Example 17; isolated as hydrobromide: white solid;
MS (EI): 191.4 ((M+·).

Example 165 rac-4-[1-(4,5-Dihydro-1H-imidazol-2-yl)-ethyl]-2,3-dimethyl-phenol hydrobromide

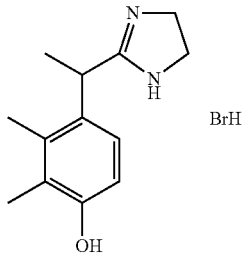

rac 4-[1-(4,5-Dihydro-1H-imidazol-2-yl)-ethyl]-2,3-dimethyl-phenol was prepared from rac-2-(4-hydroxy-2,3-dimethyl-phenyl)-propionitrile in analogy to Example 17; isolated as hydrobromide: white powder; MS (EI): 219.3 ((M+·).

Example 166

2-(6-Methyl-benzofuran-5-ylmethyl)-4,5-dihydro-1H-imidazole hydrochloride

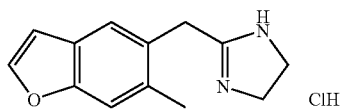

2-(6-Methyl-benzofuran-5-ylmethyl)-4,5-dihydro-1H-imidazole hydrochloride was prepared from 6-methyl-benzofuran-5-carboxylic acid methyl ester in analogy to Example 195 (steps d-f): off-white powder; MS (ISP): 215.3 ((M+H)+·).

Example 167

2-(7-Methyl-benzofuran-5-ylmethyl)-4,5-dihydro-1H-imidazole triflate

2-(7-Methyl-benzofuran-5-ylmethyl)-4,5-dihydro-1H-imidazole triflate was prepared from 7-methyl-benzofuran-5-carboxylic acid methyl ester in analogy to Example 195 (steps d-f): yellow amorphous solid; MS (ISP): 215.3 ((M+H)+·).

Example 168

2-Benzofuran-4-ylmethyl-4,5-dihydro-1H-imidazole hydrochloride

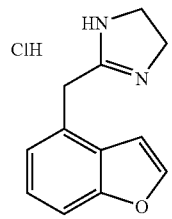

2-Benzofuran-4-ylmethyl-4,5-dihydro-1H-imidazole hydrochloride was prepared from 4-bromomethyl-benzofuran in analogy to Example 19: pale yellow solid; MS (ISP): 201.4 ((M+H)+·).

Example 169

2-(4-Methoxy-benzofuran-5-ylmethyl)-4,5-dihydro-1H-imidazole hydrochloride

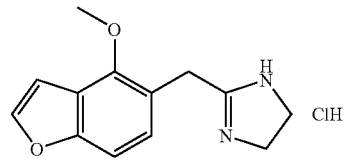

2-(4-Methoxy-benzofuran-5-ylmethyl)-4,5-dihydro-1H-imidazole hydrochloride was prepared from (4-methoxy-benzofuran-5-yl)-methanol in analogy to Example 195 (steps e and f): off-white powder; MS (ISP): 231.4 ((M+H)+·).

Example 170

2-Benzofuran-6-ylmethyl-4,5-dihydro-1H-imidazole hydrochloride

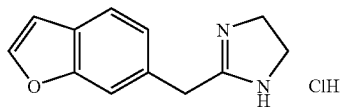

2-Benzofuran-6-ylmethyl-4,5-dihydro-1H-imidazole hydrochloride was prepared from 6-bromomethyl-benzofuran in analogy to Example 19: white powder; MS (ISP): 201.3 ((M+H)$^{+}$).

Example 171

(4,5-Dihydro-1H-imidazol-2-yl)-(4-methyl-benzofuran-5-yl)-methanol

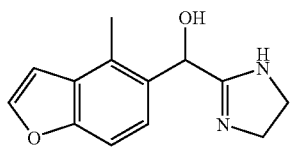

(4,5-Dihydro-1H-imidazol-2-yl)-(4-methyl-benzofuran-5-yl)-methanol was prepared from hydroxy-(4-methyl-benzofuran-5-yl)-acetic as described in Shi, Zhen; Gu, Huan Synth. Commun. 27(15), 1997, 2701-2709.: light yellow powder; MS (ISP): 231.1 ((M+H)$^{+}$).

Example 172

1-(4,5-Dihydro-1H-imidazol-2-ylmethyl)-naphthalen-2-ol hydrochloride

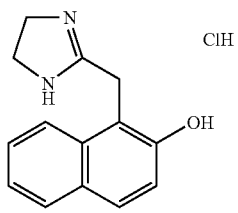

1-(4,5-Dihydro-1H-imidazol-2-ylmethyl)-naphthalen-2-ol was prepared from (2-hydroxy-naphthalen-1-yl)-acetonitrile in analogy to Example 17; isolated as hydrochloride: light yellow solid; MS (EI): 226.3 ((M$^{+}$).

Example 173

4-(4,5-Dihydro-1H-imidazol-2-ylmethyl)-2,5-dimethyl-phenol hydrobromide

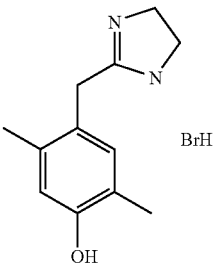

4-(4,5-Dihydro-1H-imidazol-2-ylmethyl)-2,5-dimethyl-phenol was prepared from (4-hydroxy-2,5-dimethyl-phenyl)-acetonitrile in analogy to Example 17; isolated as hydrobromide: white solid; MS (EI): 204.1 ((M$^{+}$).

Example 174

4-(4,5-Dihydro-1H-imidazol-2-ylmethyl)-2,3-dimethyl-phenol hydrobromide

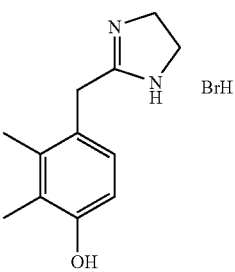

4-(4,5-Dihydro-1H-imidazol-2-ylmethyl)-2,3-dimethyl-phenol was prepared from (4-hydroxy-2,3-dimethyl-phenyl)-acetonitrile in analogy to Example 17; isolated as hydrobromide: light yellow solid; MS (EI): 205.3((M$^{+}$).

Example 175

2-(1-Bromo-naphthalen-2-ylmethyl)-4,5-dihydro-1H-imidazole

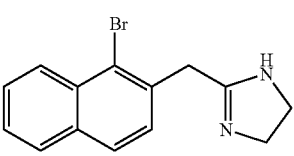

2-(1-Bromo-naphthalen-2-ylmethyl)-4,5-dihydro-1H-imidazole was prepared from (1-bromo-naphthalen-2-yl)-acetonitrile in analogy to Example 17: light yellow solid; MS (ISP): 291.2 and 289.1 ((M+H)$^{+}$).

Example 176 rac-2-(2-Methyl-1-phenyl-propyl)-1H-imidazole

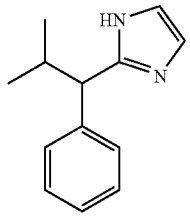

rac-2-(2-Methyl-1-phenyl-propyl)-1H-imidazole was prepared from rac-3-methyl-2-phenyl-butyronitrile in analogy to Example 17: colourless solid; MS (EI): 200.1 ((M$^{+\cdot}$).

Example 177 rac-2-[1-(2,3-Dimethyl-phenyl)-ethyl]-1H-imidazole

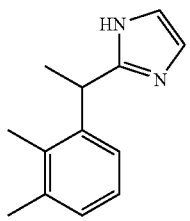

rac-2-[1-(2,3-Dimethyl-phenyl)-ethyl]-1H-imidazole was prepared from 2-[1-(2,3-dimethyl-phenyl)-ethyl]-4,5-dihydro-1H-imidazole (Example 18) in analogy to Example 70 a): light yellow solid; MS (EI): 228.9 ((M$^{+\cdot}$), 100%), 199.2 ((M-H)$^{+\cdot}$), 185.2 ((M-CH$_3$)$^{+\cdot}$).

Example 178

2-(2,3-Dichloro-benzyl)-1H-imidazole

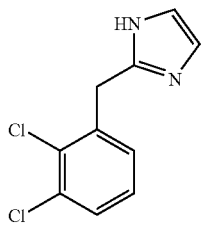

2-(2,3-Dichloro-benzyl)-1H-imidazole was prepared from 2-(2,3-dichloro-benzyl)-4,5-dihydro-1H-imidazole in analogy to Example 70 a): light brown solid; MS (ISP): 228.9 and 227.0 (((M+H)$^{+\cdot}$), 100%), 453.0 and 455.1 ((2M+H)$^{+\cdot}$).

Example 179

2-Benzofuran-7-ylmethyl-1H-imidazole

a) 2-Benzofuran-7-ylmethyl-4,5-dihydro-1-imidazole

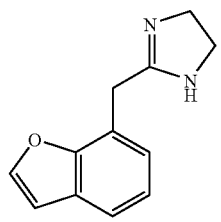

2-Benzofuran-7-ylmethyl-4,5-dihydro-1-imidazole was prepared from 7-bromomethyl-benzofuran in analogy to Example 19: yellow solid; MS (ISP): 201.3 ((M+H)$^{+\cdot}$).

b) 2-Benzofuran-7-ylmethyl-1H-imidazole

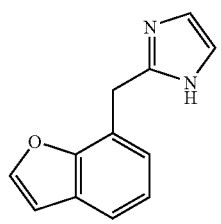

2-Benzofuran-7-ylmethyl-1H-imidazole was prepared from 2-benzofuran-7-ylmethyl-4,5-dihydro-1-imidazole in analogy to Example 70 a): light yellow solid; MS (ISP): 199.1 ((M+H)$^{+\cdot}$).

Example 180 rac-2-[1-(3-Methoxy-phenyl)-ethyl]-4,5-dihydro-1H-imidazole

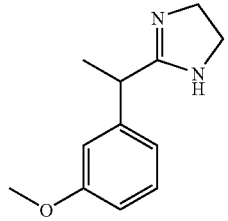

rac-2-[1-(3-Methoxy-phenyl)-ethyl]-4,5-dihydro-1H-imidazole was prepared from rac-2-(3-methoxyphenyl)-propionitrile and ethylene diamine in analogy to Example 19 b): yellow oil; MS (ISP): 205.3 ((M+H)$^{+\cdot}$).

Example 181 rac-2-[1-(3-Methoxy-phenyl)-ethyl]-1H-imidazole

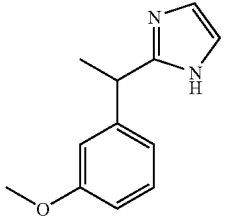

rac-2-[1-(3-Methoxy-phenyl)-ethyl]-1H-imidazole was prepared from rac-2-[1-(3-methoxy-phenyl)-ethyl]-4,5-dihydro-1H-imidazole in analogy to Example 70 a): yellow gum; MS (ISP): 203.4 ((M+H)$^{+\cdot}$).

Example 182 rac-2-[1-(2-Methoxy-phenyl)-ethyl]-4,5-dihydro-1H-imidazole

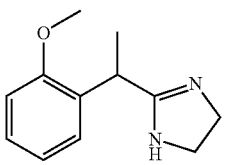

rac-2-[1-(2-Methoxy-phenyl)-ethyl]-4,5-dihydro-1H-imidazole was prepared from rac-2-(2-methoxyphenyl)-propionitrile and ethylene diamine in analogy to Example 19 b): light yellow solid; MS (ISP): 205.1 ((M+H)$^{+\cdot}$).

Example 183 rac-2-[1-(2-Methoxy-phenyl)-ethyl]-1H-imidazole

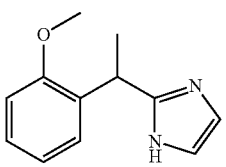

rac-2-[1-(2-Methoxy-phenyl)-ethyl]-1H-imidazole was prepared from rac-2-[1-(2-methoxy-phenyl)-ethyl]-4,5-dihydro-1H-imidazole in analogy to Example 70 a): light yellow solid; MS (EI): 171.2 (M$^+$-OCH3); 203.3 ((MH)$^{+\cdot}$).

Example 184

2-(2-Methyl-naphthalen-1-ylmethyl)-1H-imidazole

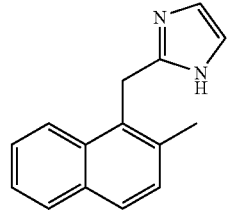

2-(2-Methyl-naphthalen-1-ylmethyl)-1H-imidazole was prepared from 2-(2-methyl-naphthalen-1-ylmethyl)-4,5-dihydro-1H-imidazole (Example 154) in analogy to Example 70 a): off-white solid; MS (ISP): 223.3 ((M+H)$^{+\cdot}$).

Example 185

2-(2,6-Dichloro-benzyl)-1H-imidazole

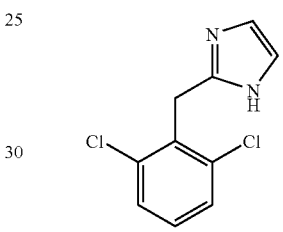

a) 1,3-Dichloro-2-(2,2-dibromo-vinyl)-benzene

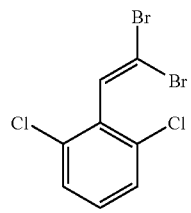

1,3-Dichloro-2-(2,2-dibromo-vinyl)-benzene was prepared from 2,6-dichlorobenzaldehyde in analogy to Example 1d): Colourless oil. MS (EI): 335.8 (4%), 333.8 (21%), 331.7 (80%), 329.8 (70%) & 327.9 (29%) (each M$^{+\cdot}$), 255.0 (10%), 252.9 (43%), 250.9 (98%) & 248.9 (60%) (each [M-Br]$^+$), 174.1 (11%), 172.0 (57%) & 170.0 (100%) (each [M-2Br]$^+$).

b) 2-(2,6-Dichloro-benzyl)-4,5-dihydro-1H-imidazole

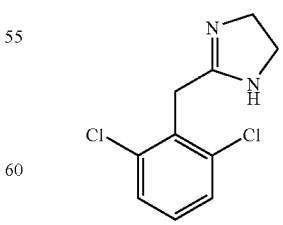

2-(2,6-Dichloro-benzyl)-4,5-dihydro-1H-imidazole was prepared from 1,3-dichloro-2-(2,2-dibromo-vinyl)-benzene and ethylene diamine in analogy to Example 1e): white crystals; MS (ISP): 233.1 (11%), 231.1 (63%) & 229.2 100%) (each [M+H]$^+$).

c) 2-(2,6-Dichloro-benzyl)-1H-imidazole

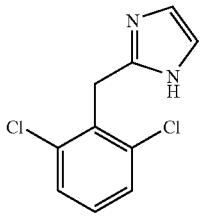

2-(2,6-Dichloro-benzyl)-1H-imidazole was prepared from 2-(2,6-dichloro-benzyl)-4,5-dihydro-1H-imidazole in analogy to Example 70 a): white crystals; MS (ISP): 231.2 (11%), 229.3 (80%) & 227.3 100%) (each [M+H]$^+$).

Example 186

2-(2,6-Dicyclopropyl-benzyl)-4,5-dihydro-1H-imidazole

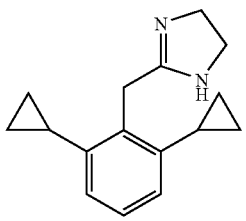

a) Butyl-[1-(2,6-difluoro-phenyl)-meth-(E)-ylidene]-amine

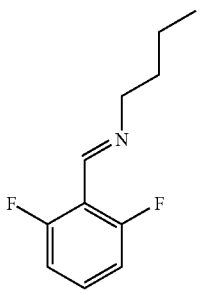

A mixture of 25.4 g (179 mmol) 2,6-difluorobenzaldehyde, 19.5 ml (197 mmol) N-butylamine and 0.68 g (3.57 mmol) p-toluenesulfonic acid in 120 ml toluene was heated in a Dean-Stark apparatus at reflux for 3 hours. After cooling to room temperature, the reaction mixture was diluted with ethyl acetate and washed sequentially with water (twice) and with saturated brine. The organic phase was dried over Na$_2$SO$_4$, filtered, and concentrated in vacuo to afford the title compound 30.4 g (86%) as a brown oil which was used in the next step without further purification. MS (ISP): 198.3 ([M+H]$^+$, 100%).

b) 2,6-Dicyclopropyl-benzaldehyde

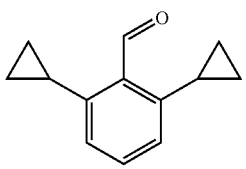

This compound was prepared using methodology described in *Synthesis* 1999, 2138-2144. A solution of cyclopropylmagnesium bromide was first prepared by dropwise addition of a solution of 4.06 ml (50.7 mmol) cyclopropyl bromide in 20 ml diethyl ether to 1.23 g (50.7 mmol) magnesium turnings followed by heating at reflux for 5 min. Meanwhile, to a solution of 2.50 g (12.7 mmol) butyl-[1-(2,6-difluoro-phenyl)-meth-(E)-ylidene]-amine in 15 ml ether at 0° C. was added 0.16 g (1.27 mmol) manganese(II) chloride. The freshly prepared solution of cyclopropylmagnesium bromide in diethyl ether was then added dropwise while the temperature of the reaction mixture was maintained at 5-10° C. After the addition was complete, the reaction mixture was stirred for 30 minutes at room temperature and then for 90 minutes at reflux. The reaction mixture was then cooled to room temperature and quenched by dropwise addition of water before being diluted with ethyl acetate. The mixture was then washed with saturated brine. The phases were separated and the organic phase was dried over Na$_2$SO$_4$, filtered and concentrated in vacuo. The residue was purified by flash chromatography (silica gel, toluene/heptane gradient) to afford 1.51 g (64%) of the title compound as a yellow oil. MS (EI): 158.1 ([M-CO]$^+$, 100%).157.1 ([M-CHO]$^{+\cdot}$, 25%), 129.2 ([M-CHO—C$_2$H$_4$]$^{+\cdot}$, 90%), 115.1 ([M-CHO—C$_3$H$_6$]$^{+\cdot}$, 43%).

c) 1,3-Dicyclopropyl-2-(2,2-dibromo-vinyl)-benzene

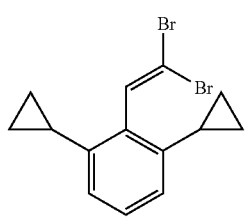

1,3-Dicyclopropyl-2-(2,2-dibromo-vinyl)-benzene was prepared from 2,6-dicyclopropyl-benzaldehyde, carbon tetrabromide and triphenylphosphine in analogy to Example 1d): colourless oil; MS (EI): 343.9 (14%), 342.0 (24%) and 340.0 (14%) (M$^+$), 182.2 ([M-2Br]$^+$, 66%), 167.2 ([M-2Br—CH$_3$)$^+$, 100%).

d) 2-(2,6-Dicyclopropyl-benzyl)-4,5-dihydro-1H-imidazole

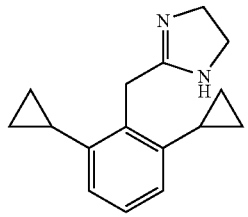

2-(2,6-Dicyclopropyl-benzyl)-4,5-dihydro-1H-imidazole was prepared from 1,3-dicyclopropyl-2-(2,2-dibromo-vinyl)-benzene and ethylenediamine in analogy to Example 1e): light yellow crystals; MS (ISP): 241.4 ([M+H]$^+$, 100%).

Example 187

2-(2-Chloro-6-iodo-benzyl)-4,5-dihydro-1H-imidazole

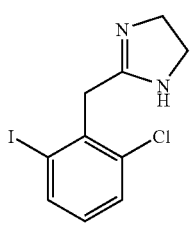

a) (2-Chloro-6-iodo-phenyl)-methanol

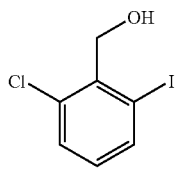

To a solution of 47.5 g (168 mmol) 2-chloro-6-iodo-benzoic acid in 300 ml tetrahydrofuran was added dropwise 420 ml (420 mmol) borane-tetrahydrofuran complex (1 M solution in tetrahydrofuran) over 30 min and then the reaction mixture was heated at 45° C. for 16 hours. 40 ml Methanol was added dropwise and then 70 ml of 25% aqueous hydrochloric acid was added dropwise, and the reaction mixture was heated at reflux for 2 hours. After cooling to room temperature the mixture was diluted with ethyl acetate and washed sequentially with water, saturated brine, 2 N aqueous sodium hydroxide solution, water and saturated brine. The organic phases was separated and dried over $Na_2SO_4$, filtered and concentrated in vacuo to afford a brown oil. The residue was taken up in 300 ml diethyl ether and the mixture was stirred for 10 min at 0° C. before being filtered. The filtrate was concentrated in vacuo and the residue was purified by chromatography (silica gel, ethyl acetate/heptane 1:3) to afford 8.17 g (18%) of the title compound as an orange crystalline solid. MS (EI): 270.0 (30%) & 268.0 (100%) ($M^+$).

b) 2-Chloro-6-iodo-benzaldehyde

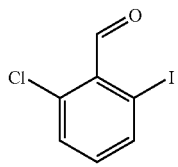

To a solution of 3.11 ml (36.2 mmol) oxalyl chloride in 40 ml dichloromethane at −78° C. was added dropwise over 20 min a solution of 5.14 ml (72.4 mmol) dimethylsulfoxide in 15 ml dichloromethane. The mixture was stirred for a further 15 min at −78° C. and then a solution of 8.10 g (3.02 mmol) (2-chloro-6-iodo-phenyl)-methanol in 40 ml dichloromethane was added dropwise over 30 min and stirring continued at −78° C. for a further 45 min. 20.9 ml (151 mmol) triethylamine were then added dropwise and the reaction mixture allowed to warm to room temperature. Water was then added and the phases were then separated. The organic phase was dried over $Na_2SO_4$, filtered and concentrated in vacuo to afford 8.35 g (100%) of the title compound as a yellow crystalline solid which was used in the next step without further purification. MS (EI): 268.0 (44%) & 266.0 (100%) ($M^+$).

c) 1-Chloro-2-(2,2-dibromo-vinyl)-3-iodo-benzene

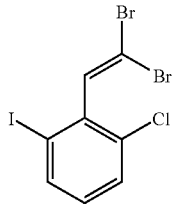

Chloro-2-(2,2-dibromo-vinyl)-3-iodo-benzene was prepared from 2-chloro-6-iodo-benzaldehyde, carbon tetrabromide and triphenylphosphine in analogy to Example 1d): colourless oil; MS (EI): 425.8 (5%), 423.8 (20%), 421.7 (46%) and 419.7 (18%) ($M^+$), 344.9 (30%), 342.8 (100%) and 340.8 (90%) ($[M-Br]^+$), 263.9 (5%) and 261.9 (25%) ($[M-2Br]^+$), 218.0 (9%), 216.0 (50%) and 214.0 (35%) ($[M-Br])^+$).

d) 2-(2-Chloro-6-iodo-benzyl)-4,5-dihydro-1H-imidazole

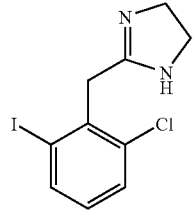

2-(2-Chloro-6-iodo-benzyl)-4,5-dihydro-1H-imidazole was prepared from 1-chloro-2-(2,2-dibromo-vinyl)-3-iodo-benzene and ethylenediamine in analogy to Example 1e): light yellow crystals; MS (ISP): 323.1 ($[M+H]^+$, 35%), 321.4 ($[M+H]^+$, 100%).

Example 188

2,4-Dichloro-3-(4,5-dihydro-1H-imidazol-2-ylmethyl)-pyridine

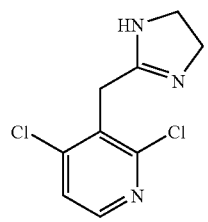

a) (2,4-Dichloro-pyridin-3-yl)-methanol

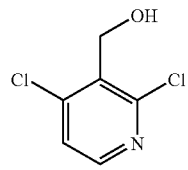

(2,4-Dichloro-pyridin-3-yl)-methanol was prepared from 2,4-dichloro-pyridine-3-carbaldehyde in analogy to Example 23 a): colourless crystals; MS (ISP): 180.0 and 178.0 ((($M+H)^+$·), 100%).

b) 3-Bromomethyl-2,4-dichloro-pyridine hydrobromide

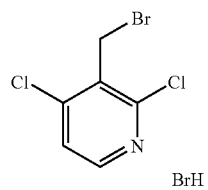

3-Bromomethyl-2,4-dichloro-pyridine was prepared from (2,4-dichloro-pyridin-3-yl)-methanol in analogy to Example 23 b) and isolated as hydrobromide: colourless crystals; NMR ($D_6$-DMSO, ppm): 4.78 (2H, s), 7.70 (2H, d), 8.37 (2H, d), 11.42 (1H, sbr).

c) (2,4-Dichloro-pyridin-3-yl)-acetonitrile

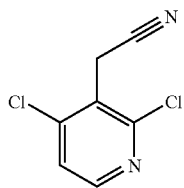

(2,4-Dichloro-pyridin-3-yl)-acetonitrile was prepared 3-bromomethyl-2,4-dichloro-pyridine in analogy to Example 45 a): colourless solid; MS (EI): 188.1 and 186.1 (M+·), 150.1 ((M-HCl)+·, 100%).

d) 2,4-Dichloro-3-(4,5-dihydro-1H-imidazol-2-ylmethyl)-pyridine

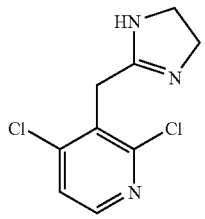

2,4-Dichloro-3-(4,5-dihydro-1H-imidazol-2-ylmethyl)-pyridine was prepared from (2,4-dichloro-pyridin-3-yl)-acetonitrile in analogy to Example 32 e) but for the second step heated in MeOH to reflux for 20 hours: colourless solid; MS (ISP): 231.8 and 229.8 (((M+H)+·), 100%).

Example 189

2-(2-Ethyl-6-methoxy-benzyl)-1H-imidazole

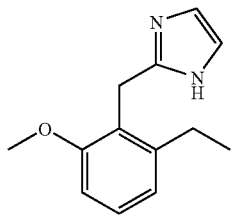

2-(2-Ethyl-6-methoxy-benzyl)-1H-imidazole was prepared from 2-(2-ethyl-6-methoxy-benzyl)-4,5-dihydro-1H-imidazole (Example 9) in analogy to Example 70a): white crystals; MS (ISP): 217.4 ([M+H]+).

Example 190

3,5-Diethyl-4-(1H-imidazol-2-ylmethyl)-1H-pyrazole

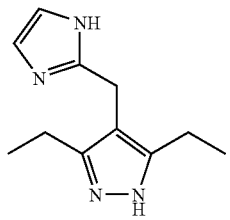

a) 4-(1-Benzyl-1H-imidazol-2-ylmethyl)-heptane-3,5-dione

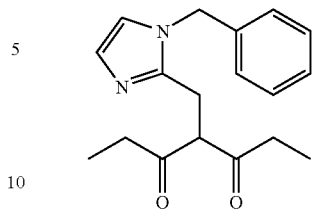

To a solution of 1.74 ml (4.7 mmol; ~21% solution in ethanol) sodium ethanolate in 18 ml dry ethanol were added 600 mg (4.7 mmol) 3,5-heptanedione and stirred at ambient temperature for 30 min. Then a solution of 1-benzyl-2-chloromethyl-1H-imidazole (prepared from 1.081 g (4.5 mmol) 1-benzyl-2-chloromethyl-1H-imidazole hydrochloride in 7 ml ethanol and 1.74 ml (5 mmol; ~21% solution in ethanol) sodium ethanolate) was added together with 30 mg potassium iodide. The mixture was heated to 50° C. for 10 min and then immediately cooled to ambient temperature and concentrated under reduced pressure at max. 30° C. Purification by flash-chromatography on silica gel with heptane/ethyl acetate 1:1 as eluent provided 423 mg 4-(1-benzyl-1H-imidazol-2-ylmethyl)-heptane-3,5-dione as light brown oil: MS (ISP): 299.2 ((M+H)+·).

b) 4-(1-Benzyl-1H-imidazol-2-ylmethyl)-3,5-diethyl-H-pyrazole

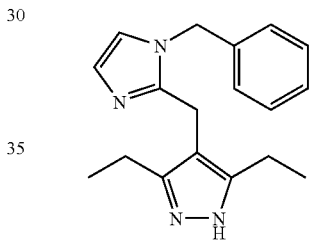

To a solution of 140 mg (0.47 mmol) 4-(1-benzyl-1H-imidazol-2-ylmethyl)-heptane-3,5-dione in 1.5 ml ethanol was added a solution of 24 mg (0.48 mmol) hydrazine monohydrate in 0.5 ml ethanol and the mixture heated to reflux for 10 min. The reaction mixture was evaporated under reduced pressure, the residue dissolved in 1N aqueous HCl solution and extracted three times with t-butyl methyl ether. The aqueous phase was adjusted to pH 12 and extracted three times with t-butyl methyl ether, the combined extracts washed with brine, dried over sodium sulfate, filtered and evaporated. Purification of the residue by flash-chromatography on silica gel with ethyl acetate as eluent provided 4-(1-benzyl-1H-imidazol-2-ylmethyl)-3,5-diethyl-1H-pyrazole as colourless viscous oil: MS (ISP): 295.3 ((M+H)+·).

c) 3,5-Diethyl-4-(1H-imidazol-2-ylmethyl)-1H-pyrazole

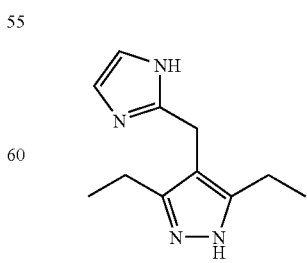

Hydrogenation of a solution of 110 mg (0.37 mmol) 4-(1-benzyl-1H-imidazol-2-ylmethyl)-3,5-diethyl-1H-pyrazole in 10 ml ethanol and 1 ml aqueous 2N HCl in presence of a catalytic mount of 10% Pd/C at 60° C. for 2 h provided after usual work-up pure 3,5-diethyl-4-(1H-imidazol-2-ylmethyl)-1H-pyrazole as colourless solid: MS (ISP): 205.0 ((M+H)$^{+\cdot}$).

Example 191

2-(2-Chloro-6-ethyl-benzyl)-1H-imidazole

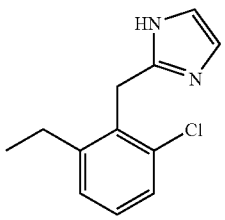

a) Butyl-[1-(2-chloro-6-fluoro-phenyl)-meth-(E)-ylidene]-amine

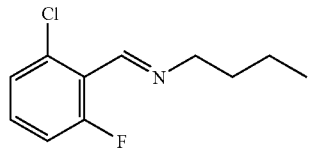

To a solution of 59.8 g (377 mmol) 2-chloro-6-fluorobenzaldehyde in 250 ml toluene were added 41.0 ml (415 mmol) N-butylamine and 1.44 g (7.54 mmol) p-toluenesulphonic acid. The mixture was heated at reflux for 5 h. After cooling to room temperature, the mixture was diluted with toluene and washed sequentially with aqueous sodium bicarbonate solution, water and saturated brine. The organic layer was dried over Na$_2$SO$_4$, filtered and concentrated in vacuo to afford 80.1 g (99% of the title compound as a dark brown oil which was used in the next step without further purification. MS (ISP): 216.2 ([M+H]$^+$), 214.2 ([M+H]$^+$).

b) Butyl-[1-(2-chloro-6-ethyl-phenyl)-meth-(E)-ylidene]-amine

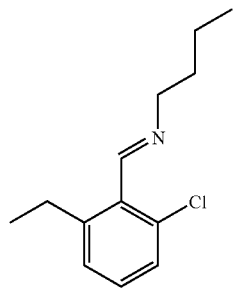

This compound was prepared using methodology described in *Synthesis* 1999, 2138-2144. To a solution of 21.2 g (99.2 mmol) butyl-[1-(2-chloro-6-fluoro-phenyl)-meth-(E)-ylidene]-amine in 150 ml tetrahydrofuran at 0° C. was added dropwise 38.0 ml (114 mmol) of a 3 M solution of ethylmagnesium bromide in ether at such a rate that the temperature of the reaction mixture was maintained below 20° C. After the addition was complete, the reaction mixture was stirred for a further 1 h at room temperature. The reaction mixture was then quenched by dropwise addition of water and diluted with ethyl acetate. The mixture was washed sequentially with water and with saturated brine, then the organic phase was dried over Na$_2$SO$_4$, filtered and concentrated in vacuo. The residue was resuspended in carbon tetrachloride and concentrated in vacuo again to afford 19.7 g (89%) of the title compound as a yellow oil which was used in the next step without further purification. MS (ISP): 226.3 ([M+H]$^+$, 30%), 224.3 ([M+H]$^+$, 100%).

c) 2-Chloro-6-ethyl-benzaldehyde

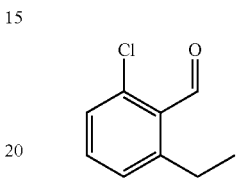

To a solution of 19.7 g (88.1 mmol) butyl-[1-(2-chloro-6-ethyl-phenyl)-meth-(E)-ylidene]-amine in 70 ml water at 0° C. was added dropwise 18.9 ml concentrated sulphuric acid. The mixture was then heated at reflux for 90 min before being cooled to room temperature and diluted with ethyl acetate. The mixture was then washed sequentially with water, saturated aqueous sodium bicarbonate solution, and saturated brine. The organic phase was dried over Na$_2$SO$_4$, filtered and concentrated in vacuo. The residue was purified by flash chromatography (silica gel, ethyl acetate/heptane 1:30) to afford 11.4 g (77%) of the title compound as a yellow oil. $^1$H-NMR (CDCl$_3$): 1.22 (3H, t, CH$_3$), 2.97 (2H, q, CH$_2$), 7.20 (1H, d, ArH), 7.30 (1H, d, ArH), 7.39 (1H, dd, ArH), 10.65 (1H, s, CHO).

d) Rac-(2-Chloro-6-ethyl-phenyl)-(1H-imidazol-2-yl)-methanol

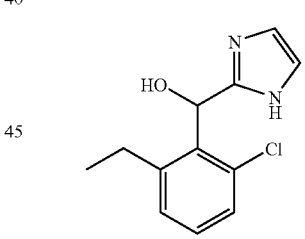

To a solution of 1.60 ml (9.79 mmol) 1-(diethoxymethyl)imidazole in 6 ml tetrahydrofuran at −78° C. was added dropwise 6.67 ml (10.7 mmol) of a 1.6 M solution of n-butyllithium in hexane. The resulting solution of 2-(1-diethoxymethyl-1H-imidazol-2-yl)-lithium was stirred at −78° C., and then added dropwise to a solution of 1.50 g (8.90 mmol) 2-chloro-6-ethyl-benzaldehyde in 6 ml tetrahydrofuran at 0° C. The reaction mixture was then stirred at 0° C. for 30 min and at room temperature for 1 h, before being quenched by dropwise addition of 1 M aqueous hydrochloric acid. The mixture was made basic by addition of aqueous sodium bicarbonbate solution and diluted with ethyl acetate. The phases were separated and the organic phase was washed with saturated brine, dried over Na$_2$SO$_4$, filtered and concentrated in vacuo to afford 2.02 g (96%) of the title compound as a yellow oil which was used in the next step without further purification.

e) 2-(2-Chloro-6-ethyl-benzyl)-1H-imidazole

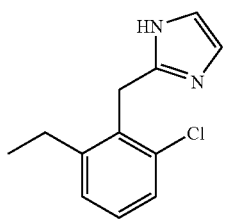

This compound was prepared using methodology described in *J. Chem. Soc., Perkin Trans.* 1, 2002, 1061-1066. To a stirred solution of 2.10 g (8.87 mmol) rac-(2-chloro-6-ethyl-phenyl)-(1H-imidazol-2-yl)-methanol in 10 ml 1,2-dichloroethane in a pressure tube were added dropwise 14.1 ml (88.7 mmol) triethylsilane and 8.04 ml (106 mmol) trifluoroacetic acid. The tube was sealed and the reaction mixture was stirred at 100° C. for 16 hours, before being cooled to room temperature and diluted with dichloromethane. The mixture was washed sequentially with 2 N aqueous sodium hydroxide solution and water and then the organic phase was dried over $Na_2SO_4$, filtered and concentrated in vacuo. The residue was purified by flash chromatography (silica gel, ethyl acetate/heptane gradient) followed by trituration in ether to afford 0.66 g (34%) of the title compound as a white crystalline solid. MS (ISP): 223.1 ([M+H]$^+$), 221.2 ([M+H]$^+$).

Example 192

3,5-Diethyl-4-(1H-imidazol-2-ylmethyl)-1-methyl-1H-pyrazole

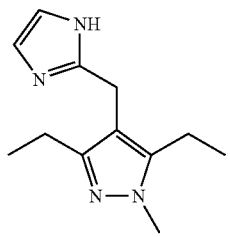

a) 4-(1-Benzyl-1H-imidazol-2-ylmethyl)-3,5-diethyl-1-methyl-1H-pyrazole

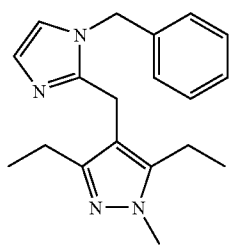

4-(1-Benzyl-1H-imidazol-2-ylmethyl)-3,5-diethyl-1-methyl-1H-pyrazole was prepared from 4-(1-benzyl-1H-imidazol-2-ylmethyl)-heptane-3,5-dione and methylhydrazine in analogy to Example 190 b): light yellow viscous oil; MS (ISP): 309.2 ((M+H)$^+$).

b) 3,5-Diethyl-4-(1H-imidazol-2-ylmethyl)-1-methyl-1H-pyrazole

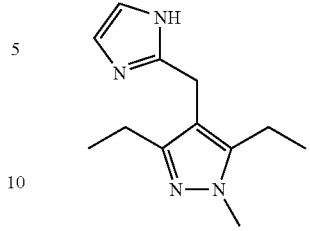

3,5-Diethyl-4-(1H-imidazol-2-ylmethyl)-1-methyl-1H-pyrazole was prepared from 4-(1-benzyl-1H-imidazol-2-yl-methyl)-3,5-diethyl-1-methyl-1H-pyrazole in analogy to Example 190 c): colourless solid; MS (ISP): 219.1 ([M+H]$^+$).

Example 193

2-(2-Ethyl-6-methyl-benzyl)-1H-imidazole

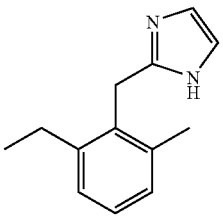

2-(2-Ethyl-6-methyl-benzyl)-1H-imidazole was prepared from 2-(2-ethyl-6-methyl-benzyl)-4,5-dihydro-1H-imidazole (Example 11) in analogy to Example 70a): white crystals; MS (ISP): 201.1 ([M+H]$^+$).

Example 194

2-(2-Cyclopropyl-6-methyl-benzyl)-1H-imidazole

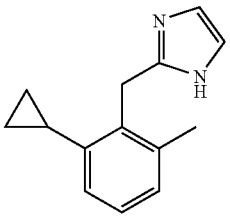

Butyl-[1-(2-chloro-6-methyl-phenyl)-meth-(E)-ylidene]-amine

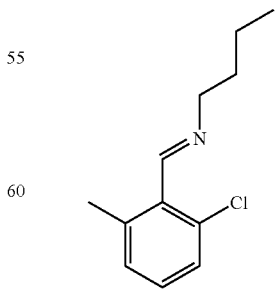

This compound was prepared using methodology described in Synthesis 1999, 2138-2144. To a solution of 7.00 g (32.8 mmol) butyl-[1-(2-chloro-6-fluoro-phenyl)-meth- (E)-ylidene]-amine in 70 ml tetrahydrofuran at 0° C. was added 0.41 g (3.28 mmol) manganese(II) chloride. 21.8 ml (65.5 mmol) of a 3 M solution of methylmagnesium chloride in tetrahydrofuran was then added dropwise while the temperature of the reaction mixture was maintained at 5-10° C. After the addition was complete, the reaction mixture was stirred for a further 30 minutes, during which time the temperature rose to 40° C. (exotherm). The reaction mixture was then quenched by dropwise addition of water and stirred for a further 30 minutes before being diluted with toluene. The mixture was then filtered and the organic phase of the filtrate was then washed with saturated brine. The phases were separated and the organic phase was dried over $Na_2SO_4$, filtered and concentrated in vacuo. The residue was resuspended in carbon tetrachloride and concentrated in vacuo again to afford 6.90 g (100%) of the title compound as a yellow oil which was used in the next step without further purification. MS (ISP): 212.1 ([M+H]$^+$), 210.1 ([M+H]$^+$).

b) 2-Cyclopropyl-6-methyl-benzaldehyde

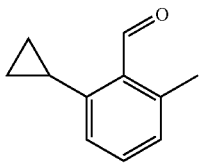

This compound was prepared using methodology described in Synthesis 1999, 2138-2144. A solution of cyclopropylmagnesium bromide was first prepared by dropwise addition of a solution of 3.06 ml (38.2 mmol) cyclopropyl bromide in 15 ml diethyl ether to 0.93 g (38.2 mmol) magnesium turnings followed by heating at reflux for 5 min. Meanwhile, to a solution of 3.20 g (15.3 mmol) butyl-[1-(2-chloro-6-methyl-phenyl)-meth-(E)-ylidene]-amine in 30 ml tetrahydrofuran at 0° C. was added 0.19 g (1.53 mmol) manganese(II) chloride. The freshly prepared solution of cyclopropylmagnesium bromide in diethyl ether was then added dropwise, during which the temperature of the reaction mixture rose to 50° C. After the addition was complete, the reaction mixture was heated at 60° C. for 16 h. The reaction mixture was then cooled to room temperature and quenched by dropwise addition of water before being diluted with ethyl acetate. The mixture was then washed sequentially with water and with saturated brine. The phases were separated and the organic phase was dried over $Na_2SO_4$, filtered and concentrated in vacuo. The residue was purified by flash chromatography (silica gel, ethyl acetate/heptane gradient) to afford 1.60 g (65%) of the title compound as a yellow oil. $^1$H-NMR (CDCl$_3$): 0.75 (2H, m, CH$_2$), 1.04 (2H, m, CH$_2$), 2.39 (1H, m, CH), 2.59 (3H, s, CH$_3$), 7.07 (1H, t, ArH), 7.33 (2H, m, ArH), 10.9 (1H, s, CHO).

c) 1-Cyclopropyl-2-(2,2-dibromo-vinyl)-3-methyl-benzene

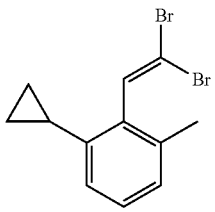

1-Cyclopropyl-2-(2,2-dibromo-vinyl)-3-methyl-benzene was prepared from 2-cyclopropyl-6-methyl-benzaldehyde, carbon tetrabromide and triphenylphosphine in analogy to Example 1d): colourless oil; $^1$H-NMR (CDCl$_3$): 0.69 (2H, m, CH$_2$), 0.94 (2H, m, CH$_2$), 1.87 (1H, m, CH), 2.26 (3H, s, CH$_3$), 6.77 (1H, d, ArH), 7.03 (1H, d, ArH), 7.17 (1H, t, ArH), 7.52 (1H, s, CH═CBr$_2$).

d) 2-(2-Cyclopropyl-6-methyl-benzyl)-4,5-dihydro-1H-imidazole

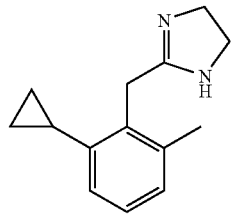

2-(2-cyclopropyl-6-methyl-benzyl)-4,5-dihydro-1H-imidazole was prepared from 1-cyclopropyl-2-(2,2-dibromo-vinyl)-3-methyl-benzene and ethylenediamine in analogy to Example 1e): yellow crystals; MS (ISP): 215.3 ([M+H]$^+$, 100%).

e) 2-(2-Cyclopropyl-6-methyl-benzyl)-1H-imidazole

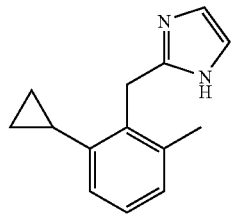

This compound was prepared using methodology described in *Synlett* 2004, 2803-2805. To a solution of 400 mg (1.87 mmol)) 2-(2-cyclopropyl-6-methyl-benzyl)-4,5-dihydro-1H-imidazole in 5 ml acetonitrile at −17° C. were added sequentially 0.50 ml (3.36 mmol) 1,8-diazabicyclo[5.4.0]undec-7-ene (DBU) and a solution of 217 mg (0.93 mmol) trichloroisocyanuric acid (TCCA) in 2 ml acetonitrile. The reaction mixture was then stirred for 2 hours at room temperature, before being diluted with ethyl acetate and washed sequentially with water and with saturated brine. The phases were separated and the organic phase was dried over $Na_2SO_4$, filtered and concentrated in vacuo. The residue was purified by flash chromatography (silica gel, ethyl acetate/heptane gradient) to afford 62 mg (16%) of the title compound as a white crystalline solid. MS (ISP): 213.4 ([M+H]$^+$, 100%).

Example 195

2-(8-Ethyl-naphthalen-1-ylmethyl)-4,5-dihydro-1H-imidazole

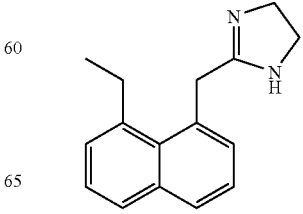

a) 8-Bromo-naphthalene-1-carboxylic acid ethyl ester

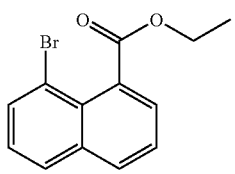

A solution of 8-bromo-naphthalene-1-carboxylic acid (1.6 g) in DMF (15 ml) was treated with potassium carbonate (2.2 g) and iodoethane (1.03 ml). The reaction mixture was stirred overnight at r.t., then quenched with water and extracted with ethyl acetate. The organics were dried over MgSO$_4$, filtered and concentrated. The crude product was purified by column chromatography (silica gel; gradient: cyclohexane→cyclohexane/EtOAc 1:1) to give 8-bromo-naphthalene-1-carboxylic acid ethyl ester (1.57 g) as colorless liquid. MS (ISP): 279.1 ((M+H)$^+$).

b) 8-Vinyl-naphthalene-1-carboxylic acid ethyl ester

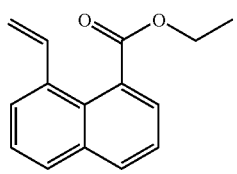

A stream of argon was passed through a solution of 8-bromo-naphthalene-1-carboxylic acid ethyl ester (1.44 g) in toluene (15 ml) for 15 min. Then tetrakis (triphenylphosphine) palladium (179 mg) and vinyltributylstannane (1.65 ml) were added. The reaction mixture was heated under an Argon atmosphere to 100° C. overnight, then cooled to r.t. and treated with 4M potassium fluoride solution. The suspension was stirred for 10 min and then filtered. The solids were washed with toluene. The filtrate was washed with 4M K solution, then dried over MgSO$_4$, filtered and concentrated. The crude product was purified by column chromatography (silica gel; gradient: cyclohexane→cyclohexane/EtOAc 3:2) to give 8-vinyl-naphthalene-1-carboxylic acid ethyl ester (1.11 g) as light yellow liquid. MS (ISP): 227.1 ((M+H)$^+$).

c) 8-Ethyl-naphthalene-1-carboxylic acid ethyl ester

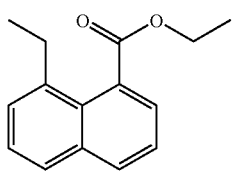

A solution of 8-vinyl-naphthalene-1-carboxylic acid ethyl ester (1.1 g) in EtOH (25 ml) was treated with acetic acid (1 ml) and Pd/C (270 mg; 10%) and hydrogenated at normal pressure overnight. The catalyst was filtered off. The filtrate was concentrated. The crude product was isolated by chromatography (silica gel; gradient: cyclohexane→cyclohexane/EtOAc 3:2) to give 8-ethyl-naphthalene-1-carboxylic acid ethyl ester (1.05 g) as colorless liquid. MS (ISP): 229.3 ((M+H)$^+$).

d) (8-Ethyl-naphthalen-1-yl)-methanol

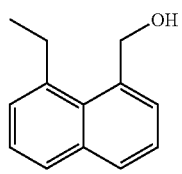

A solution of 8-ethyl-naphthalene-1-carboxylic acid ethyl ester (1.04 g) in THF (30 ml) was cooled to 0° C. and treated with diisobutyl aluminium hydride solution (11.4 ml; 1.2 M in toluene). The reaction mixture was stirred for 2 hrs at r.t., then again cooled to 0° C. and treated with H$_2$O (50 ml) and 0.1N HCl (50 ml). The mixture was extracted with EtOAc. The organics were dried over MgSO$_4$, filtered and concentrated. The crude product was purified by column chromatography (silica gel; gradient cyclohexane→cyclohexane/EtOAc 4:1) to give (8-ethyl-naphthalen-1-yl)-methanol (769 mg) as white solid. MS (ISP): 187.3 ((M+H)$^+$).

e) 1-Bromomethyl-8-ethyl-naphthalene

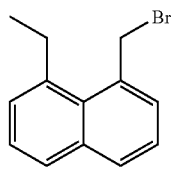

A solution of (8-ethyl-naphthalen-1-yl)-methanol (760 mg) in dichloromethane (15 ml) was cooled to 0° C. and treated with carbon tetrabromide (2.03 g). A solution of triphenylphosphine (1.28 g) in dichloromethane (15 ml) was added dropwise. The reaction mixture was stirred at r.t. overnight, then concentrated. The crude product was purified by column chromatography (silica gel; cyclohexane→cyclohexane/EtOAc 4:1) to give 1-bromomethyl-8-ethyl-naphthalene (670 mg) as light yellow liquid.

f) 2-(8-Ethyl-naphthalen-1-ylmethyl)-4,5-dihydro-1H-imidazole

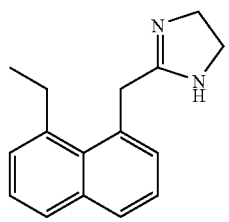

2-(8-Ethyl-naphthalen-1-ylmethyl)-4,5-dihydro-1H-imidazole was prepared from 1-bromomethyl-8-ethyl-naphthalene in analogy to Example 19: yellow solid; MS (ISP): 239.3 ((M+H)$^+$).

Example 196

2-(3-Chloro-2,6-diethyl-benzyl)-4,5-dihydro-1H-imidazole

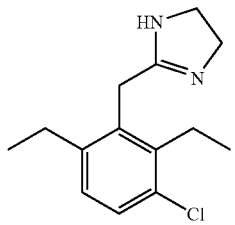

a) Butyl-[1-(2,3-dichloro-6-fluoro-phenyl)-meth-(E)-ylidene]-amine

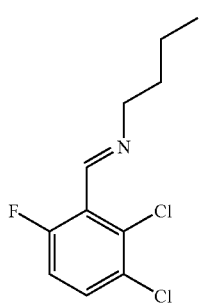

Butyl-[1-(2,3-dichloro-6-fluoro-phenyl)-meth-(E)-ylidene]-amine was prepared from 2,3-dichloro-6-fluorobenzaldehyde, N-butylamine and p-toluenesulphonic acid in analogy to Example 191a): brown oil; $^1$H-NMR (CDCl$_3$): 0.96 (3H, t, CH$_3$), 1.39 (2H, sextet, CH$_2$), 1.73 (2H, quintet, CH$_2$), 3.71 (2H, q, CH$_2$), 7.02 (1H, dd, ArH), 7.44 (1H, dd, ArH), 8.44 (1H, s, CH=N).

b) Butyl-[1-(3-chloro-2-ethyl-6-fluoro-phenyl)-meth-(E)-ylidene]-amine

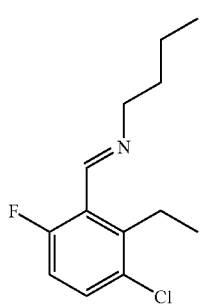

Butyl-[1-(3-chloro-2-ethyl-6-fluoro-phenyl)-meth-(E)-ylidene]-amine was prepared from butyl-[1-(2,3-dichloro-6-fluoro-phenyl)-meth-(E)-ylidene]-amine, ethylmagnesium bromide and manganese(II) chloride in analogy to Example 194a): yellow oil; $^1$H-NMR (CDCl$_3$): 0.97 (3H, t, CH$_3$), 1.15 (3H, t, CH$_3$), 1.43 (2H, sextet, CH$_2$), 1.70 (2H, quintet, CH$_2$), 3.06 (2H, q, CH$_2$), 3.66 (2H, t, CH$_2$), 6.88 (1H, dd, ArH), 7.34 (1H, dd, ArH), 8.51 (1H, s, CH=N).

c) 3-Chloro-2,6-diethyl-benzaldehyde

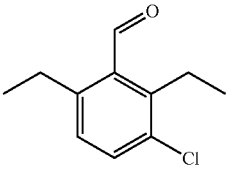

3-Chloro-2,6-diethyl-benzaldehyde was prepared from butyl-[1-(3-chloro-2-ethyl-6-fluoro-phenyl)-meth-(E)-ylidene]-amine, ethylmagnesium bromide and manganese (II) chloride in analogy to Example 194b): yellow oil; $^1$H-NMR (CDCl$_3$): 1.24 (6H, t, 2×CH$_3$), 2.89 (2H, q, CH$_2$), 3.06 (2H, q, CH$_2$), 7.07 (1H, d, ArH), 7.45 (1H, d, ArH), 10.55 (1H, s, CH=O).

d) 1-Chloro-3-(2,2-dibromo-vinyl)-2,4-diethyl-benzene

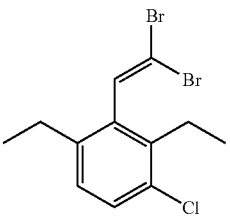

1-Chloro-3-(2,2-dibromo-vinyl)-2,4-diethyl-benzene was prepared from 3-chloro-2,6-diethyl-benzaldehyde, carbon tetrabromide and triphenylphosphine in analogy to Example 1d): colourless oil; $^1$H-NMR (CDCl$_3$): 1.14 (3H, t, CH$_3$), 1.17 (3H, t, CH$_3$), 2.56 (2H, qd, CH$_2$), 2.72 (2H, q, CH$_2$), 7.03 (1H, d, ArH), 7.29 (1H, d, ArH), 7.44 (1H, s, CH=CBr$_2$).

e) 2-(3-Chloro-2,6-diethyl-benzyl)-4,5-dihydro-1H-imidazole

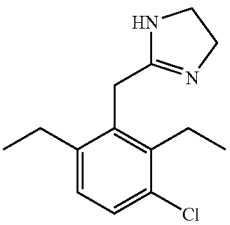

2-(3-Chloro-2,6-diethyl-benzyl)-4,5-dihydro-1H-imidazole was prepared from 1-chloro-3-(2,2-dibromo-vinyl)-2,4-diethyl-benzene and ethylenediamine in analogy to Example 1e): yellow crystals; MS (ISP): 251.3 ([M+H]$^+$, 100%).

Example 197

2-(2,6-Diethyl-3-fluoro-benzyl)-4,5-dihydro-1H-imidazole

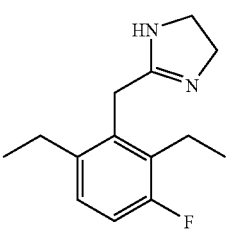

a) Butyl-[1-(2-chloro-3,6-difluoro-phenyl)-meth-(E)-ylidene]-amine

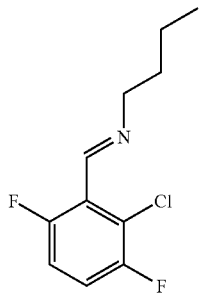

Butyl-[1-(2-chloro-3,6-difluoro-phenyl)-meth-(E)-ylidene]-amine was prepared from 2-chloro-3,6-difluorobenzaldehyde, N-butylamine and p-toluenesulphonic acid in analogy to Example 191a): yellow oil; MS (ISP): 234.1 ([M+H]$^+$, 30%), 232.3 ([M+H]$^+$, 100%).

b) Butyl-[1-(2-ethyl-3,6-difluoro-phenyl)-meth-(E)-ylidene]-amine

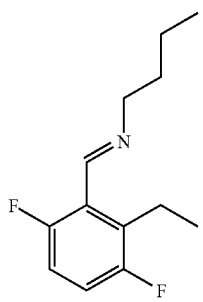

Butyl-[1-(2-ethyl-3,6-difluoro-phenyl)-meth-(E)-ylidene]-amine was prepared from butyl-[1-(2-chloro-3,6-difluoro-phenyl)-meth-(E)-ylidene]-amine, ethylmagnesium bromide and manganese(II) chloride in analogy to Example 194a): brown oil; $^1$H-NMR (CDCl$_3$): 0.97 (3H, t, CH$_3$), 1.15 (3H, t, CH$_3$), 1.43 (2H, sextet, CH$_2$), 1.70 (2H, quintet, CH$_2$), 2.98 (2H, qd, CH$_2$), 3.66 (2H, t, CH$_2$), 6.87 (1H, td, ArH), 6.99 (1H, td, ArH), 8.52 (1H, s, CH=N).

c) 2,6-Diethyl-3-fluoro-benzaldehyde

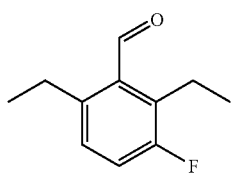

2,6-Diethyl-3-fluoro-benzaldehyde was prepared from butyl-[1-(2-ethyl-3,6-difluoro-phenyl)-meth-(E)-ylidene]-amine, ethylmagnesium bromide and manganese(II) chloride in analogy to Example 194b): yellow oil; $^1$H-NMR (CDCl$_3$): 1.22 (6H, overlapping t, 2×CH$_3$), 2.89 (4H, overlapping q, 2×CH$_2$), 7.08 (1H, dd, ArH), 7.14 (1H, dd, ArH), 10.55 (1H, s, CH=O).

d) 2-(2,2-Dibromo-vinyl)-1,3-diethyl-4-fluoro-benzene

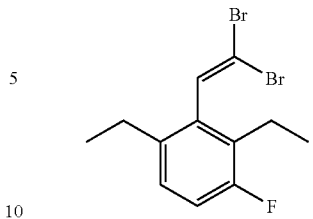

2-(2,2-Dibromo-vinyl)-1,3-diethyl-4-fluoro-benzene was prepared from 2,6-diethyl-3-fluoro-benzaldehyde, carbon tetrabromide and triphenylphosphine in analogy to Example 1d): colourless oil; $^1$H-NMR (CDCl$_3$): 1.15 (3H, t, CH$_3$), 1.18 (3H, t, CH$_3$), 2.58 (4H, m, 2×CH$_2$), 6.97 (1H, dd, ArH), 7.04 (1H, dd, ArH), 7.42 (1H, s, CH=CBr$_2$).

e) 2-(2,6-Diethyl-3-fluoro-benzyl)-4,5-dihydro-1H-imidazole

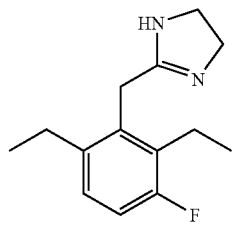

2-(2,6-Diethyl-3-fluoro-benzyl)-4,5-dihydro-1H-imidazole was prepared from 2-(2,2-dibromo-vinyl)-1,3-diethyl-4-fluoro-benzene and ethylenediamine in analogy to Example 1e): yellow crystals; MS (ISP): 235.3 ([M+H]$^+$, 100%).

Example 198

2-(3-Chloro-2-ethyl-6-fluoro-benzyl)-4,5-dihydro-H-imidazole

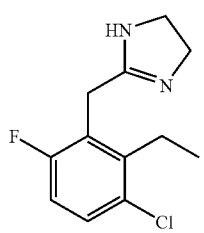

a) 3-Chloro-2-ethyl-6-fluoro-benzaldehyde

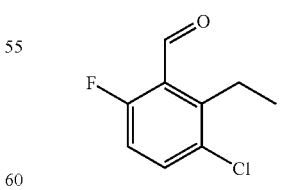

3-Chloro-2-ethyl-6-fluoro-benzaldehyde was prepared from butyl-[1-(3-chloro-2-ethyl-6-fluoro-phenyl)-meth-(E)-ylidene]-amine by flash chromatography (silica gel, ethyl acetate/heptane gradient): yellow oil; $^1$H-NMR (CDCl$_3$): 1.21 (3H, t, CH$_3$), 3.16 (2H, q, CH$_2$), 6.99 (1H, dd, ArH), 7.55 (1H, dd, ArH), 10.45 (1H, s, CH=O).

b) 1-Chloro-3-(2,2-dibromo-vinyl)-2-ethyl-4-fluoro-benzene

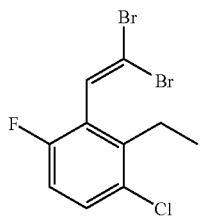

1-Chloro-3-(2,2-dibromo-vinyl)-2-ethyl-4-fluoro-benzene was prepared from 3-chloro-2-ethyl-6-fluoro-benzaldehyde, carbon tetrabromide and triphenylphosphine in analogy to Example 1d): colourless oil; $^1$H-NMR (CDCl$_3$): 1.15 (3H, t, CH$_3$), 2.72 (2H, q, CH$_2$), 6.90 (1H, dd, ArH), 7.29 (1H, s, CH=CBr$_2$), 7.33 (1H, dd, ArH).

c) 2-(3-Chloro-2-ethyl-6-fluoro-benzyl)-4,5-dihydro-1H-imidazole

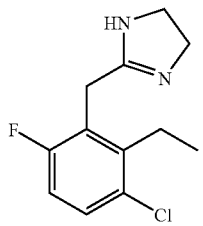

2-(3-Chloro-2-ethyl-6-fluoro-benzyl)-4,5-dihydro-1H-imidazole was prepared from 1-chloro-3-(2,2-dibromo-vinyl)-2-ethyl-4-fluoro-benzene and ethylenediamine in analogy to Example 1e): yellow crystals; MS (ISP): 243.3 ([M+H]$^+$, 30%), 241.2 ([M+H]$^+$, 100%).

Example 199

2-(2-Ethyl-3,6-difluoro-benzyl)-4,5-dihydro-1H-imidazole

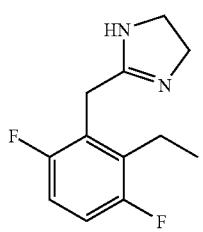

a) 2-Ethyl-3,6-difluoro-benzaldehyde

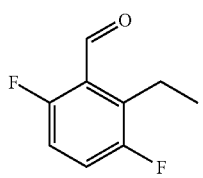

2-Ethyl-3,6-difluoro-benzaldehyde was prepared from butyl-[1-(2-ethyl-3,6-difluoro-phenyl)-meth-(E)-ylidene]-amine by flash chromatography (silica gel, ethyl acetate/heptane gradient): yellow oil; $^1$H-NMR (CDCl$_3$): 1.22 (3H, t, CH$_3$), 3.02 (2H, m, CH$_2$), 6.99 (1H, ddd, ArH), 7.23 (1H, ddd, ArH), 10.45 (1H, d, CH=O).

b) 2-(2,2-Dibromo-vinyl)-3-ethyl-1,4-difluoro-benzene

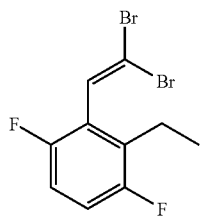

2-(2,2-Dibromo-vinyl)-3-ethyl-1,4-difluoro-benzene was prepared from 2-ethyl-3,6-difluoro-benzaldehyde, carbon tetrabromide and triphenylphosphine in analogy to Example 1d): colourless oil; $^1$H-NMR (CDCl$_3$): 1.15 (3H, t, CH$_3$), 2.60 (2H, qd, CH$_2$), 6.89 (1H, ddd, ArH), 7.00 (1H, ddd, ArH), 7.26 (1H, s, CH=CBr$_2$).

c) 2-(2-Ethyl-3,6-difluoro-benzyl)-4,5-dihydro-1H-imidazole

2-(2-Ethyl-3,6-difluoro-benzyl)-4,5-dihydro-1H-imidazole was prepared from 2-(2,2-dibromo-vinyl)-3-ethyl-1,4-difluoro-benzene and ethylenediamine in analogy to Example 1e): yellow crystals; MS (ISP): 225.3 ([M+H]$^+$, 100%).

Example 200

2-(8-Ethyl-naphthalen-1-ylmethyl)-1H-imidazole

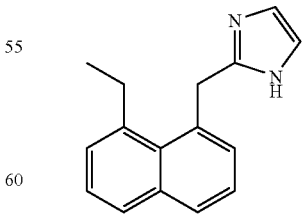

2-(8-Ethyl-naphthalen-1-ylmethyl)-1H-imidazole was prepared from 2-(8-ethyl-naphthalen-1-ylmethyl)-4,5-dihydro-1H-imidazole (Example 195) in analogy to Example 70 a): off-white solid; MS (ISP): 237.1 ((M+H)$^+$).

Example 201

2-(2,6-Diisopropyl-benzyl)-1H-imidazole

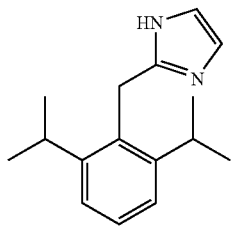

2-(2,6-Diisopropyl-benzyl)-1H-imidazole was prepared from 2-(2,6-diisopropyl-benzyl)-4,5-dihydro-1H-imidazole (Example 4), TCCA and DBU in analogy to Example 194e): yellow crystals; MS (ISP): 243.4 ([M+H]$^+$).

Example 202

2-(2,6-Diethyl-3-fluoro-benzyl)-1H-imidazole

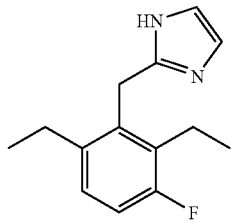

2-(2,6-Diethyl-3-fluoro-benzyl)-1H-imidazole was prepared from 2-(2,6-diethyl-3-fluoro-benzyl)-4,5-dihydro-1H-imidazole (Example 197), TCCA and DBU in analogy to Example 194e): light yellow crystals; MS (ISP): 233.3 ([M+H]$^+$).

Example 203

2-(3-Chloro-2,6-diethyl-benzyl)-1H-imidazole

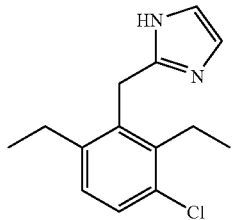

2-(3-Chloro-2,6-diethyl-benzyl)-1H-imidazole was prepared from 2-(3-chloro-2,6-diethyl-benzyl)-4,5-dihydro-1H-imidazole (Example 196), TCCA and DBU in analogy to Example 194e): light yellow crystals; MS (ISP): 251.3 ([M+H]$^+$, 39%), 249.2 ([M+H]$^+$, 100%).

Example 204

2-(3-Chloro-2-ethyl-6-fluoro-benzyl)-1H-imidazole

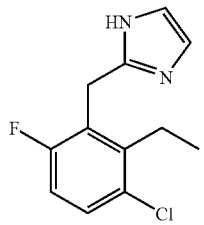

2-(3-Chloro-2-ethyl-6-fluoro-benzyl)-1H-imidazole was prepared from 2-(3-chloro-2-ethyl-6-fluoro-benzyl)-4,5-dihydro-1H-imidazole (Example 198), TCCA and DBU in analogy to Example 194e): light yellow crystals; MS (ISP): 241.2 ([M+H]$^+$, 58%), 239.2 ([M+H]$^+$, 100%).

Example 205

2-(2-Ethyl-3,6-difluoro-benzyl)-1H-imidazole

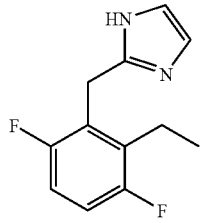

2-(2-Ethyl-3,6-difluoro-benzyl)-1H-imidazole was prepared from 2-(2-ethyl-3,6-difluoro-benzyl)-4,5-dihydro-1H-imidazole (Example 199), TCCA and DBU in analogy to Example 194e): light yellow crystals; MS (ISP): 223.3 ([M+H]$^+$, 100%).

Example 206

2-(2,6-Diethyl-3-methoxy-benzyl)-4,5-dihydro-1H-imidazole

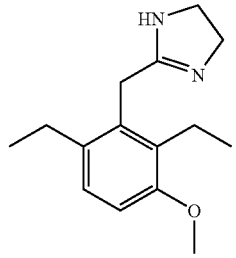

a) Butyl-[1-(2,6-difluoro-3-methoxy-phenyl)-meth-(E)-ylidene]-amine

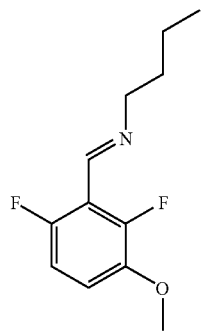

Butyl-[1-(2,6-difluoro-3-methoxy-phenyl)-meth-(E)-ylidene]-amine was prepared from 2,6-difluoro-3-methoxy-benzaldehyde, N-butylamine and p-toluenesulphonic acid in analogy to Example 186a): red oil; MS (ISP): 228.4 ([M+H]$^+$, 100%).

b) 2,6-Diethyl-3-methoxy-benzaldehyde

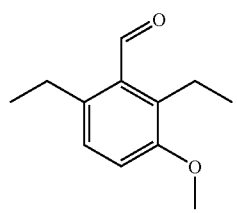

2,6-Diethyl-3-methoxy-benzaldehyde was prepared from butyl-[1-(2,6-difluoro-3-methoxy-phenyl)-meth-(E)-ylidene]-amine, ethylmagnesium bromide and manganese (II) chloride in analogy to Example 186b): yellow oil; $^1$H-NMR (CDCl$_3$): 1.18 (3H, t, CH$_3$), 1.23 (3H, t, CH$_3$), 2.87 (2H, q, CH$_2$), 2.95 (2H, q, CH$_2$), 3.84 (3H, s, OMe), 6.97 (1H, d, ArH), 7.07 (1H, d, ArH), 10.58 (1H, s, CH=O).

d) 2-(2,2-Dibromo-vinyl)-1,3-diethyl-4-methoxy-benzene

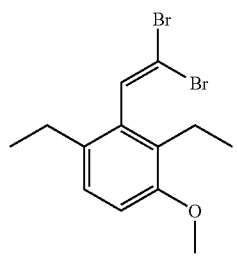

2-(2,2-Dibromo-vinyl)-1,3-diethyl-4-methoxy-benzene was prepared from 2,6-diethyl-3-methoxy-benzaldehyde, carbon tetrabromide and triphenylphosphine in analogy to Example 1d): colourless oil; $^1$H-NMR (CDCl$_3$): 1.08 (3H, t, CH$_3$), 1.17 (3H, t, CH$_3$), 2.55 (4H, m, 2×CH$_2$), 3.81 (3H, s, OMe), 6.82 (1H, d, ArH), 7.05 (1H, d, ArH), 7.44 (1H, s, CH=CBr$_2$).

e) 2-(2,6-Diethyl-3-methoxy-benzyl)-4,5-dihydro-1H-imidazole

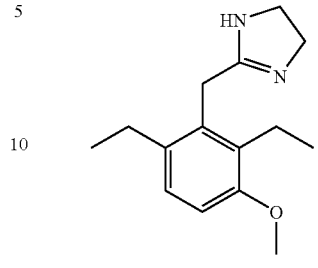

2-(2,6-Diethyl-3-methoxy-benzyl)-4,5-dihydro-1H-imidazole was prepared from 2-(2,2-dibromo-vinyl)-1,3-diethyl-4-methoxy-benzene and ethylenediamine in analogy to Example 1e): yellow crystals; MS (ISP): 247.4 ([M+H]$^+$, 100%).

Example 207

2-(2,6-Diethyl-3-methoxy-benzyl)-1H-imidazole

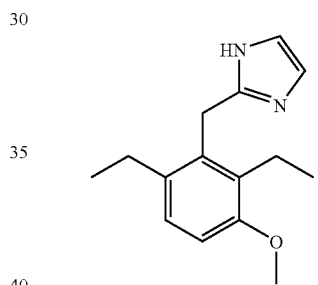

2-(2,6-Diethyl-3-methoxy-benzyl)-1H-imidazole was prepared from 2-(2,6-diethyl-3-methoxy-benzyl)-4,5-dihydro-1H-imidazole (Example 206), TCCA and DBU in analogy to Example 194e): light yellow crystals; MS (ISP): 245.4 ([M+H]$^+$, 100%).

Example 208

3,5-Diethyl-4-(1H-imidazol-2-ylmethyl)-1-methyl-1H-pyrazole

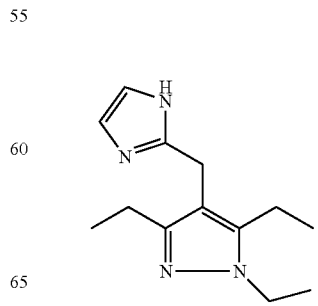

a) 4-(1-Benzyl-1H-imidazol-2-ylmethyl)-1,3,5-triethyl-1H-pyrazole

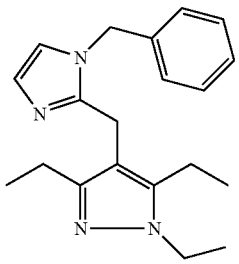

4-(1-Benzyl-1H-imidazol-2-ylmethyl)-1,3,5-triethyl-1H-pyrazole was prepared from 4-(1-benzyl-1H-imidazol-2-yl-methyl)-heptane-3,5-dione and ethylhydrazine in analogy to Example 190 b): light yellow viscous oil; MS (ISP): 323.2 ((M+H)$^{+\cdot}$).

b) 1,3,5-Triethyl-4-(1H-imidazol-2-ylmethyl)-1H-pyrazole

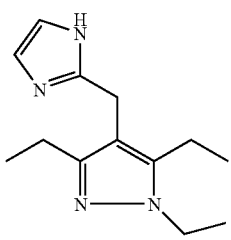

1,3,5-Triethyl-4-(1H-imidazol-2-ylmethyl)-1H-pyrazole was prepared from 4-(1-benzyl-1H-imidazol-2-ylmethyl)-1,3,5-triethyl-1H-pyrazole by debenzylation with sodium in liquid ammonia for 10 min. The blue reaction mixture was quenched by addition of solid ammonium chloride, the ammonia evaporated and the residue distributed between water and t-butyl methyl ether. The organic phase was washed with brine, dried over sodium sulfate, filtered and evaporated. 1,3,5-Triethyl-4-(1H-imidazol-2-ylmethyl)-1H-pyrazole was obtained as light yellow viscous oil; MS (ISP): 233.0 ((M+H)$^{+\cdot}$).

Example 209

Rac-(2,6-Diethyl-4-methoxy-phenyl)-(1H-imidazol-2-yl)-methanol

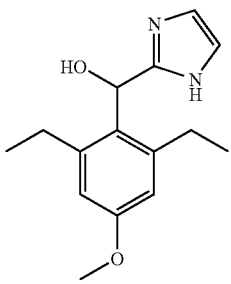

a) Butyl-[1-(2,6-difluoro-4-methoxy-phenyl)-meth-(E)-ylidene]-amine

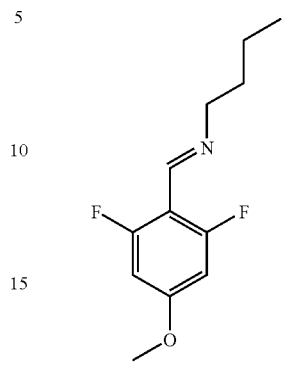

Butyl-[1-(2,6-difluoro-4-methoxy-phenyl)-meth-(E)-ylidene]-amine was prepared from 2,6-difluoro-4-methoxy-benzaldehyde, N-butylamine and p-toluenesulphonic acid in analogy to Example 186a): yellow oil; MS (ISP): 228.4 ([M+H]$^+$, 100%).

b) 2,6-Diethyl-4-methoxy-benzaldehyde

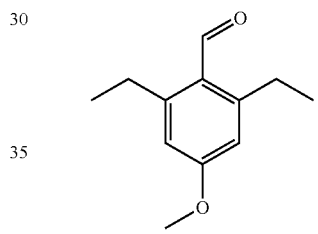

2,6-Diethyl-4-methoxy-benzaldehyde was prepared from butyl-[1-(2,6-difluoro-4-methoxy-phenyl)-meth-(E)-ylidene]-amine, ethylmagnesium bromide and manganese (II) chloride in analogy to Example 186b): yellow oil; MS (ISP): 193.3 ([M+H]$^+$, 100%).

c) Rac-(2,6-Diethyl-4-methoxy-phenyl)-(1H-imidazol-2-yl)-methanol

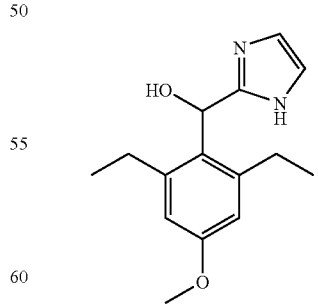

rac-(2,6-Diethyl-4-methoxy-phenyl)-(1H-imidazol-2-yl)-methanol was prepared from 2,6-diethyl-4-methoxy-benzaldehyde and 2-(1-diethoxymethyl-1H-imidazol-2-yl)-lithium in analogy to Example 191d): yellow crystals; $^1$H-NMR (CDCl₃): 1.11 (3H, t, CH₃), 2.55 (2H, qd, CH₂), 2.62 (2H, qd, CH₂), 3.83 (3H, s, OMe), 6.23 (1H, s, CH), 6.64 (2H, s, ArH), 6.98 (2H, s, imidazole-H).

Example 210

2-(2,6-Diethyl-4-methoxy-benzyl)-1H-imidazole

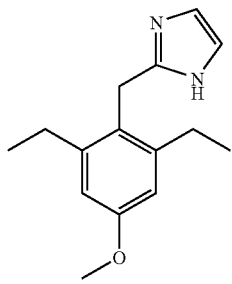

2-(2,6-Diethyl-4-methoxy-benzyl)-1H-imidazole was prepared from rac-(2,6-diethyl-4-methoxy-phenyl)-(1H-imidazol-2-yl)-methanol, triethylsilane and trifluoroacetic acid in analogy to Example 191e): white crystals; MS (ISP): 245.4 ([M+H]⁺, 100%).

Example 211

3,5-Diethyl-4-(1H-imidazol-2-ylmethyl)-1-propyl-1H-pyrazole

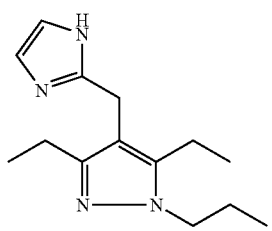

a) 4-(1-Benzyl-1H-imidazol-2-ylmethyl)-3,5-diethyl-1-propyl-1H-pyrazole

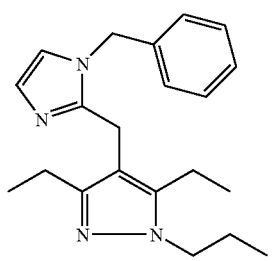

4-(1-Benzyl-1H-imidazol-2-ylmethyl)-3,5-diethyl-1-propyl-1H-pyrazole was prepared from 4-(1-benzyl-1H-imidazol-2-ylmethyl)-heptane-3,5-dione and propylhydrazine in analogy to Example 190 b): light yellow viscous oil; MS (EI): 336.2 ((M⁺·), 100%), 245.3 ((M-PhCH₂)⁺·).

b) 3,5-Diethyl-4-(1H-imidazol-2-ylmethyl)-1-propyl-1H-pyrazole

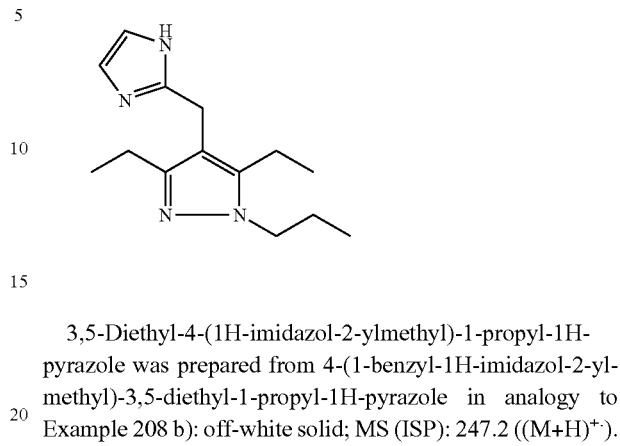

3,5-Diethyl-4-(1H-imidazol-2-ylmethyl)-1-propyl-1H-pyrazole was prepared from 4-(1-benzyl-1H-imidazol-2-ylmethyl)-3,5-diethyl-1-propyl-1H-pyrazole in analogy to Example 208 b): off-white solid; MS (ISP): 247.2 ((M+H)⁺·).

Example 212

3,5-Diethyl-4-(1H-imidazol-2-ylmethyl)-1-isopropyl-1H-pyrazole

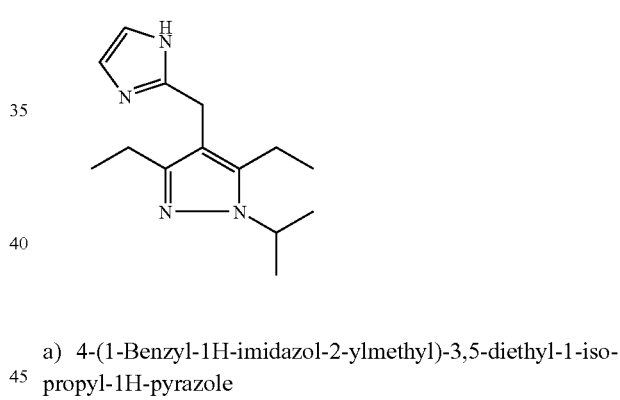

a) 4-(1-Benzyl-1H-imidazol-2-ylmethyl)-3,5-diethyl-1-isopropyl-1H-pyrazole

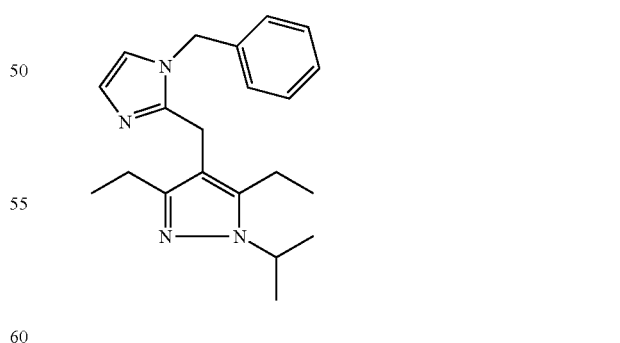

4-(1-Benzyl-1H-imidazol-2-ylmethyl)-3,5-diethyl-1-isopropyl-1H-pyrazole was prepared from 4-(1-benzyl-1H-imidazol-2-ylmethyl)-heptane-3,5-dione and isopropylhydrazine in analogy to Example 190 b): light yellow viscous oil; MS (ISP): 337.3 ((M+H)⁺·).

b) 3,5-Diethyl-4-(1H-imidazol-2-ylmethyl)-1-isopropyl-1H-pyrazole

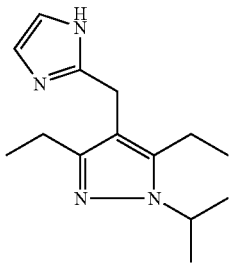

3,5-Diethyl-4-(1H-imidazol-2-ylmethyl)-1-isopropyl-1H-pyrazole was prepared from 4-(1-benzyl-1H-imidazol-2-ylmethyl)-3,5-diethyl-1-isopropyl-1H-pyrazole in analogy to Example 208 b): colourless solid; MS (ISP): 247.2 ((M+H)$^{+ \cdot}$).

Example 213

Rac-(4-Ethoxy-2,6-diethyl-phenyl)-(1H-imidazol-2-yl)-methanol

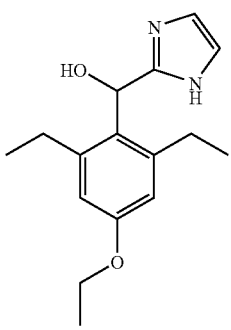

a) 2,6-Diethyl-4-hydroxy-benzaldehyde

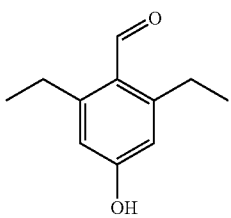

To a solution of 9.00 g (46.8 mmol)) 2,6-diethyl-4-methoxy-benzaldehyde in 50 ml dichloromethane at −78° C. was added 103 ml (103 mmol) of a 1 M solution of boron tribromide in dichloromethane and the reaction mixture was allowed to warm to room temperature and then heated at reflux for 16 h. The reaction mixture was quenched by pouring onto ice and the resulting mixture was then diluted with ethyl acetate and washed sequentially with water and with saturated brine. The phases were separated and the organic phase was dried over Na$_2$SO$_4$, filtered and concentrated in vacuo to afford 8.68 g (100%) of the title compound as a brown crystalline solid. MS (ISP): 177.4 ([M-H]$^-$, 100%).

b) 4-Ethoxy-2,6-diethyl-benzaldehyde

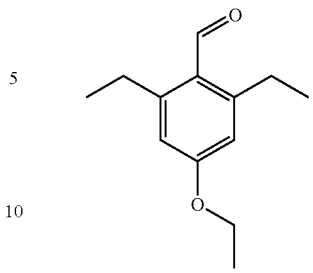

To a solution of 1.10 g (5.92 mmol)) 2,6-diethyl-4-hydroxy-benzaldehyde in 15 ml N,N-dimethylformamide in a pressure tube were added 4.83 g (14.8 mmol) cesium carbonate and 1.05 ml (13.0 mmol) iodomethane. The tube was sealed and the reaction mixture was heated at 60° C. for 16 h. The reaction mixture was cooled to room temperature, diluted with ether, and washed with saturated brine. The phases were separated and the organic phase was dried over Na$_2$SO$_4$, filtered, and concentrated in vacuo. The residue was purified by flash chromatography (silica gel, ethyl acetate/heptane gradient) to afford 1.00 g (82%) of the title compound as a yellow oil. $^1$H-NMR (CDCl$_3$): 1.25 (6H, t, 2×CH$_3$), 1.44 (3H, t, CH$_3$), 2.98 (4H, q, 2×CH$_2$), 4.10 (2H, q, OCH$_2$), 6.62 (2H, s, 2×ArH), 10.45 (1H, s, CH=O).

c) Rac-(4-Ethoxy-2,6-diethyl-phenyl)-(1H-imidazol-2-yl)-methanol

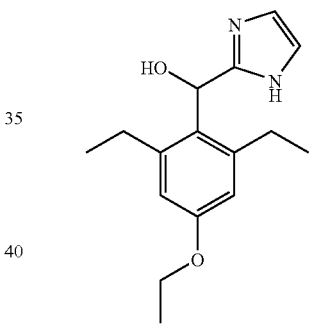

Rac-(4-ethoxy-2,6-diethyl-phenyl)-(1H-imidazol-2-yl)-methanol was prepared from 4-ethoxy-2,6-diethyl-benzaldehyde and 2-(1-diethoxymethyl-1H-imidazol-2-yl)-lithium in analogy to Example 191d): yellow crystals; MS (ISP): 275.5 ([M+H]$^+$, 69%), 257.3 ([M+H—H$_2$O]$^+$, 100%).

Example 214

Rac-(3-Ethoxy-2,6-diethyl-phenyl)-(1H-imidazol-2-yl)-methanol

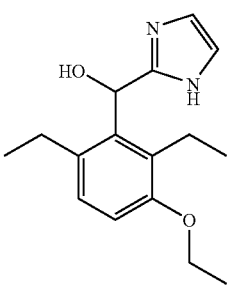

a) 2,6-Diethyl-3-hydroxy-benzaldehyde

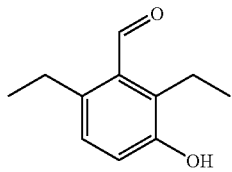

2,6-Diethyl-3-hydroxy-benzaldehyde was prepared from 2,6-diethyl-3-methoxy-benzaldehyde and boron tribromide in analogy to Example 213a): brown crystals; MS (ISP): 177.4 ([M-H]$^-$, 100%).

b) 3-Ethoxy-2,6-diethyl-benzaldehyde

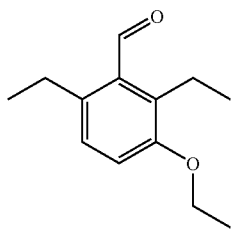

3-Ethoxy-2,6-diethyl-benzaldehyde was prepared from 2,6-diethyl-3-hydroxy-benzaldehyde, cesium carbonate and iodoethane in analogy to Example 213b): yellow oil; $^1$H-NMR (CDCl$_3$): 1.21 (3H, t, CH$_3$), 1.23 (3H, t, CH$_3$), 1.43 (3H, t, CH$_3$), 2.86 (2H, q, CH$_2$), 2.96 (2H, q, CH$_2$), 4.04 (2H, q, OCH$_2$), 6.96 (1H, d, ArH), 7.05 (1H, d, ArH), 10.57 (1H, s, CH=O).

c) Rac-(3-Ethoxy-2,6-diethyl-phenyl)-(1H-imidazol-2-yl)-methanol

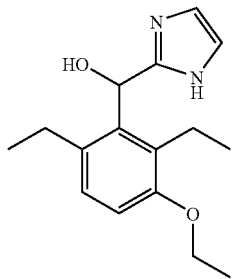

Rac-(3-ethoxy-2,6-diethyl-phenyl)-(1H-imidazol-2-yl)-methanol was prepared from 3-ethoxy-2,6-diethyl-benzaldehyde and 2-(1-diethoxymethyl-1H-imidazol-2-yl)-lithium in analogy to Example 191d): yellow oil; MS (ISP): 275.5 ([M+H]$^+$, 100%), 257.3 ([M+H—H$_2$O]$^+$, 77%).

Example 215

2-(4-Ethoxy-2,6-diethyl-benzyl)-1H-imidazole

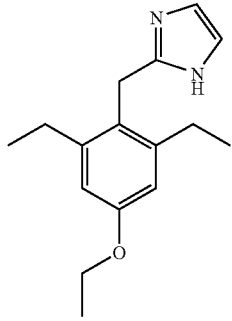

2-(4-Ethoxy-2,6-diethyl-benzyl)-1H-imidazole was prepared from rac-(4-ethoxy-2,6-diethyl-phenyl)-(1H-imidazol-2-yl)-methanol, triethylsilane and trifluoroacetic acid in analogy to Example 191e): light yellow crystals; MS (ISP): 259.4 ([M+H]$^+$, 100%).

Example 216

2-(4-Benzyloxy-2,6-diethyl-benzyl)-1H-imidazole

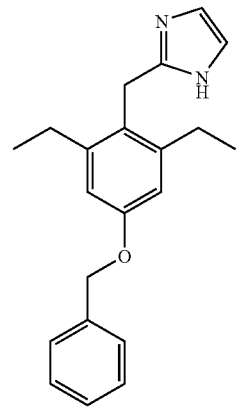

a) 4-Benzyloxy-2,6-diethyl-benzaldehyde

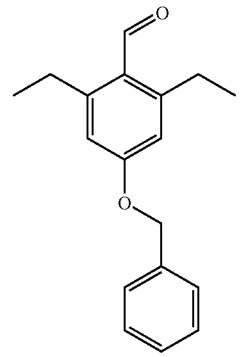

4-Benzyloxy-2,6-diethyl-benzaldehyde was prepared from 2,6-diethyl-4-hydroxy-benzaldehyde, cesium carbonate and benzyl bromide in analogy to Example 213b): yellow oil; $^1$H-NMR (CDCl$_3$): 1.25 (6H, t, 2×CH$_3$), 2.98 (4H, q, 2×CH$_2$), 5.12 (2H, s, OCH$_2$), 6.72 (2H, s, 2×ArH), 7.33-7.45 (5H, m, Ph), 10.47 (1H, s, CH=O).

b) Rac-(4-Benzyloxy-2,6-diethyl-phenyl)-(1H-imidazol-2-yl)-methanol

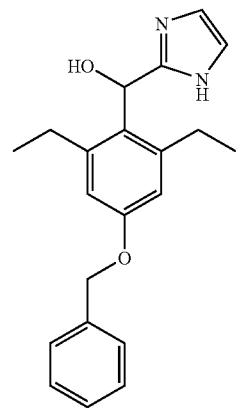

Rac-(4-benzyloxy-2,6-diethyl-phenyl)-(1H-imidazol-2-yl)-methanol was prepared from 4-benzyloxy-2,6-diethyl-benzaldehyde and 2-(1-diethoxymethyl-1H-imidazol-2-yl)-lithium in analogy to Example 191d): yellow oil; MS (ISP): 337.5 ([M+H]$^+$, 100%), 319.1 ([M+H—H$_2$O]$^+$, 95%).

c) 2-(4-Benzyloxy-2,6-diethyl-benzyl)-1H-imidazole

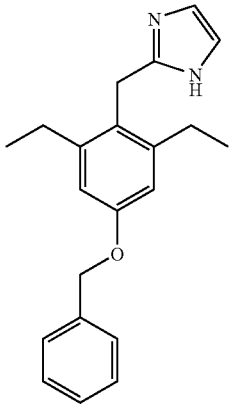

2-(4-Benzyloxy-2,6-diethyl-benzyl)-1H-imidazole was prepared from rac-(4-benzyloxy-2,6-diethyl-phenyl)-(1H-imidazol-2-yl)-methanol, triethylsilane and trifluoroacetic acid in analogy to Example 191e): white crystals; MS (ISP): 321.1 ([M+H]$^+$, 100%).

Example 217

2-(3-Ethoxy-2,6-diethyl-benzyl)-1H-imidazole

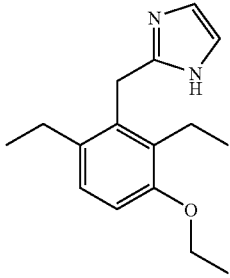

2-(3-Ethoxy-2,6-diethyl-benzyl)-1H-imidazole was prepared from rac-(3-ethoxy-2,6-diethyl-phenyl)-(1H-imidazol-2-yl)-methanol, triethylsilane and trifluoroacetic acid in analogy to Example 191e): light yellow crystals; MS (ISP): 259.3 ([M+H]$^+$, 100%).

Example 218

2-(3-Benzyloxy-2,6-diethyl-benzyl)-1H-imidazole

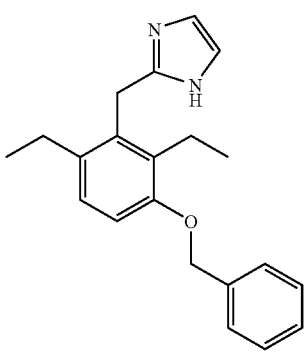

a) 3-Benzyloxy-2,6-diethyl-benzaldehyde

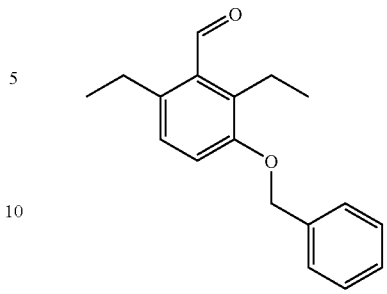

3-Benzyloxy-2,6-diethyl-benzaldehyde was prepared from 2,6-diethyl-3-hydroxy-benzaldehyde, cesium carbonate and benzyl bromide in analogy to Example 213b): yellow oil; $^1$H-NMR (CDCl$_3$): 1.20 (3H, t, CH$_3$), 1.21 (3H, t, CH$_3$), 2.87 (2H, q, CH$_2$), 3.03 (2H, q, CH$_2$), 5.09 (2H, s, OCH$_2$), 7.04 (2H, ABq, 2×ArH), 7.33-7.45 (5H, m, Ph), 10.58 (1H, s, CH═O).

b) Rac-(3-Benzyloxy-2,6-diethyl-phenyl)-(1H-imidazol-2-yl)-methanol

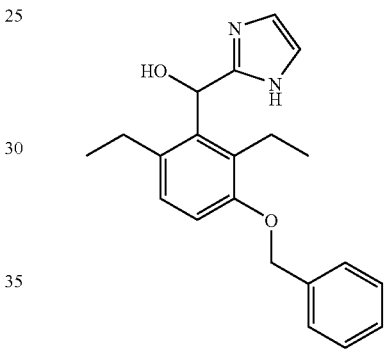

Rac-(3-benzyloxy-2,6-diethyl-phenyl)-(1H-imidazol-2-yl)-methanol was prepared from 3-benzyloxy-2,6-diethyl-benzaldehyde and 2-(1-diethoxymethyl-1H-imidazol-2-yl)-lithium in analogy to Example 191d): yellow oil; MS (ISP): 337.5 ([M+H]$^+$, 100%), 319.1 ([M+H—H$_2$O]$^+$, 36%).

c) 2-(3-Benzyloxy-2,6-diethyl-benzyl)-1H-imidazole

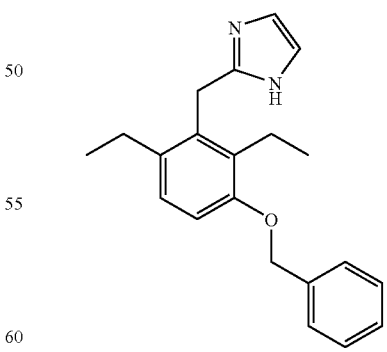

2-(3-Benzyloxy-2,6-diethyl-benzyl)-1H-imidazole was prepared from rac-(3-benzyloxy-2,6-diethyl-phenyl)-(1H-imidazol-2-yl)-methanol, triethylsilane and trifluoroacetic acid in analogy to Example 191e): off-white crystals; MS (ISP): 321.0 ([M+H]$^+$, 100%).

Example 219

2-(2,6-Diethyl-4-phenoxy-benzyl)-1H-imidazole

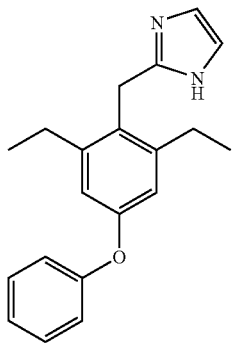

a) 2,6-Diethyl-4-phenoxy-benzaldehyde

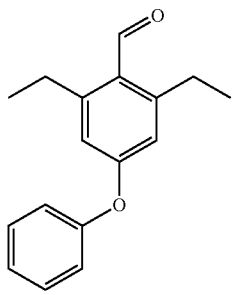

This compound was prepared using methodology described in *Tetrahedron Lett* 1998, 39, 2937-2940. To a solution of 1.50 g (8.42 mmol) 2,6-diethyl-4-hydroxy-benzaldehyde in 60 ml dichloromethane were added 1.64 g (13.5 mmol) phenylboronic acid, 2.29 g (12.6 mmol) copper(II) acetate, 30 g 4 Å molecular sieves and 4.06 ml (50.5 mmol) pyridine. The reaction mixture was stirred at room temperature for 72 h and then filtered through celite. The filtrate was extracted with 1 N aqueous hydrochloric acid, the phases were separated, and the organic phase was dried over $Na_2SO_4$, filtered and concentrated in vacuo. The residue was purified by flash chromatography (silica gel, ethyl acetate/heptane gradient) to afford 1.64 g (77%) of the title compound as a yellow oil. $^1$H-NMR ($CDCl_3$): 1.22 (6H, t, $CH_3$), 2.95 (4H, q, $CH_2$), 6.69 (2H, s, ArH), 7.08 (2H, d, ArH), 7.20 (1H, t, ArH), 7.39 (2H, dd, ArH), 10.5 (1H, s, CHO).

b) Rac-(2,6-Diethyl-4-phenoxy-phenyl)-(1H-imidazol-2-yl)-methanol

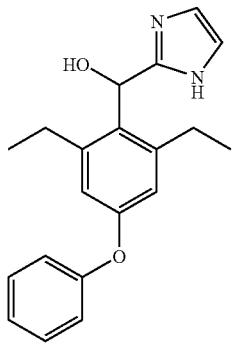

Rac-(2,6-Diethyl-4-phenoxy-phenyl)-(1H-imidazol-2-yl)-methanol was prepared from 2,6-diethyl-4-phenoxy-benzaldehyde and 2-(1-diethoxymethyl-1H-imidazol-2-yl)-lithium in analogy to Example 191d): yellow oil; MS (ISP): 323.3 ([M+H]$^+$, 100%), 305.1 ([M+H—$H_2O$]$^+$, 77%).

c) 2-(2,6-Diethyl-4-phenoxy-benzyl)-1H-imidazole

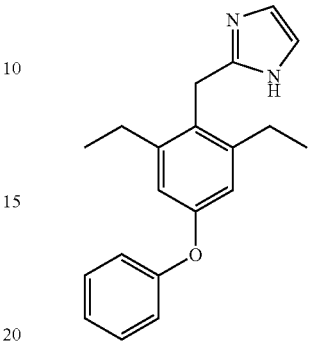

2-(2,6-Diethyl-4-phenoxy-benzyl)-1H-imidazole was prepared from rac-(2,6-diethyl-4-phenoxy-phenyl)-(1H-imidazol-2-yl)-methanol, triethylsilane and trifluoroacetic acid in analogy to Example 191e): white crystals; MS (ISP): 307.4 ([M+H]$^+$, 100%).

Example 220

2-(2,6-Diethyl-3-phenoxy-benzyl)-1H-imidazole

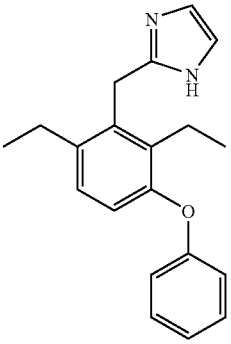

a) 2,6-Diethyl-3-phenoxy-benzaldehyde

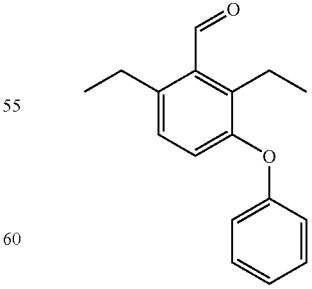

2,6-Diethyl-3-phenoxy-benzaldehyde was prepared from 2,6-diethyl-3-hydroxy-benzaldehyde and phenylboronic acid in analogy to Example 219a): yellow oil; $^1$H-NMR ($CDCl_3$): 1.20 (3H, t, $CH_3$), 1.25 (3H, t, $CH_3$), 2.93 (2H, q, $CH_2$), 2.98

(2H, q, CH₂), 6.91 (2H, d, 2×ArH), 7.00-7.10 (3H, m, 3×ArH), 7.28-7.38 (2H, m, 2×ArH), 10.6 (1H, s, CHO).

b) Rac-(2,6-Diethyl-3-phenoxy-phenyl)-(1H-imidazol-2-yl)-methanol

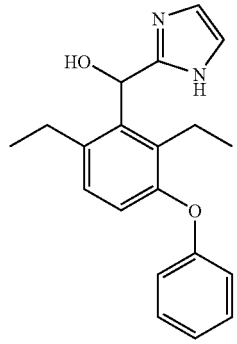

Rac-(2,6-Diethyl-3-phenoxy-phenyl)-(1H-imidazol-2-yl)-methanol was prepared from 2,6-diethyl-3-phenoxy-benzaldehyde and 2-(1-diethoxymethyl-1H-imidazol-2-yl)-lithium in analogy to Example 191d): yellow oil; MS (ISP): 323.4 ([M+H]⁺, 100%), 305.1 ([M+H—H₂O]⁺, 41%).

c) 2-(2,6-Diethyl-3-phenoxy-benzyl)-1H-imidazole

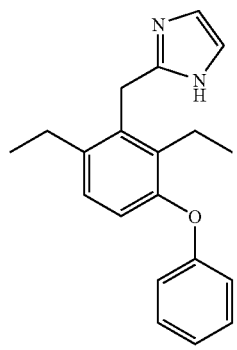

2-(2,6-Diethyl-3-phenoxy-benzyl)-1H-imidazole was prepared from rac-(2,6-diethyl-3-phenoxy-phenyl)-(1H-imidazol-2-yl)-methanol, triethylsilane and trifluoroacetic acid in analogy to Example 191e): white crystals; MS (ISP): 307.3 ([M+H]⁺, 100%).

Example 221

2-[3-(1H-Imidazol-2-ylmethyl)-phenyl]-pyridine

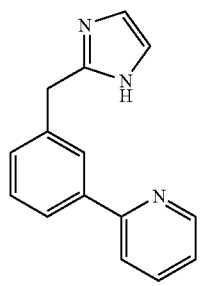

a) Rac-(1H-Imidazol-2-yl)-(3-pyridin-2-yl-phenyl)-methanol

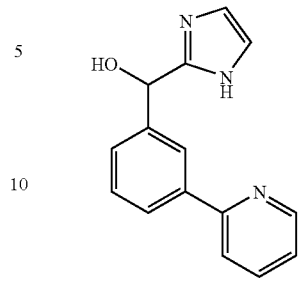

Rac-(1H-Imidazol-2-yl)-(3-pyridin-2-yl-phenyl)-methanol was prepared from 3-(2-pyridyl)benzaldehyde and 2-(1-diethoxymethyl-1H-imidazol-2-yl)-lithium in analogy to Example 191d): yellow oil; MS (ISP): 252.1 ([M+H]⁺, 100%), 234.1 ([M+H—H₂O]⁺, 51%).

b) 2-[3-(1H-Imidazol-2-ylmethyl)-phenyl]-pyridine

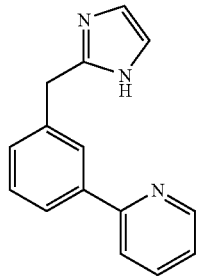

2-[3-(1H-Imidazol-2-ylmethyl)-phenyl]-pyridine was prepared from rac-(1H-imidazol-2-yl)-(3-pyridin-2-yl-phenyl)-methanol, triethylsilane and trifluoroacetic acid in analogy to Example 191e): white crystals; MS (ISP): 236.3 ([M+H]⁺, 100%).

Example 222

3-[3-(1H-Imidazol-2-ylmethyl)-phenyl]-pyridine

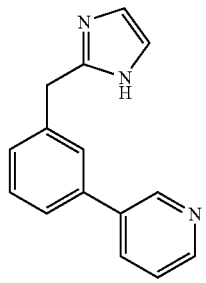

a) Rac-(1H-Imidazol-2-yl)-(3-pyridin-3-yl-phenyl)-methanol

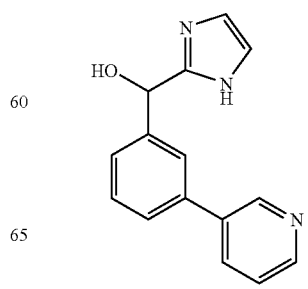

Rac-(1H-Imidazol-2-yl)-(3-pyridin-3-yl-phenyl)-methanol was prepared from 3-(3-pyridyl)benzaldehyde and 2-(1-diethoxymethyl-1H-imidazol-2-yl)-lithium in analogy to Example 191d): yellow oil; MS (ISP): 252.4 ([M+H]$^+$, 100%), 234.3 ([M+H—H$_2$O]$^+$, 57%).

b) 3-[3-(1H-Imidazol-2-ylmethyl)-phenyl]-pyridine

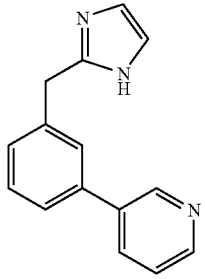

3-[3-(1H-Imidazol-2-ylmethyl)-phenyl]-pyridine was prepared from rac-(1H-imidazol-2-yl)-(3-pyridin-3-yl-phenyl)-methanol, triethylsilane and trifluoroacetic acid in analogy to Example 191e): white crystals; MS (ISP): 236.4 ([M+H]$^+$, 100%).

Example 223

4-[3-(1H-Imidazol-2-ylmethyl)-phenyl]-pyridine

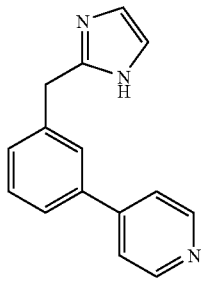

a) Rac-(1H-Imidazol-2-yl)-(3-pyridin-4-yl-phenyl)-methanol

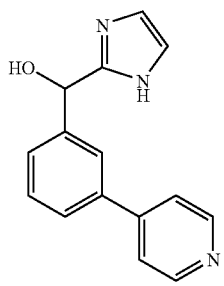

Rac-(1H-Imidazol-2-yl)-(3-pyridin-4-yl-phenyl)-methanol was prepared from 3-(4-pyridyl)benzaldehyde and 2-(1-diethoxymethyl-1H-imidazol-2-yl)-lithium in analogy to Example 191d): yellow oil; MS (ISP): 252.3 ([M+H]$^+$, 100%), 234.1 ([M+H—H$_2$O]$^+$, 55%).

b) 4-[3-(1H-Imidazol-2-ylmethyl)-phenyl]-pyridine

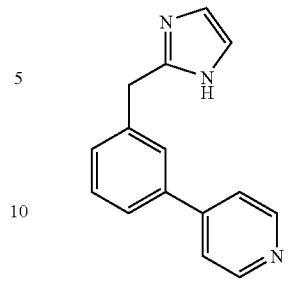

4-[3-(1H-Imidazol-2-ylmethyl)-phenyl]-pyridine was prepared from rac-(1H-imidazol-2-yl)-(3-pyridin-4-yl-phenyl)-methanol, triethylsilane and trifluoroacetic acid in analogy to Example 191e): white crystals; MS (ISP): 236.1 ([M+H]$^+$, 100%).

The invention claimed is:

1. A compound of formula I

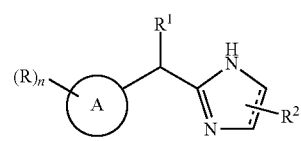

wherein
R is cycloalkyl,
lower alkoxy substituted by halogen,
O-phenyl, each of which is optionally substituted by halogen,
benzyl,
NHC(O)-lower alkyl or
pyridin-2,3 or 4-yl;
$R^1$ is hydrogen, hydroxy or lower alkyl;
$R^2$ is hydrogen;
A is an aryl group, selected from the group consisting of phenyl, a heteroaryl group, containing at least one O, N or S ring atom, selected from the group consisting of pyridine-3-yl, pyrazolyl, benzo[b]thiophen-3-yl and indol-3-yl; and
n is 1, 2, 3, 4 or 5; when n is 2, 3, 4 or 5, R may be the same or different;
the dotted line represents an optional bond;
or a pharmaceutically active salt thereof.

2. The compound of claim 1, wherein A is phenyl.

3. The compound of claim 2, which is 2-(2-cyclopropyl-benzyl)-4,5-dihydro-1H-imidazole.

4. A pharmaceutical composition comprising a therapeutically effective amount of a compound of formula I

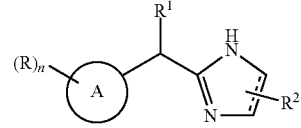

wherein
R is cycloalkyl,
lower alkoxy substituted by halogen,
O-phenyl, each of which is optionally substituted by halogen,
benzyl,
NHC(O)-lower alkyl or
pyridin-2,3 or 4-yl;
$R^1$ is hydrogen, hydroxy or lower alkyl;

$R^2$ is hydrogen;

A is an aryl group, selected from the group consisting of phenyl, naphthalen-1-yl and naphthalen-2-yl or a heteroaryl group, containing at least one O, N or S ring atom, selected from the group consisting of pyridine-3-yl, pyrazolyl, benzo[b]thiophen-3-yl and indol-3-yl; and n is 1, 2, 3, 4 or 5; when n is 2, 3, 4 or 5, R may be the same or different;

the dotted line represents an optional bond;

or a pharmaceutically active salt thereof, and a pharmaceutically acceptable carrier.

\* \* \* \* \*